US012678384B2

(12) United States Patent
Joshi et al.

(10) Patent No.: US 12,678,384 B2
(45) Date of Patent: Jul. 14, 2026

(54) SANITIZING COMPOSITIONS CONTAINING IONIC LIQUID

(71) Applicant: CAGE BIO INC., San Carlos, CA (US)

(72) Inventors: Nitin Joshi, San Carlos, CA (US); Marina Shevachman, San Carlos, CA (US); Abhirup Mandal, San Carlos, CA (US); Kevin W. Gelston, San Carlos, CA (US)

(73) Assignee: CAGE BIO INC., San Carlos, CA (US)

( * ) Notice: Subject to any disclaimer, the term of this patent is extended or adjusted under 35 U.S.C. 154(b) by 684 days.

(21) Appl. No.: 18/011,836

(22) PCT Filed: Jun. 25, 2021

(86) PCT No.: PCT/US2021/039243

§ 371 (c)(1),
(2) Date: Dec. 20, 2022

(87) PCT Pub. No.: WO2021/263201

PCT Pub. Date: Dec. 30, 2021

(65) Prior Publication Data

US 2023/0329988 A1 Oct. 19, 2023

Related U.S. Application Data

(60) Provisional application No. 63/055,328, filed on Jul. 22, 2020, provisional application No. 63/044,945, filed on Jun. 26, 2020.

(51) Int. Cl.

| | |
|---|---|
| ***A61K 8/41*** | (2006.01) |
| ***A61K 8/36*** | (2006.01) |
| ***A61Q 17/00*** | (2006.01) |

(52) U.S. Cl.
CPC .............. *A61K 8/416* (2013.01); *A61K 8/361* (2013.01); *A61Q 17/005* (2013.01)

(58) Field of Classification Search
CPC ...................................................... A61K 8/416
See application file for complete search history.

(56) References Cited

U.S. PATENT DOCUMENTS

| | | | | |
|---|---|---|---|---|
| 8,778,086 | B2 | 7/2014 | Sumnicht et al. | |
| 2006/0090777 | A1* | 5/2006 | Hecht | C11D 17/0017 134/42 |
| 2013/0029932 | A1* | 1/2013 | Kachi | A61K 8/345 514/738 |
| 2019/0192661 | A1 | 6/2019 | Zakrewsky | |

OTHER PUBLICATIONS

Kuehn et al., J'nal of Undergraduate Research, vol. 15, Art. 5. (2017).*
Banerjee et al., PNAS, vol. 115 (28), (2018), pp. 7296-7301.*
International Search Report and Written Opinion for related PCT/US21/39243, dated Oct. 14, 2021, 7 pages.
Kuehn et al. "Choline Chloride Eutectics: Low Temperature Applications", (2017) The Journal of Undergraduate Research: vol. 15, Article 5. https://openprairie.sdstate.edu/jur/vol15/iss1/5; entire document, especially abstract, p. 1 para 2.
Banerjee et al., "Ionic liquids for oral insulin delivery", Jul. 10, 2018 (Jul. 10, 2018), PNAS vol. 115 No. 28, 7296-7301; entire document, especially p. 7296 col. 2 para 2.

* cited by examiner

*Primary Examiner* — Paul V Ward
(74) *Attorney, Agent, or Firm* — PROCOPIO, CORY, HARGREAVES & SAVITCH LLP

(57) ABSTRACT

Disclosed herein are sanitizing compositions comprising an alcohol and non-volatile component. In certain embodiments, sanitizing compositions comprise an ionic liquid comprising a choline cation and fatty acid anion for use in sanitizing surfaces. In some embodiments, the ionic liquid is further formulated for topical administration.

27 Claims, 13 Drawing Sheets

FIG. 3A
DI Water, t=30min
FIG. 3B
70% Alcohol, t=30min
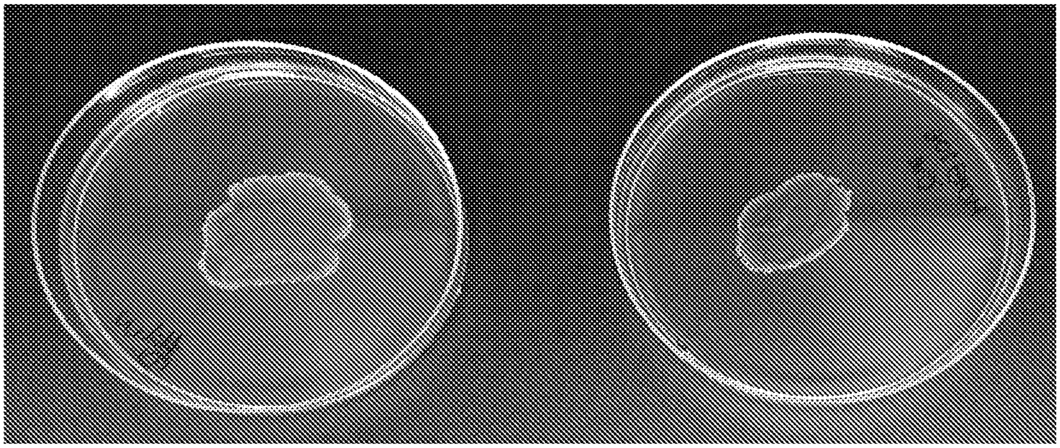
FIG. 3C
CAGE HS, t=30min
FIG. 3D
CAGE HS, t=1hr
FIG. 3E
CAGE HS, t=2hrs.
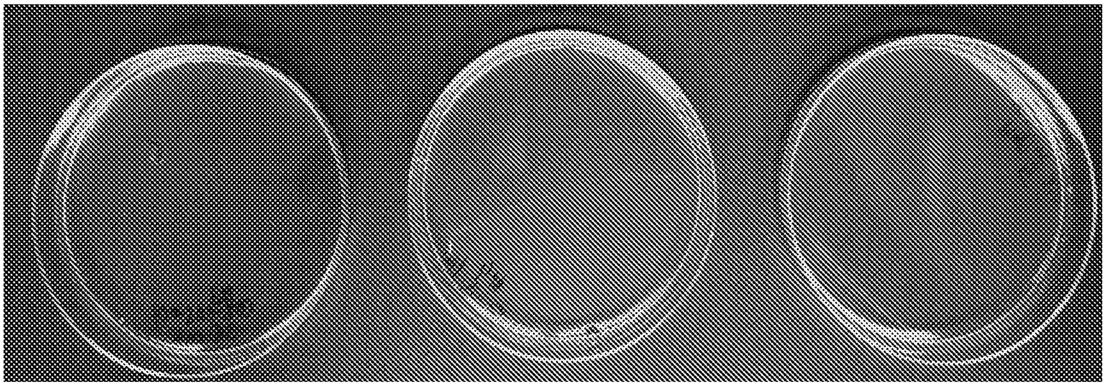

FIG. 4A
0.9% Saline solution, t=30min
FIG. 4B
Purell Advance HS Gel,
t=30min
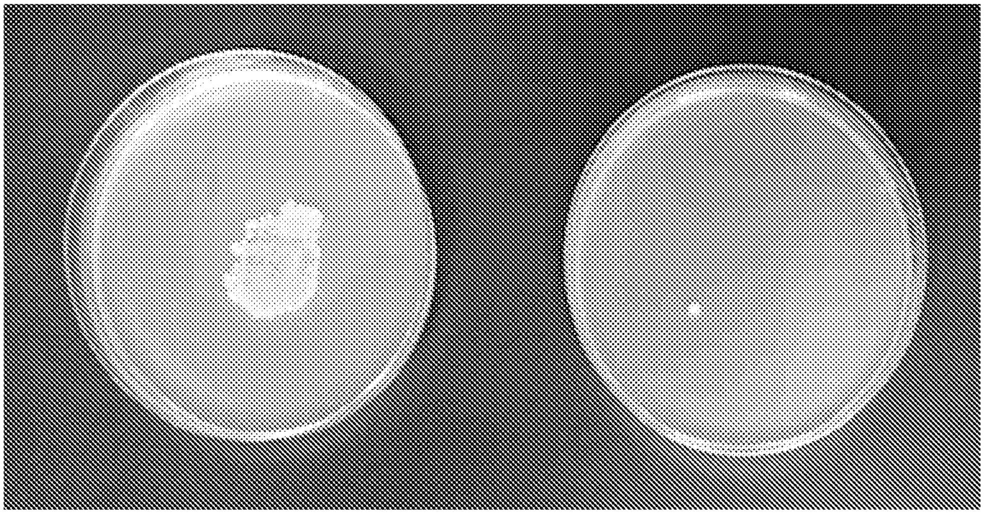
FIG. 4C
CAGE HS, t=30min
FIG. 4D
CAGE HS, t=2hrs
FIG. 4E
CAGE HS, t=4hrs
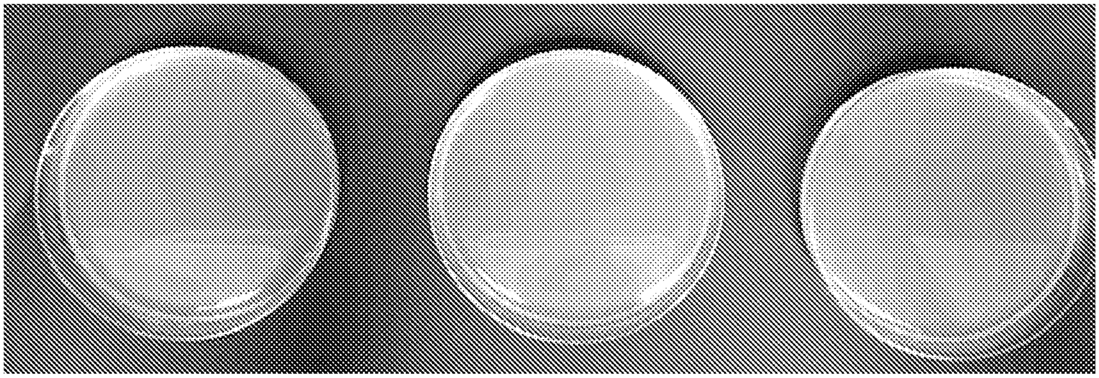

FIG. 5A
0.9% Saline solution,
t=30min
FIG. 5B
Purell® Advance HS
Gel, t=30min
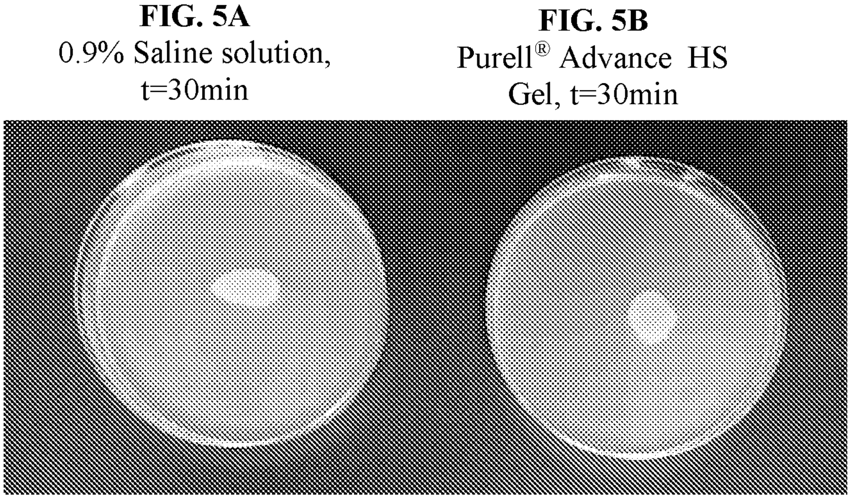
FIG. 5C
CAGE HS, t=30min
FIG. 5D
CAGE HS, t=2hrs
FIG. 5E
CAGE HS, t=4hrs
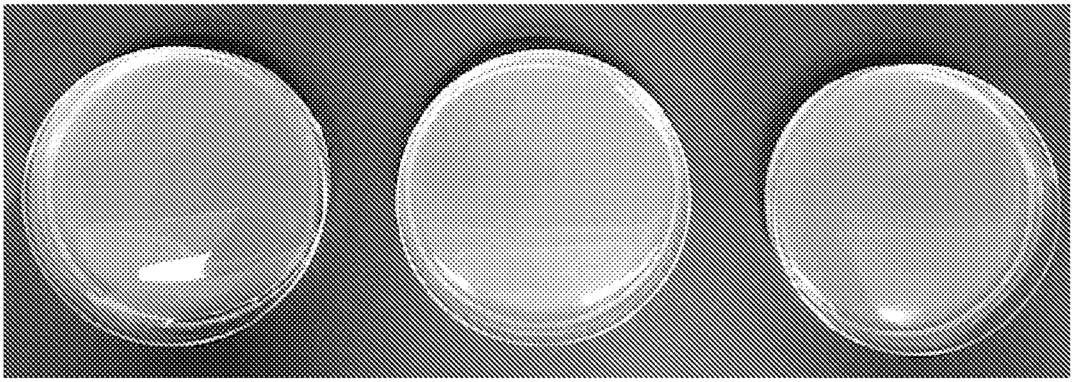

FIG. 6A
0.9% Saline solution,
t=30min
FIG. 6B
Purell Advance HS Gel,
t=30min
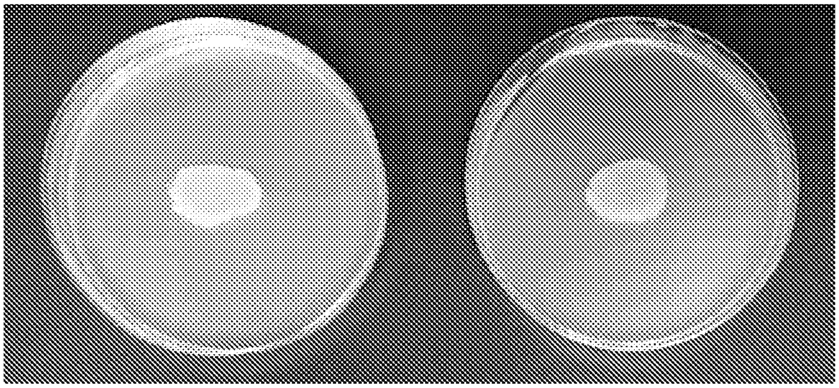
FIG. 6C
CAGE HS, t=30min
FIG. 6D
CAGE HS, t=2hrs
FIG. 6E
CAGE HS, t=4hrs
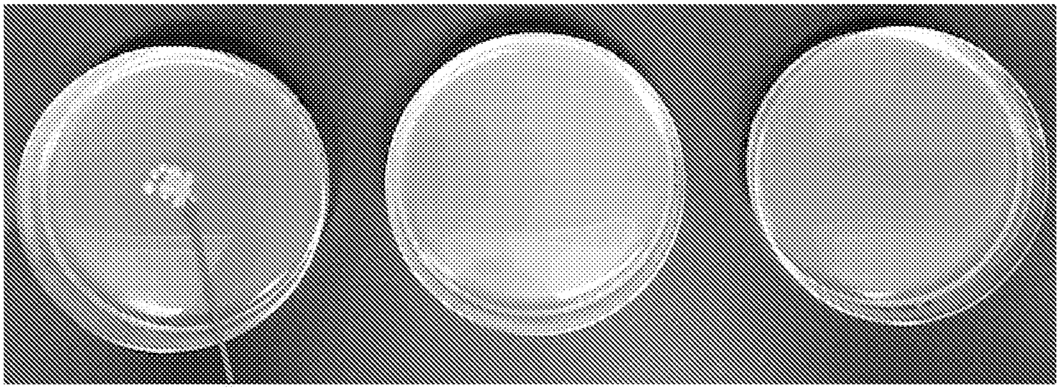
The inoculum was not dry when the finger was pressed on the agar media

FIG. 7A
0.9% Saline solution,
t=30min
FIG. 7B
Purell Advance HS Gel,
t=30min
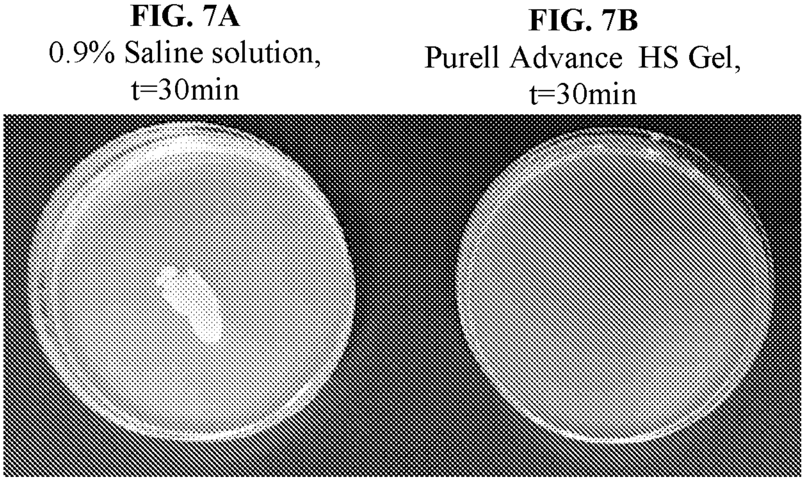
FIG. 7C
CAGE HS, t=30min
FIG. 7D
CAGE HS, t=2hrs
FIG. 7E
CAGE HS, t=4hrs
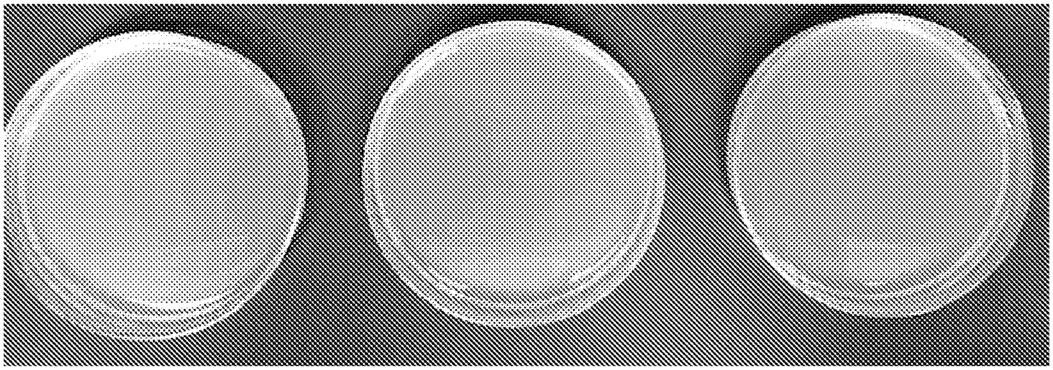

FIG. 8A
0.9% Saline solution,
t=30min
FIG. 8B
Purell Advance HS Gel,
t=30min
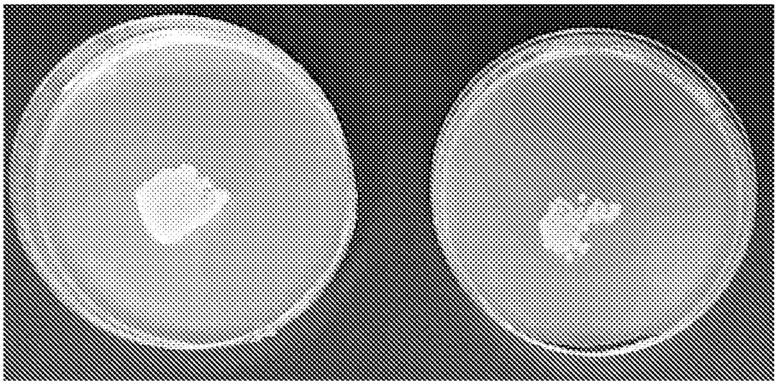
FIG. 8C
CAGE HS,
t=30min
FIG. 8D
CAGE HS, t=2hrs
FIG. 8E
CAGE HS, t=4hrs
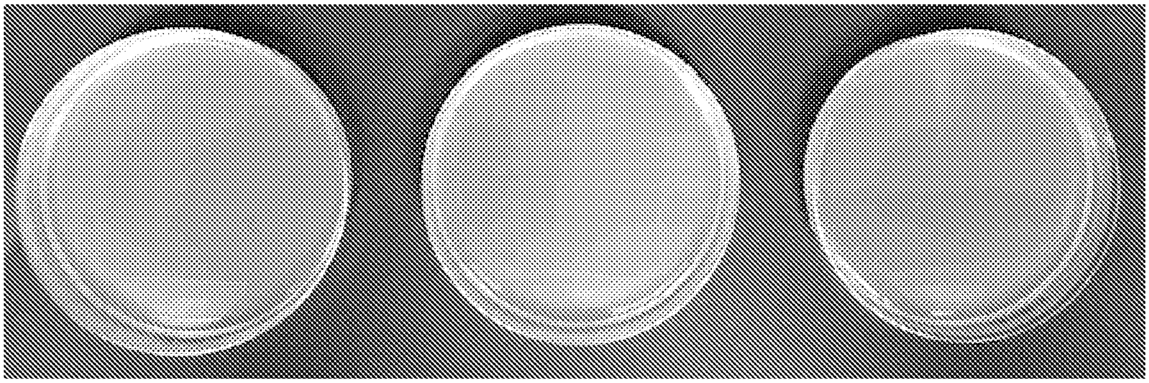

DI water, t=24 hrs

70% ethanol, t= 24 hrs

5% CAGE HS, t=30min

5% CAGE HS, t=1hr

5% CAGE HS, t=2 hrs

SANITIZING COMPOSITIONS CONTAINING IONIC LIQUID

BACKGROUND

The use of sanitizing products continues to grow, both within the United States and internationally. Sanitizers can be found in hospitals and other healthcare environments, the workplace, and in everyday home use. These products are considered especially useful when microbial contamination is a concern, particular in high risk areas of hospitals and prior to surgical procedures.

SUMMARY OF THE DISCLOSURE

In an aspect, provided herein is a method of sanitizing a skin surface, comprising applying to the skin surface a composition comprising an ionic liquid having a cationic component and an anionic component, wherein the composition is non-irritating to skin.

In another aspect, provided herein is a method of sanitizing a skin surface, comprising applying to the skin surface a composition comprising a deep eutectic solvent having a cationic component and an anionic component, wherein the composition is non-irritating to skin, and wherein the deep eutectic solvent has a melting point lower than the melting points of the cationic component and anionic component individually In an aspect, provided herein is a method for inhibiting or decreasing microbial growth on a skin surface, comprising applying to the skin surface a composition, comprising an ionic liquid having a cationic component and an anionic component, wherein the composition is non-irritating to skin.

In an aspect, provided herein is a method for inhibiting or decreasing microbial growth on a skin surface, comprising applying to the skin surface a composition comprising a deep eutectic solvent having a cationic component and an anionic component, wherein the composition is non-irritating to skin, and wherein the deep eutectic solvent has a melting point lower than the melting points of the cationic component and anionic component individually.

In an aspect, provided herein is a wipe, comprising a surface retaining a releasable sanitizing composition, wherein the sanitizing composition comprises an ionic liquid having a cationic component and an anionic component, and wherein the composition is non-irritating to skin.

In an aspect, provided herein is a wipe, comprising a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

In an aspect, provided herein is a method of sanitizing a skin surface, comprising wiping the skin surface with a wipe, comprising a surface retaining a releasable sanitizing composition, wherein the sanitizing composition comprises an ionic liquid having a cationic component and an anionic component, and wherein the composition is non-irritating to skin.

In another aspect, provided herein is a method of sanitizing a skin surface, comprising wiping the skin surface with a wipe, comprising a surface retaining a releasable sanitizing composition, wherein the sanitizing composition comprises an ionic liquid having a cationic component and an anionic component, and wherein the composition is non-irritating to skin.

In an aspect, provided herein is a method for inhibiting or decreasing microbial growth on a skin surface, comprising wiping the surface with a wipe, comprising a surface retaining a releasable sanitizing composition, wherein the sanitizing composition comprises an ionic liquid having a cationic component and an anionic component, and wherein the composition is non-irritating to skin.

In an aspect, provided herein is a method for inhibiting or decreasing microbial growth on a skin surface, comprising wiping the skin surface with a wipe, comprising a surface retaining a releasable sanitizing composition, wherein the sanitizing composition comprises an ionic liquid having a cationic component and an anionic component, and wherein the composition is non-irritating to skin.

In an aspect, provided herein is a method of sanitizing a skin surface, comprising wiping the skin surface with a wipe, comprising a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

In another aspect, provided herein is a method of sanitizing a skin surface, comprising wiping the skin surface with a wipe, comprising a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

In an aspect, provided herein is a method for inhibiting or decreasing microbial growth on a skin surface, comprising wiping the skin surface with a wipe, comprising a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

In an aspect, provided herein is a method for inhibiting or decreasing microbial growth on a skin surface, comprising wiping the skin surface with a wipe, comprising a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

In some embodiments, the compositions of the present disclosure slow the spread of gram-positive and/or gram-negative bacteria, fungi, mold, viruses, protozoans, parasites, and other microbes. In some embodiments, the compositions of the present disclosure prevent or slow contamination of a surface with gram-positive and/or gram-negative bacteria, fungi, mold, viruses, protozoans, parasites, and other microbes.

In some embodiments, the microbial growth is growth of a virus, bacterium, fungus, mold, protozoan, parasite, or combinations thereof.

In some embodiments, the bacterium is a gram-negative bacterium. In some embodiments, the gram-negative bacterium is an *Escherichia, Salmonella, Klebsiella* bacterium, or any combination thereof. In some embodiments, the *Escherichia* bacterium is *E. coli.*

In some embodiments, the gram-positive bacterium is a *Staphylococcus* or *Streptococcus* bacterium.

In some embodiments, the *Staphylococcus* bacterium is *S. aureus*. In some embodiments, the *Staphylococcus* bacterium is methicillin-resistant *S. aureus* (MRSA). In some embodiments, the bacterium is *S. enterica, S. pyogenes, K. pneumoniae*, or any combination thereof.

In some embodiments, the virus is in Coronaviridae family. In some embodiments, the virus is in Orthocoronaviridae subfamily. In some embodiments, the virus is a Betacoronavirus (0-CoV). In some embodiments, the virus is a Sarbecovirus. In some embodiments, the virus is an Ebolavirus, Coronavirus, Rotavirus, Alphainfluenzavirus, Betainfluenzavirus, Deltainfluenzavirus, and/or Gammainfluenzavirus.

In some embodiments, the virus is a human virus. In some embodiments, the virus is severe acute respiratory syndrome coronavirus 2 (SARS-CoV-2). In some embodiments, the virus is human severe acute respiratory syndrome coronavirus 2 (SARS-CoV-2). In some embodiments, the virus is Influenza A, B, and/or C. In some embodiments, the virus is Influenza A2 virus.

In some embodiments, at least one of the anionic component and cationic component is irritating to the skin when applied in the absence of the other component.

In some embodiments, the anionic component is bistriflimide, a geranate, an oleate, a hexanoate, dodecyldimethyl ammonia propane sulfonate, N-lauryl sarcosinate, or a geraniolate.

In some embodiments, the cationic component is benzyl pyridinium, benzyl dimethyl dodecyl ammonium, a choline cation, phosphonium, benzethonium, or a phosphonium.

In some embodiments, the phosphonium is a tetraalkyl phosphonium of structural Formula (I): PR4, wherein R is a substituted or unsubstituted alkyl group.

In some embodiments, the cationic component is a choline cation. In some embodiments, the anionic component is a geranate anion.

In some embodiments, the cationic component and the anionic component are in a molar ratio ranging from 1:1 to 1:2 (cationic component to anionic component).

In some embodiments, the composition comprises from about 0.10% to about 40% by weight of choline geranate. In some embodiments, the composition comprises from about 1% to about 10% by weight of choline geranate.

In some embodiments, the composition further comprises pH adjuster, skin conditioner, drying time enhancer, dye, fragrance, gelling agent, humectant, emollient, or combinations thereof. In some embodiments, the alcohol is ethanol, isopropyl alcohol, n-propyl alcohol, or combinations thereof. In some embodiments, the alcohol is present in the composition in an amount of from about 50% to about 95% by weight. In some embodiments, the alcohol is present in the composition in an amount of about 70% by weight.

In some embodiments, the composition further comprises a fragrance agent. In some embodiments, the fragrance agent is an acid or a terpene of a citrus fruit. In some embodiments, the citrus fruit is an orange, a grapefruit, a lime, or a lemon. In some embodiments, the terpene is D-limonene. In some embodiments, the acid is citric acid or a derivative thereof. In some embodiments, the fragrance agent is D-limonene. In some embodiments, the fragrance agent is present in the composition an amount of from about 0.05% to about 5% by weight. In some embodiments, the fragrance agent is present in the composition an amount of from about 0.3% to about 1% by weight.

In some embodiments, the gelling agent is hydroxyethyl cellulose (HEC), hydroxypropyl cellulose (HPC), hydroxypropylmethyl cellulose (HPMC), or a combination thereof. In some embodiments, the gelling agent is HPC. In some embodiments, the gelling agent is present in the composition an amount of from about 0.05% to about 5% by weight. In some embodiments, the gelling agent is present in the composition an amount of from about 0.3% to about 1% by weight.

In some embodiments, the humectant is glycerin. In some embodiments, the humectant is present in the composition an amount of from about 0.5% to about 5% by weight. In some embodiments, the humectant is present in the composition an amount of from about 1% to about 2% by weight.

In some embodiments, the composition further comprises aloe vera.

In some embodiments, the composition further comprises emollients.

In some embodiments, the composition further comprises water, ethanol, diisopropyl adipate, polyethylene glycol (PEG), glycerin, propylene glycol, or a combination thereof.

In some embodiments, the skin is human skin. In some embodiments, the surface is hands of a human subject.

In some embodiments, the composition is applied directly to the skin surface. In some embodiments, the composition is placed on or in an applicator or dispenser, which then applies the composition to the surface. In some embodiments, the applicator or dispenser is a cloth, a wipe, a sponge, a mop, a squirt bottle, a spray bottle, a pump bottle, a tube, an automatic induction hand sterilizer, a bottle or container comprising a dropper, bottle or container comprising a pour spout, or a canister. In some embodiments, the spray bottle is a continuous spray bottle. In some embodiments, the spray bottle is a propellant-free continuous spray bottle. In some embodiments, the continuous spray bottle is a flairosol sprayer. In some embodiments, the spray bottle is an aerosol sprayer. In some embodiments, the spray bottle is a mist spray bottle. In some embodiments, the spray bottle is an aerosol sprayer.

In some embodiments, the composition is rinseless. In some embodiments, at least part of the composition evaporates off of the surface. In some embodiments, the composition, ionic liquid or deep eutectic solvent remains on the surface for at least about two hours. In some embodiments, the composition, ionic liquid or deep eutectic solvent remains on the surface for at least about four hours. In some embodiments, the composition, ionic liquid or deep eutectic solvent remains on the surface until cleaned off.

In some embodiments, the composition further comprises a sporicide and/or an additional antimicrobial agent. In some embodiments, the sporicide is hydrogen peroxide.

In some embodiments, the ionic liquid comprises the choline cation and geranic acid anion in a molar ratio of 1:1 or 1:2 of choline cation to geranic acid anion. In some embodiments, the ionic liquid comprises the choline cation and geranic acid anion in a molar ratio in a range of 1:1 to 1:4 of choline cation to geranic acid anion. In some embodiments, the ionic liquid comprises the choline cation and geranic acid anion in a molar ratio of 1:1, 1:2, 1:3, or 1:4 of choline cation to geranic acid anion. In some embodiments, the composition provides an increased antimicrobial action compared to an antimicrobial action of choline or an antimicrobial action of geranic acid. In some embodiments, the increased antimicrobial action is a 10 fold less concentration of the composition required for complete killing of a microbe relative to a concentration of choline or a concentration of geranic acid required for complete killing of the microbe. In some embodiments, the ionic liquid comprises a concentration of about 0.10% to 99% of the composition, and the pharmaceutically acceptable solvent comprises a concentration of about 1% to about 99.9% of the composition.

In some embodiments, the composition is formulated as a liquid, gel, cream, foam, lotion, cream, wetting composition, or a spray. In some embodiments, the composition is formulated for topical administration. In some embodiments, the composition is formulated as a gel.

In some embodiments, the composition comprises 20% to 60% of an ionic liquid comprising a choline cation and a geranic acid anion, 5% to 20% by weight propylene glycol, and a remaining balance of water. In some embodiments, the composition comprises 30% to 50% of the ionic liquid. In some embodiments, the composition comprises a molar ratio of the choline cation and geranic acid anion of 1:2. In some embodiments, the composition comprises 10% to 15% by weight propylene glycol. In some embodiments, the composition further comprises 0.5% to 5% by weight hydroxyethyl cellulose. In some embodiments, the composition further comprises 0.5% to 5% by weight D-limonene.

In some embodiments, the composition further comprises ethylbenzyl ammonium choride, benzalkonium chloride, denatured alcohol, PEG-8 dimethicone, phenoxyethanol, quaternium-52, potassium sorbate, sodium capryloamphopropionate, methylparaben, citric acid, disodium EDTA, ethylparaben, PEG-60 lanolin, propylparaben, Aloe Barbadensis leaf juice, acrylates $C_{10-30}$ alkyl acrylate crosspolymer, benzophenone-4, glycerin, tocopherol, dipropylene glycol butyl ether, citric acid, sodium methyl 2-sulfolaurate, $C_{10}$ ethoxylated alcohol, $C_{10-16}$ alkyl glucoside, 2,6-dimethyl-2-heptanol, alpha-methylbenzyl acetate, dihydromyrcenol, dipropylene glycol, ethylene brassylate, gamma-decalactone, tricyclodecenyl propionate, sodium sulfate, or any combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 3A-3E show bacterial growth on TSA agar plates after fingers were inoculated negative control, 70% isopropyl alcohol, and Sanitizer A (results for the study of Example 4). FIG. 3A: DI Water, t=30 min; FIG. 3B: 70% isopropyl alcohol, t=30 min; FIG. 3C: Sanitizer A, t=30 min; FIG. 3D: Sanitizer A, t=1 hr; FIG. 3E: SANITIZER A, t=2 hrs.

FIGS. 4A-4E show bacterial growth on TSA agar plates after fingers were inoculated negative control, 70% isopropyl alcohol, and SANITIZER A (results for the study of Example 4). FIG. 4A: DI Water, t=30 min; FIG. 4B: 70% isopropyl alcohol, t=30 min; FIG. 4C: SANITIZER A, t=30 min; FIG. 4D: SANITIZER A, t=1 hr; FIG. 4E: SANITIZER A, t=2 hrs.

FIGS. 5A-5E show bacterial growth on TSA agar plates after fingers were inoculated negative control, 70% isopropyl alcohol, and SANITIZER A (results for the study of Example 4). FIG. 5A: DI Water, t=30 min; FIG. 5B: 70% isopropyl alcohol, t=30 min; FIG. 5C: SANITIZER A, t=30 min; FIG. 5D: SANITIZER A, t=1 hr; FIG. 5E: SANITIZER A, t=2 hrs.

FIGS. 6A-6E show bacterial growth on TSA agar plates after fingers were inoculated negative control, 70% isopropyl alcohol, and SANITIZER A (results for the study of Example 4). FIG. 6A: DI Water, t=30 min; FIG. 6B: 70% isopropyl alcohol, t=30 min; FIG. 6C: SANITIZER A, t=30 min; FIG. 6D: SANITIZER A, t=1 hr; FIG. 6E: SANITIZER A, t=2 hrs.

FIGS. 7A-7E show bacterial growth on TSA agar plates after fingers were inoculated negative control, 70% isopropyl alcohol, and SANITIZER A (results for the study of Example 4). FIG. 7A: DI Water, t=30 min; FIG. 7B: 70% isopropyl alcohol, t=30 min; FIG. 7C: SANITIZER A, t=30 min; FIG. 7D: SANITIZER A, t=1 hr; FIG. 7E: SANITIZER A, t=2 hrs.

FIGS. 8A-8E show bacterial growth on TSA agar plates after fingers were inoculated negative control, 70% isopropyl alcohol, and SANITIZER A (results for the study of Example 4). FIG. 8A: DI Water, t=30 min; FIG. 8B: 70% isopropyl alcohol, t=30 min; FIG. 8C: SANITIZER A, t=30 min; FIG. 8D: SANITIZER A, t=1 hr; FIG. 8E: SANITIZER A, t=2 hrs.

FIG. 9A: DI Water, t=24 hrs;

FIG. 9B: 70% ethanol, t=24 hrs; FIG. 9C: 5% SANITIZER A, t=30 min; FIG. 9D: 5% SANITIZER A, t=1 hr; FIG. 9E: 5% SANITIZER A, t=2 hrs.

DETAILED DESCRIPTION OF THE DISCLOSURE

Figure 1:
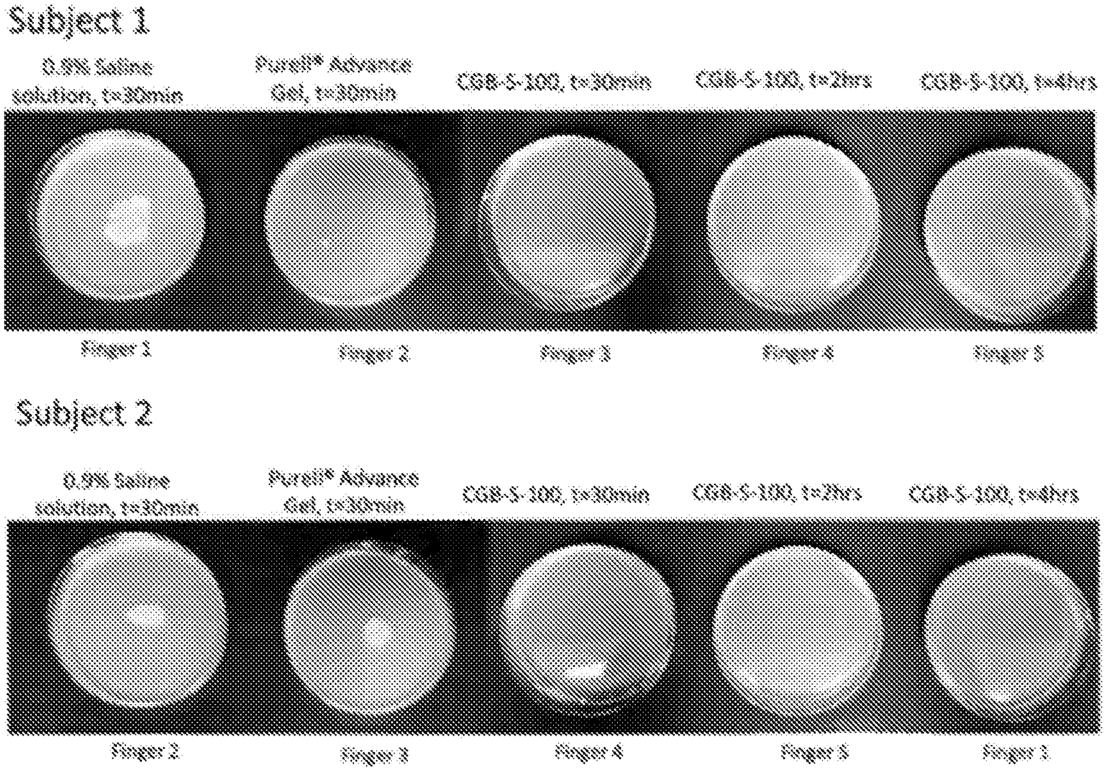
FIG. 1 shows the results of in vivo study of CGB-S-100 versus Purell® Advance and saline.
Figure 1:
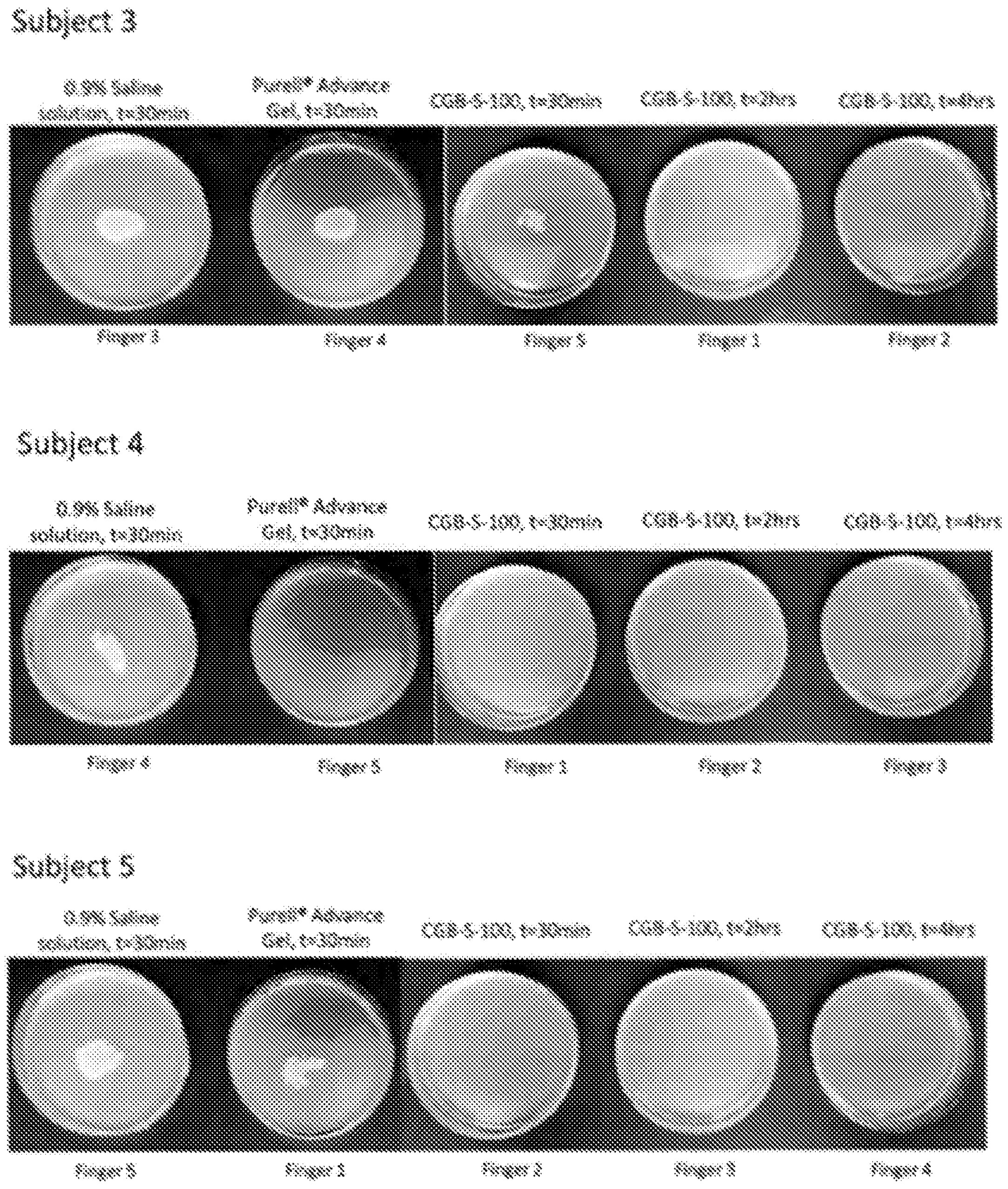

Alcohol and alcohol gels in which alcohol levels exceed about 50% have the most pronounced immediate antimicrobial effects; however, they lack persistent antimicrobial properties, i.e., residual activity or effect. Although alcohol may kill microbes on contact, upon drying, there is no means for killing or controlling microbial growth. As such, sanitizers using alcohol alone are often less effective over time. There is a need, therefore, for hand sanitizers having enhanced and prolonged antimicrobial activity and excellent residual activity.

I. Definitions

The terminology used herein is for the purpose of describing particular cases only and is not intended to be limiting. The below terms are discussed to illustrate meanings of the terms as used in this specification, in addition to the understanding of these terms by those of skill in the art. As used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. Where a range of values is provided, it is understood that each intervening value, to the tenth of the unit of the lower limit unless the context clearly dictates otherwise, between the upper and lower limit of that range and any other stated or intervening value in that stated range, is encompassed within the methods and compositions described herein are. The upper and lower limits of these smaller ranges may independently be included in the smaller ranges and are also encompassed within the methods and compositions described herein, subject to any specifically excluded limit in the stated range. Where the stated range includes one or both of the limits, ranges excluding either or both of those included limits are also included in the methods and compositions described herein.

The terms "individual," "patient," or "subject" are used interchangeably. None of the terms require or are limited to situation characterized by the supervision (e.g., constant or intermittent) of a health care worker (e.g. a doctor, a registered nurse, a nurse practitioner, a physician's assistant, an orderly, or a hospice worker). Further, these terms refer to human or animal subjects.

"Treating" or "treatment" refers to both therapeutic treatment and prophylactic or preventative measures, wherein the object is to prevent or slow down (lessen) a targeted pathologic condition or disorder.

The term "antimicrobial agent" is an agent that kills microorganisms, stops or slows their growth, or prevents their growth. Antimicrobial agents diminish the number of microbes on a surface. Examples of antimicrobial agents include, but are not limited to, disinfectants, antiseptics, antiviral agents, and antibiotics.

"Microbes" or "microorganisms," as referred to herein, are synonymous and used interchangeably. A microorganism, or microbe, is a microscopic organism, which may exist in its single-celled form or in a colony of cells. Microorganisms include all unicellular organisms. Microbes include, but are not limited to, viruses, archaea, bacteria, and eukaryotes such as protists (e.g., algae species), and fungi.

The terms "bacteria," "bacterium," and "bacterial growth" are used interchangeably to mean The percentages given herein refer to the percentage by weight of the specified component in a mixture, i.e. "weight percent." The terms "weight percent," "% by weight," "% w/w," and "wt. %" are synonymous and used interchangeably herein.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

II. Sanitizing Ionic Liquid Compositions

Described herein, in certain embodiments, are compositions comprising an ionic liquid comprising a choline cation and a fatty acid anion. In some embodiments, the composition further comprises a pharmaceutically acceptable solvent. In some embodiments, the fatty acid is myristoleic acid, palmitoleic acid, sapienic acid, oleic acid, elaidic acid, geranic acid, vaccenic acid, linoleic acid, linoelaidic acid, α-linolenic acid, arachidonic acid, eicosapentaenoic acid, erucic acid, docosahexaenoic acid, propionic acid, butyric acid, valeric acid, hexanoic acid, enanthic acid, caprylic acid, pelargonic acid, capric acid, undecylic acid, lauric acid, tridecyclic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, or hexatriacontylic acid. In some embodiments, the fatty acid is geranic acid. In some embodiments, the fatty acid comprises 9 to 14 carbons. In some embodiments, the ionic liquid is liquid at room temperature. In some embodiments, the ionic liquid is liquid below 100° C.

In some embodiments, the ionic liquid is a deep eutectic solvent (DES). In some embodiments, a DES comprises excess carboxylate which precludes 1:1 ion pairing. In some embodiments, a DES further comprises a hydrogen-bond donor. In some embodiments, the hydrogen-bond donor is urea or citric acid. In some embodiments, the solvent properties of a DES are adjusted by changing the hydrogen-bond donor. In some embodiments, the ammonium salt of a DES interacts with a hydrogen-bond donor. In some embodiments, the DES has a melting point lower than either of the individual components (e.g., fatty acid and choline).

In some embodiments, the ionic liquid comprises a molar ratio of a choline cation to a fatty acid anion of 1:0.5 to 1:10. In some embodiments, the molar ratio of the choline cation to the fatty acid anion is about 1:0.5, 1:0.6, 1:0.7, 1:0.8, 1:0.9, 1:1.0; 1:1.1, 1:1.2, 1:1.3, 1:1.4, 1:1.5, 1:1.6, 1:1.7, 1:1.8, 1:1.9, 1:2.0, 1:2.1, 1:2.2, 1:2.3, 1:2.4, 1:2.5, 1:2.6, 1:2.7, 1:2.8, 1:2.9, 1:3.0, 1:3.1, 1:3.2, 1:3.3, 1:3.4, 1:3.5, 1:3.6, 1:3.7, 1:3.8, 1:3.9, 1:4.0, 1:4.1, 1:4.2, 1:4.3, 1:4.4, 1:4.5, 1:4.6, 1:4.7, 1:4.8, 1:4.9. 1:5.0, 1:5.1, 1:5.2, 1:5.3, 1:5.4, 1:5.5, 1:5.6, 1:5.7, 1:5.8, 1:5.9, 1:6.0, 1:6.1, 1:6.2, 1:6.3, 1:6.4, 1:6.5, 1:6.6, 1:6.7, 1:6.8, 1:6.9, 1:7.0, 1:7.1, 1:7.2, 1:7.3, 1:7.4, 1:7.5, 1:7.6, 1:7.7, 1:7.8, 1:7.9, 1:8.0, 1:8.1, 1:8.2, 1:8.3, 1:8.4, 1:8.5, 1:8.6, 1:8.7, 1:8.8, 1:8.9, 1:9.0, 1:9.1, 1:9.2, 1:9.3, 1:9.4, 1:9.5, 1:9.6, 1:9.7, 1:9.8, 1:9.9, or about 1:10. In some embodiments, the molar ratio of the choline cation to the fatty acid anion is about 1:1.1, 1:1.2, 1:1.3, 1:1.4, 1:1.5, 1:1.6, 1:1.7, 1:1.8, 1:1.9, or 1:2.0.

In some embodiments, the choline cation and fatty acid anion are in a molar ratio in the ionic liquid. In some embodiments, the choline cation and fatty acid anion are in a molar ratio of 1:1. In some embodiments, the term Composition B is used herein to refer to a composition or an ionic liquid comprising a 1:1 molar ratio of choline cation to geranic acid anion. In some embodiments, Composition B does not comprise water.

In other embodiments, the choline cation and fatty acid anion are in a molar ratio of 1:2. In some embodiments, the term Composition A is used herein to refer to a composition or an ionic liquid comprising a 1:2 molar ratio of choline cation to geranic acid anion. In some embodiments, Composition A does not comprise water.

In some embodiments, the chemical structure of choline is:

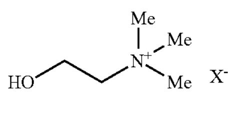

wherein $X^-$ is a pharmaceutically acceptable anion.

In some embodiments, term choline refers to the class of quaternary ammonium salts containing the N,N,N-trimethylethanolammonium cation. In some embodiments, the $X^-$ on the right of the structure of choline denotes a pharmaceutically acceptable anion. In some embodiments the $X^-$ is bicarbonate, carbonate, acetate, citrate, tartarate, bitartarate, lactate, chloride, bromide, or iodide. In some embodiments, the $X^-$ is bicarbonate. In some embodiments, the choline is an anti-inflammatory agent.

In some embodiments, choline is in the form of a pharmaceutically acceptable salt. The type of pharmaceutical acceptable salts, include, but are not limited to acid addition salts, formed by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In some embodiments, the chemical structure of geranic acid, or 3,7-dimethyl-2,6-octadienoic acid, is:

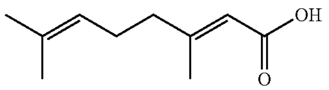

In some embodiments, geranic acid is in the form of a pharmaceutically acceptable salt. The type of pharmaceutical acceptable salts, include, but are not limited to salts formed when an acidic proton present in the parent compound either is replaced by a metal ion, e.g., an alkali metal ion (e.g. lithium, sodium, potassium), an alkaline earth ion (e.g., magnesium, or calcium), or an aluminum ion; or coordinates with an organic base. Examples of acceptable organic bases include, but are not limited to, ethanolamine, diethanolamine, triethanolamine, tromethamine, and N-methylglucamine. Examples of acceptable inorganic bases include, but are not limited to, aluminum hydroxide, calcium hydroxide, potassium hydroxide, sodium carbonate, and sodium hydroxide.

In some embodiments, the choline and the fatty acid are synthesized using any suitable standard synthetic reactions. In some embodiments, the reactions are employed in a linear sequence to provide the compounds or they may be used to synthesize fragments which are subsequently joined by any suitable method. In some embodiments, the starting material used for the synthesis of choline or fatty acid is synthesized or are obtained from commercial sources.

In some embodiments, geranic acid is purified from the commercially available technical grade (Sigma-Aldrich, St. Louis, Mo.) by repeated (5-7×) recrystallization from a solution of 70 wt % geranic acid/30 wt % acetone at −70° C. In some embodiments, purity of the geranic acid is assessed by $^1H$ NMR spectroscopy and conductivity measurements. In some embodiments, the term geranic acid refers to a geranic acid or a salt thereof. In some embodiments, the geranic acid is an anti-microbial agent.

In some embodiments, the compositions disclosed herein further comprise a pharmaceutically acceptable solvent is water, ethanol, diisopropyl adipate, polyethylene glycol (PEG), glycerin, propylene glycol, a short chain fatty acid, a fatty acid ester, or a combination thereof. In some embodiments, the pharmaceutically acceptable solvent is a liquid alcohol, liquid glycol, liquid polyalkalene glycol, liquid ester, liquid amine, liquid protein hydrolysate, liquid alkalated protein hydrolysate, liquid lanolin, lanolin derivative, water, or combinations thereof. In some embodiments, the pharmaceutically acceptable solvent is diisopropyl adipate. In some embodiments, the composition is miscible with the pharmaceutically acceptable solvent. In some embodiments, at least one of the individual components of the composition is not miscible with pharmaceutically acceptable solvent. In some embodiments, the composition is miscible with diisopropyl adipate. In some embodiments, at least one of the individual components of the composition is not miscible with diisopropyul adipate. In some embodiments, the water is deionized water or Milli-Q® water. In some embodiments, the composition does not comprise a preservative. Examples of preservatives include, but are not limited to, a paraben or a phenoxyethanol.

In some embodiments, the composition comprises an increased antimicrobial action compared to an antimicrobial action of choline or an antimicrobial action of the fatty acid. In some embodiments, the increased antimicrobial action is a 10 fold less concentration of the composition required for complete killing of a microbe relative to a concentration of choline or a concentration of the fatty acid required for complete killing of the microbe.

In some embodiments, the composition has decreased skin irritation relative to a skin irritation of choline or a skin irritation of the fatty acid. In some embodiments, the composition exhibits minimal cytotoxicity relative to a cytotoxicity of choline or a cytotoxicity of the fatty acid. In some embodiments, the composition comprises an increased conductivity relative to a conductivity of the fatty acid and a decreased conductivity relative to a conductivity of choline.

In some embodiments, the composition is clear. In some embodiments, the composition is turbid. In some embodiments, the composition is opaque. In some embodiments, the composition is yellow. In some embodiments, the composition is a colloidal system.

In some embodiments, the composition is formulated as a liquid, gel, cream, foam, lotion, cream, wetting composition, or a spray. In some embodiments, the composition is formulated as a gel.

In some embodiments, the composition further comprises a gelling agent, a viscosity modifying agent, an alcohol, an emollient, pH adjuster, skin conditioner, drying time enhancer, dye, fragrance, humectant, emollient, or a combination thereof. In some embodiments, the gelling agent or the viscosity modifying agent is also a bulking agent.

Suitable alcohols for use with the sanitizers of the present disclosure can include any water-soluble alcohol known in the art. In some embodiments, the alcohol is a short chain alcohol. Non-limiting examples of suitable alcohols include methanol, ethanol, n-propanol, isopropyl alcohol, butanol, t-butanol, 2-butanol, pentanol, hexanol, or combinations thereof. In certain embodiments, the alcohol is ethanol, isopropyl alcohol, or combinations thereof. In certain embodiments, the alcohol is ethanol. In one embodiment, the alcohol is a specially denatured alcohol, such as SD alcohol 40B.

In some embodiments, the sanitizing compositions of the present disclosure comprise alcohol in an amount of from about 20% to about 95% (by weight of the sanitizer). In some embodiments, the sanitizing compositions of the present disclosure comprise an alcohol in an amount of from about 25% to about 95%. In some embodiments, the sanitizing compositions of the present disclosure comprise an alcohol in an amount of from about 30% to about 95%. In some embodiments, the sanitizing compositions of the present disclosure comprise an alcohol in an amount of from about 35% to about 95%. In some embodiments, the sanitizing compositions of the present disclosure comprise an alcohol in an amount of from about 40% to about 95%. In some embodiments, the sanitizing compositions of the present disclosure comprise an alcohol in an amount of from about 45% to about 95%. In some embodiments, the sanitizing compositions of the present disclosure comprise an alcohol in an amount of from about 50% to about 95%. In some embodiments, the sanitizing compositions of the present disclosure comprise an alcohol in an amount of from about 55% to about 95%. In some embodiments, the sanitizing compositions of the present disclosure comprise an alcohol in an amount of from about 60% to about 95%. In some embodiments, the sanitizing compositions of the present disclosure comprise an alcohol in an amount of from about 65% to about 95%. In some embodiments, the sanitizing compositions of the present disclosure comprise an alcohol in an amount of from about 70% to about 95%. In some embodiments, the sanitizing compositions of the present disclosure comprise an alcohol in an amount of from about 75% to about 95%. In some embodiments, the sanitizing compositions of the present disclosure comprise an alcohol in an amount of from about 80% to about 95%. In some embodiments, the sanitizing compositions of the present disclosure comprise an alcohol in an amount of from about 85% to about 95%. In some embodiments, the sanitizing compositions of the present disclosure comprise an alcohol in an amount of from about 90% to about 95%.

In some embodiments, the sanitizing compositions of the present disclosure comprise an alcohol in an amount of from about 20% to about 90%. In some embodiments, the sanitizing compositions of the present disclosure comprise an alcohol in an amount of from about 25% to about 90%. In some embodiments, the sanitizing compositions of the present disclosure comprise an alcohol in an amount of from about 30% to about 90%. In some embodiments, the sanitizing compositions of the present disclosure comprise an alcohol in an amount of from about 35% to about 90%. In some embodiments, the sanitizing compositions of the present disclosure comprise an alcohol in an amount of from about 40% to about 90%. In some embodiments, the sanitizing compositions of the present disclosure comprise an alcohol in an amount of from about 45% to about 90%. In some embodiments, the sanitizing compositions of the present disclosure comprise an alcohol in an amount of from about 50% to about 90%. In some embodiments, the sanitizing compositions of the present disclosure comprise an alcohol in an amount of from about 55% to about 90%. In some embodiments, the sanitizing compositions of the present disclosure comprise an alcohol in an amount of from about 60% to about 90%. In some embodiments, the sanitizing compositions of the present disclosure comprise an alcohol in an amount of from about 65% to about 90%. In some embodiments, the sanitizing compositions of the present disclosure comprise an alcohol in an amount of from about 70% to about 90%. In some embodiments, the sanitizing compositions of the present disclosure comprise an alcohol in an amount of from about 75% to about 90%. In some embodiments, the sanitizing compositions of the present disclosure comprise an alcohol in an amount of from about 80% to about 90%. In some embodiments, the sanitizing compositions of the present disclosure comprise an alcohol in an amount of from about 85% to about 90%.

In some embodiments, the sanitizing compositions of the present disclosure comprise an alcohol in an amount of from about 20% to about 85%. In some embodiments, the sanitizing compositions of the present disclosure comprise an alcohol in an amount of from about 25% to about 85%. In some embodiments, the sanitizing compositions of the present disclosure comprise an alcohol in an amount of from about 30% to about 85%. In some embodiments, the sanitizing compositions of the present disclosure comprise an alcohol in an amount of from about 35% to about 85%. In some embodiments, the sanitizing compositions of the present disclosure comprise an alcohol in an amount of from about 40% to about 85%. In some embodiments, the sanitizing compositions of the present disclosure comprise an alcohol in an amount of from about 45% to about 85%. In some embodiments, the sanitizing compositions of the present disclosure comprise an alcohol in an amount of from about 50% to about 85%. In some embodiments, the sanitizing compositions of the present disclosure comprise an alcohol in an amount of from about 55% to about 85%. In some embodiments, the sanitizing compositions of the present disclosure comprise an alcohol in an amount of from about 60% to about 85%. In some embodiments, the sanitizing compositions of the present disclosure comprise an alcohol in an amount of from about 65% to about 85%. In some embodiments, the sanitizing compositions of the present disclosure comprise an alcohol in an amount of from about 70% to about 85%. In some embodiments, the sanitizing compositions of the present disclosure comprise an alcohol in an amount of from about 75% to about 85%. In some embodiments, the sanitizing compositions of the present disclosure comprise an alcohol in an amount of from about 80% to about 85%.

In some embodiments, the sanitizing compositions of the present disclosure comprise an alcohol in an amount of from about 20% to about 80%. In some embodiments, the sanitizing compositions of the present disclosure comprise an alcohol in an amount of from about 25% to about 80%. In some embodiments, the sanitizing compositions of the present disclosure comprise an alcohol in an amount of from about 30% to about 80%. In some embodiments, the sanitizing compositions of the present disclosure comprise an alcohol in an amount of from about 35% to about 80%. In some embodiments, the sanitizing compositions of the present disclosure comprise an alcohol in an amount of from about 40% to about 80%. In some embodiments, the sanitizing compositions of the present disclosure comprise an alcohol in an amount of from about 45% to about 80%. In some embodiments, the sanitizing compositions of the present disclosure comprise an alcohol in an amount of from about 50% to about 80%. In some embodiments, the sanitizing compositions of the present disclosure comprise an alcohol in an amount of from about 55% to about 80%. In some embodiments, the sanitizing compositions of the present disclosure comprise an alcohol in an amount of from about 60% to about 80%. In some embodiments, the sanitizing compositions of the present disclosure comprise an alcohol in an amount of from about 65% to about 80%. In some embodiments, the sanitizing compositions of the present disclosure comprise an alcohol in an amount of from about 70% to about 80%. In some embodiments, the sanitizing compositions of the present disclosure comprise an alcohol in an amount of from about 75% to about 80%.

In some embodiments, the sanitizing compositions of the present disclosure comprise an alcohol in an amount of from about 20% to about 75%. In some embodiments, the sanitizing compositions of the present disclosure comprise an alcohol in an amount of from about 25% to about 75%. In some embodiments, the sanitizing compositions of the present disclosure comprise an alcohol in an amount of from about 30% to about 75%. In some embodiments, the sanitizing compositions of the present disclosure comprise an alcohol in an amount of from about 35% to about 75%. In some embodiments, the sanitizing compositions of the present disclosure comprise an alcohol in an amount of from about 40% to about 75%. In some embodiments, the sanitizing compositions of the present disclosure comprise an alcohol in an amount of from about 45% to about 75%. In some embodiments, the sanitizing compositions of the present disclosure comprise an alcohol in an amount of from about 50% to about 75%. In some embodiments, the sanitizing compositions of the present disclosure comprise an alcohol in an amount of from about 55% to about 75%. In some embodiments, the sanitizing compositions of the present disclosure comprise an alcohol in an amount of from about 60% to about 75%. In some embodiments, the sanitizing compositions of the present disclosure comprise an alcohol in an amount of from about 65% to about 75%. In some embodiments, the sanitizing compositions of the present disclosure comprise an alcohol in an amount of from about 70% to about 75%.

In some embodiments, the sanitizing compositions of the present disclosure comprise an alcohol in an amount of from about 20% to about 70%. In some embodiments, the sanitizing compositions of the present disclosure comprise an alcohol in an amount of from about 25% to about 70%. In some embodiments, the sanitizing compositions of the present disclosure comprise an alcohol in an amount of from about 30% to about 70%. In some embodiments, the sanitizing compositions of the present disclosure comprise an alcohol in an amount of from about 35% to about 70%. In some embodiments, the sanitizing compositions of the present disclosure comprise an alcohol in an amount of from about 40% to about 70%. In some embodiments, the sanitizing compositions of the present disclosure comprise an alcohol in an amount of from about 45% to about 70%. In some embodiments, the sanitizing compositions of the present disclosure comprise an alcohol in an amount of from about 50% to about 70%. In some embodiments, the sanitizing compositions of the present disclosure comprise an alcohol in an amount of from about 55% to about 70%. In some embodiments, the sanitizing compositions of the present disclosure comprise an alcohol in an amount of from about 60% to about 70%. In some embodiments, the sanitizing compositions of the present disclosure comprise an alcohol in an amount of from about 65% to about 70%.

In some embodiments, the sanitizing compositions of the present disclosure comprise an alcohol in an amount of from about 20% to about 65%. In some embodiments, the sanitizing compositions of the present disclosure comprise an alcohol in an amount of from about 25% to about 65%. In some embodiments, the sanitizing compositions of the present disclosure comprise an alcohol in an amount of from about 30% to about 65%. In some embodiments, the sanitizing compositions of the present disclosure comprise an alcohol in an amount of from about 35% to about 65%. In some embodiments, the sanitizing compositions of the present disclosure comprise an alcohol in an amount of from about 40% to about 65%. In some embodiments, the sanitizing compositions of the present disclosure comprise an alcohol in an amount of from about 45% to about 65%. In some embodiments, the sanitizing compositions of the present disclosure comprise an alcohol in an amount of from about 50% to about 65%. In some embodiments, the sanitizing compositions of the present disclosure comprise an alcohol in an amount of from about 55% to about 65%. In some embodiments, the sanitizing compositions of the present disclosure comprise an alcohol in an amount of from about 60% to about 65%.

In some embodiments, the sanitizing compositions of the present disclosure comprise an alcohol in an amount of from about 20% to about 60%. In some embodiments, the sanitizing compositions of the present disclosure comprise an alcohol in an amount of from about 25% to about 60%. In some embodiments, the sanitizing compositions of the present disclosure comprise an alcohol in an amount of from about 30% to about 60%. In some embodiments, the sanitizing compositions of the present disclosure comprise an alcohol in an amount of from about 35% to about 60%. In some embodiments, the sanitizing compositions of the present disclosure comprise an alcohol in an amount of from about 40% to about 60%. In some embodiments, the sanitizing compositions of the present disclosure comprise an alcohol in an amount of from about 45% to about 60%. In some embodiments, the sanitizing compositions of the present disclosure comprise an alcohol in an amount of from about 50% to about 60%. In some embodiments, the sanitizing compositions of the present disclosure comprise an alcohol in an amount of from about 55% to about 60%.

In some embodiments, the sanitizing compositions of the present disclosure comprise an alcohol in an amount of from about 20% to about 55%. In some embodiments, the sanitizing compositions of the present disclosure comprise an alcohol in an amount of from about 25% to about 55%. In some embodiments, the sanitizing compositions of the present disclosure comprise an alcohol in an amount of from about 30% to about 55%. In some embodiments, the sanitizing compositions of the present disclosure comprise an alcohol in an amount of from about 35% to about 55%. In some embodiments, the sanitizing compositions of the present disclosure comprise an alcohol in an amount of from about 40% to about 55%. In some embodiments, the sanitizing compositions of the present disclosure comprise an alcohol in an amount of from about 45% to about 55%. In some embodiments, the sanitizing compositions of the present disclosure comprise an alcohol in an amount of from about 50% to about 55%.

In some embodiments, the sanitizing compositions of the present disclosure comprise an alcohol in an amount of from about 20% to about 50%. In some embodiments, the sanitizing compositions of the present disclosure comprise an alcohol in an amount of from about 25% to about 50%. In some embodiments, the sanitizing compositions of the present disclosure comprise an alcohol in an amount of from about 30% to about 50%. In some embodiments, the sanitizing compositions of the present disclosure comprise an alcohol in an amount of from about 35% to about 50%. In some embodiments, the sanitizing compositions of the present disclosure comprise an alcohol in an amount of from about 40% to about 50%. In some embodiments, the sanitizing compositions of the present disclosure comprise an alcohol in an amount of from about 45% to about 50%.

In some embodiments, the sanitizing compositions of the present disclosure comprise an alcohol in an amount of about 70%.

In addition to the alcohol, in certain embodiments, the sanitizing compositions of the present disclosure may optionally further comprise other disinfectants, antimicrobial agents, and/or sporicides that contribute to the antimicrobial effect of the sanitizer.

In some embodiments, the sanitizers of the present disclosure further comprise one or more moisturizers or other skin protectants, such as an emollient and/or a silicone. Suitable silicone materials include, for example, a silicone surfactant, a volatile silicone oil, a non-volatile silicone oil, or combinations thereof. More particularly, the silicone material may be, for example, dimethicone, cyclomethicone, polyalkylsiloxanes, polyarylsiloxanes, polyalkylarylsiloxanes, polysiloxane gums, polyether siloxane copolymers, and combinations thereof. Exemplary silicone and silicone derivatives also include branched or linear cyclical silicone or silicone derivatives, cyclomethicone, dimethicone polysiloxane, dimethiconol, polysiloxanes, polysiloxane copolymers, polyalkyl aryl silanes, polyaryl siloxanes, polyalkyl siloxanes, polyalkyl aryl silanes, polysiloxane copolymers, alkyl dimethicones, alkyl methicones, alkyldimethicone copolyols, phenyl silicones, alkyl trimethylsilanes, cyclopentasiloxane, dimethicone crosspolymer, trisiloxane, and combinations thereof. Examples of silicones include low viscosity dimethicone, phenyl trimethicione, and silicone fluid DC 345 (available from Dow Corning).

In some embodiments, the emulsifiers have a hydrophilic/lipophilic balance (HLB) of from 2 to 25, and behave as water-in-oil emulsifiers or oil-in-water emulsifiers. Suitable carbon based emulsifiers include sorbitan laurate, sorbitan palmitate, sorbitan stearate, sorbitan oleate, sorbitan sesquioleate, sorbitan trioleate, sorbitan isostearate, isoceteth-20, PEG-40 sorbitan peroleate, PEG-40 hydrogenated castor oil, laureth-4, laureth-23, ceteth-2, ceteth-10, ceteth-20, steareth-2, steareth-10, steareth-20, oleth-2 oleth-10, oleth-20, steareth-21, laureth-23, PEG-8 stearate, PEG-20 stearate, glyceryl stearate, hydrogenated vegetable glycerides phosphate, polyglyceryl-3-diisostearate, polyglyceryl-4 oleate, poloxamer 335, or combinations thereof.

In addition to acting as a disinfectant, the sanitizing compositions of the present disclosure may also be formulated to provide additional skin health benefits to a user, such as soothing, anti-irritation, and moisturization effects. In some embodiments, the sanitizer contains additional moisturizers such as humectants, carriers, dyes, fragrances, chelating agents, rheology modifiers, thickeners, pH modifiers, and various other optional components.

In some embodiments, the more concentrated the alcohol in the sanitizer, the more potent the antimicrobial effect. However, increasing the alcohol concentration may have the effect of increasing the level of skin irritancy for certain users of the sanitizer.

In certain embodiments, the sanitizing compositions further comprise a humectant. Humectant present in the sanitizer compositions may advantageously be deposited on the skin upon use of the sanitizer, thus helping to maintain lipids and essential oils present in the skin. Certain examples of suitable humectants include glycerin, glycerin derivatives, sodium hyaluronate, hyaluronic acid, betaine, amino acids, glycosaminoglycans, honey, sorbitol, glycols such as propylene glycol, polyols, sugars, hydrogenated starch hydrolysates, salts of PCA such as sodium PCA, lactic acid, lactates, urea, and the like. In some embodiments, the humectant is glycerin.

In some embodiments, the sanitizing compositions of the present disclosure comprise one or more humectants in an amount of from about 0.010% to about 10% (by weight of the sanitizer). In some embodiments, the sanitizing compositions of the present disclosure comprise one or more humectants in an amount of from about 0.05% to about 10%. In some embodiments, the sanitizing compositions of the present disclosure comprise one or more humectants in an amount of from about 0.10% to about 10%. In some embodiments, the sanitizing compositions of the present disclosure comprise one or more humectants in an amount of from about 0.5% to about 10%. In some embodiments, the sanitizing compositions of the present disclosure comprise one or more humectants in an amount of from about 1.0% to about 10%. In some embodiments, the sanitizing compositions of the present disclosure comprise one or more humectants in an amount of from about 1.5% to about 10%. In some embodiments, the sanitizing compositions of the present disclosure comprise one or more humectants in an amount of from about 2.0% to about 10%. In some embodiments, the sanitizing compositions of the present disclosure comprise one or more humectants in an amount of from about 2.5% to about 10%. In some embodiments, the sanitizing compositions of the present disclosure comprise one or more humectants in an amount of from about 3.0% to about 10%. In some embodiments, the sanitizing compositions of the present disclosure comprise one or more humectants in an amount of from about 3.5% to about 10%. In some embodiments, the sanitizing compositions of the present disclosure comprise one or more humectants in an amount of from about 4.0% to about 10%. In some embodiments, the sanitizing compositions of the present disclosure comprise one or more humectants in an amount of from about 4.5% to about 10%. In some embodiments, the sanitizing compositions of the present disclosure comprise one or more humectants in an amount of from about 5.0% to about 10%. In some embodiments, the sanitizing compositions of the present disclosure comprise one or more humectants in an amount of from about 5.5% to about 10%. In some embodiments, the sanitizing compositions of the present disclosure comprise one or more humectants in an amount of from about 6.0% to about 10%. In some embodiments, the sanitizing compositions of the present disclosure comprise one or more humectants in an amount of from about 6.5% to about 10%. In some embodiments, the sanitizing compositions of the present disclosure comprise one or more humectants in an amount of from about 7.0% to about 10%. In some embodiments, the sanitizing compositions of the present disclosure comprise one or more humectants in an amount of from about 7.5% to about 10%. In some embodiments, the sanitizing compositions of the present disclosure comprise one or more humectants in an amount of from about 8.0% to about 10%. In some embodiments, the sanitizing compositions of the present disclosure comprise one or more humectants in an amount of from about 8.5% to about 10%. In some embodiments, the sanitizing compositions of the present disclosure comprise one or more humectants in an amount of from about 9.0% to about 10%. In some embodiments, the sanitizing compositions of the present disclosure comprise one or more humectants in an amount of from about 9.5% to about 10%.

In some embodiments, the sanitizing compositions of the present disclosure comprise one or more humectants in an amount of from about 0.01% to about 9.5% (by weight of the sanitizer). In some embodiments, the sanitizing compositions of the present disclosure comprise one or more humectants in an amount of from about 0.05% to about 9.5%. In some embodiments, the sanitizing compositions of the present disclosure comprise one or more humectants in an amount of from about 0.1% to about 9.5%. In some embodiments, the sanitizing compositions of the present disclosure comprise one or more humectants in an amount of from about 0.5% to about 9.5%. In some embodiments, the sanitizing compositions of the present disclosure comprise one or more humectants in an amount of from about 1.0% to about 9.5%. In some embodiments, the sanitizing compositions of the present disclosure comprise one or more humectants in an amount of from about 1.5% to about 9.5%. In some embodiments, the sanitizing compositions of the present disclosure comprise one or more humectants in an amount of from about 2.0% to about 9.5%. In some embodiments, the sanitizing compositions of the present disclosure comprise one or more humectants in an amount of from about 2.5% to about 9.5%. In some embodiments, the sanitizing compositions of the present disclosure comprise one or more humectants in an amount of from about 3.0% to about 9.5%. In some embodiments, the sanitizing compositions of the present disclosure comprise one or more humectants in an amount of from about 3.5% to about 9.5%. In some embodiments, the sanitizing compositions of the present disclosure comprise one or more humectants in an amount of from about 4.0% to about 9.5%. In some embodiments, the sanitizing compositions of the present disclosure comprise one or more humectants in an amount of from about 4.5% to about 9.5%. In some embodiments, the sanitizing compositions of the present disclosure comprise one or more humectants in an amount of from about 5.0% to about 9.5%. In some embodiments, the sanitizing compositions of the present disclosure comprise one or more humectants in an amount of from about 5.5% to about 9.5%. In some embodiments, the sanitizing compositions of the present disclosure comprise one or more humectants in an amount of from about 6.0% to about 9.5%. In some embodiments, the sanitizing compositions of the present disclosure comprise one or more humectants in an amount of from about 6.5% to about 9.5%. In some embodiments, the sanitizing compositions of the present disclosure comprise one or more humectants in an amount of from about 7.0% to about 9.5%. In some embodiments, the sanitizing compositions of the present disclosure comprise one or more humectants in an amount of from about 7.5% to about 9.5%. In some embodiments, the sanitizing compositions of the present disclosure comprise one or more humectants in an amount of from about 8.0% to about 9.5%. In some embodiments, the sanitizing compositions of the present disclosure comprise one or more humectants in an amount of from about 8.5% to about 9.5%. In some embodiments, the sanitizing compositions of the present disclosure comprise one or more humectants in an amount of from about 9.0% to about 9.5%.

In some embodiments, the sanitizing compositions of the present disclosure comprise one or more humectants in an amount of from about 0.01% to about 9.0% (by weight of the sanitizer). In some embodiments, the sanitizing compositions of the present disclosure comprise one or more humectants in an amount of from about 0.05% to about 9.0%. In some embodiments, the sanitizing compositions of the present disclosure comprise one or more humectants in an amount of from about 0.1% to about 9.0%. In some embodiments, the sanitizing compositions of the present disclosure comprise one or more humectants in an amount of from about 0.5% to about 9.0%. In some embodiments, the sanitizing compositions of the present disclosure comprise one or more humectants in an amount of from about 1.0% to about 9.0%. In some embodiments, the sanitizing compositions of the present disclosure comprise one or more humectants in an amount of from about 1.5% to about 9.0%. In some embodiments, the sanitizing compositions of the present disclosure comprise one or more humectants in an amount of from about 2.0% to about 9.0%. In some embodiments, the sanitizing compositions of the present disclosure comprise one or more humectants in an amount of from about 2.5% to about 9.0%. In some embodiments, the sanitizing compositions of the present disclosure comprise one or more humectants in an amount of from about 3.0% to about 9.0%. In some embodiments, the sanitizing compositions of the present disclosure comprise one or more humectants in an amount of from about 3.5% to about 9.0%. In some embodiments, the sanitizing compositions of the present disclosure comprise one or more humectants in an amount of from about 4.0% to about 9.0%. In some embodiments, the sanitizing compositions of the present disclosure comprise one or more humectants in an amount of from about 4.5% to about 9.0%. In some embodiments, the sanitizing compositions of the present disclosure comprise one or more humectants in an amount of from about 5.0% to about 9.0%. In some embodiments, the sanitizing compositions of the present disclosure comprise one or more humectants in an amount of from about 5.5% to about 9.0%. In some embodiments, the sanitizing compositions of the present disclosure comprise one or more humectants in an amount of from about 6.0% to about 9.0%. In some embodiments, the sanitizing compositions of the present disclosure comprise one or more humectants in an amount of from about 6.5% to about 9.0%. In some embodiments, the sanitizing compositions of the present disclosure comprise one or more humectants in an amount of from about 7.0% to about 9.0%. In some embodiments, the sanitizing compositions of the present disclosure comprise one or more humectants in an amount of from about 7.5% to about 9.0%. In some embodiments, the sanitizing compositions of the present disclosure comprise one or more humectants in an amount of from about 8.0% to about 9.0%. In some embodiments, the sanitizing compositions of the present disclosure comprise one or more humectants in an amount of from about 8.5% to about 9.0%.

In some embodiments, the sanitizing compositions of the present disclosure comprise one or more humectants in an amount of from about 0.01% to about 8.5% (by weight of the sanitizer). In some embodiments, the sanitizing compositions of the present disclosure comprise one or more humectants in an amount of from about 0.05% to about 8.5%. In some embodiments, the sanitizing compositions of the present disclosure comprise one or more humectants in an amount of from about 0.1% to about 8.5%. In some embodiments, the sanitizing compositions of the present disclosure comprise one or more humectants in an amount of from about 0.5% to about 8.5%. In some embodiments, the sanitizing compositions of the present disclosure comprise one or more humectants in an amount of from about 1.0% to about 8.5%. In some embodiments, the sanitizing compositions of the present disclosure comprise one or more humectants in an amount of from about 1.5% to about 8.5%. In some embodiments, the sanitizing compositions of the present disclosure comprise one or more humectants in an amount of from about 2.0% to about 8.5%. In some embodiments, the sanitizing compositions of the present disclosure comprise one or more humectants in an amount of from about 2.5% to about 8.5%. In some embodiments, the sanitizing compositions of the present disclosure comprise one or more humectants in an amount of from about 3.0% to about 8.5%. In some embodiments, the sanitizing compositions of the present disclosure comprise one or more humectants in an amount of from about 3.5% to about 8.5%. In some embodiments, the sanitizing compositions of the present disclosure comprise one or more humectants in an amount of from about 4.0% to about 8.5%. In some embodiments, the sanitizing compositions of the present disclosure comprise one or more humectants in an amount of from about 4.5% to about 8.5%. In some embodiments, the sanitizing compositions of the present disclosure comprise one or more humectants in an amount of from about 5.0% to about 8.5%. In some embodiments, the sanitizing compositions of the present disclosure comprise one or more humectants in an amount of from about 5.5% to about 8.5%. In some embodiments, the sanitizing compositions of the present disclosure comprise one or more humectants in an amount of from about 6.0% to about 8.5%. In some embodiments, the sanitizing compositions of the present disclosure comprise one or more humectants in an amount of from about 6.5% to about 8.5%. In some embodiments, the sanitizing compositions of the present disclosure comprise one or more humectants in an amount of from about 7.0% to about 8.5%. In some embodiments, the sanitizing compositions of the present disclosure comprise one or more humectants in an amount of from about 7.5% to about 8.5%. In some embodiments, the sanitizing compositions of the present disclosure comprise one or more humectants in an amount of from about 8.0% to about 8.5%.

In some embodiments, the sanitizing compositions of the present disclosure comprise one or more humectants in an amount of from about 0.01% to about 8.0% (by weight of the sanitizer). In some embodiments, the sanitizing compositions of the present disclosure comprise one or more humectants in an amount of from about 0.05% to about 8.0%. In some embodiments, the sanitizing compositions of the present disclosure comprise one or more humectants in an amount of from about 0.10% to about 8.0%. In some embodiments, the sanitizing compositions of the present disclosure comprise one or more humectants in an amount of from about 0.5% to about 8.0%. In some embodiments, the sanitizing compositions of the present disclosure comprise one or more humectants in an amount of from about 1.0% to about 8.0%. In some embodiments, the sanitizing compositions of the present disclosure comprise one or more humectants in an amount of from about 1.5% to about 8.0%. In some embodiments, the sanitizing compositions of the present disclosure comprise one or more humectants in an amount of from about 2.0% to about 8.0%. In some embodiments, the sanitizing compositions of the present disclosure comprise one or more humectants in an amount of from about 2.5% to about 8.0%. In some embodiments, the sanitizing compositions of the present disclosure comprise one or more humectants in an amount of from about 3.0% to about 8.0%. In some embodiments, the sanitizing compositions of the present disclosure comprise one or more humectants in an amount of from about 3.5% to about 8.0%. In some embodiments, the sanitizing compositions of the present disclosure comprise one or more humectants in an amount of from about 4.0% to about 8.0%. In some embodiments, the sanitizing compositions of the present disclosure comprise one or more humectants in an amount of from about 4.5% to about 8.0%. In some embodiments, the sanitizing compositions of the present disclosure comprise one or more humectants in an amount of from about 5.0% to about 8.0%. In some embodiments, the sanitizing compositions of the present disclosure comprise one or more humectants in an amount of from about 5.5% to about 8.0%. In some embodiments, the sanitizing compositions of the present disclosure comprise one or more humectants in an amount of from about 6.0% to about 8.0%. In some embodiments, the sanitizing compositions of the present disclosure comprise one or more humectants in an amount of from about 6.5% to about 8.0%. In some embodiments, the sanitizing compositions of the present disclosure comprise one or more humectants in an amount of from about 7.0% to about 8.0%. In some embodiments, the sanitizing compositions of the present disclosure comprise one or more humectants in an amount of from about 7.5% to about 8.0%.

In some embodiments, the sanitizing compositions of the present disclosure comprise one or more humectants in an amount of from about 0.01% to about 7.5% (by weight of the sanitizer). In some embodiments, the sanitizing compositions of the present disclosure comprise one or more humectants in an amount of from about 0.05% to about 7.5%. In some embodiments, the sanitizing compositions of the present disclosure comprise one or more humectants in an amount of from about 0.1% to about 7.5%. In some embodiments, the sanitizing compositions of the present disclosure comprise one or more humectants in an amount of from about 0.5% to about 7.5%. In some embodiments, the sanitizing compositions of the present disclosure comprise one or more humectants in an amount of from about 1.0% to about 7.5%. In some embodiments, the sanitizing compositions of the present disclosure comprise one or more humectants in an amount of from about 1.5% to about 7.5%. In some embodiments, the sanitizing compositions of the present disclosure comprise one or more humectants in an amount of from about 2.0% to about 7.5%. In some embodiments, the sanitizing compositions of the present disclosure comprise one or more humectants in an amount of from about 2.5% to about 7.5%. In some embodiments, the sanitizing compositions of the present disclosure comprise one or more humectants in an amount of from about 3.0% to about 7.5%. In some embodiments, the sanitizing compositions of the present disclosure comprise one or more humectants in an amount of from about 3.5% to about 7.5%. In some embodiments, the sanitizing compositions of the present disclosure comprise one or more humectants in an amount of from about 4.0% to about 7.5%. In some embodiments, the sanitizing compositions of the present disclosure comprise one or more humectants in an amount of from about 4.5% to about 7.5%. In some embodiments, the sanitizing compositions of the present disclosure comprise one or more humectants in an amount of from about 5.0% to about 7.5%. In some embodiments, the sanitizing compositions of the present disclosure comprise one or more humectants in an amount of from about 5.5% to about 7.5%. In some embodiments, the sanitizing compositions of the present disclosure comprise one or more humectants in an amount of from about 6.0% to about 7.5%. In some embodiments, the sanitizing compositions of the present disclosure comprise one or more humectants in an amount of from about 6.5% to about 7.5%. In some embodiments, the sanitizing compositions of the present disclosure comprise one or more humectants in an amount of from about 7.0% to about 7.5%.

In some embodiments, the sanitizing compositions of the present disclosure comprise one or more humectants in an amount of from about 0.01% to about 7.0% (by weight of the sanitizer). In some embodiments, the sanitizing compositions of the present disclosure comprise one or more humectants in an amount of from about 0.05% to about 7.0%. In some embodiments, the sanitizing compositions of the present disclosure comprise one or more humectants in an amount of from about 0.10% to about 7.0%. In some embodiments, the sanitizing compositions of the present disclosure comprise one or more humectants in an amount of from about 0.5% to about 7.0%. In some embodiments, the sanitizing compositions of the present disclosure comprise one or more humectants in an amount of from about 1.0% to about 7.0%. In some embodiments, the sanitizing compositions of the present disclosure comprise one or more humectants in an amount of from about 1.5% to about 7.0%. In some embodiments, the sanitizing compositions of the present disclosure comprise one or more humectants in an amount of from about 2.0% to about 7.0%. In some embodiments, the sanitizing compositions of the present disclosure comprise one or more humectants in an amount of from about 2.5% to about 7.0%. In some embodiments, the sanitizing compositions of the present disclosure comprise one or more humectants in an amount of from about 3.0% to about 7.0%. In some embodiments, the sanitizing compositions of the present disclosure comprise one or more humectants in an amount of from about 3.5% to about 7.0%. In some embodiments, the sanitizing compositions of the present disclosure comprise one or more humectants in an amount of from about 4.0% to about 7.0%. In some embodiments, the sanitizing compositions of the present disclosure comprise one or more humectants in an amount of from about 4.5% to about 7.0%. In some embodiments, the sanitizing compositions of the present disclosure comprise one or more humectants in an amount of from about 5.0% to about 7.0%. In some embodiments, the sanitizing compositions of the present disclosure comprise one or more humectants in an amount of from about 5.5% to about 7.0%. In some embodiments, the sanitizing compositions of the present disclosure comprise one or more humectants in an amount of from about 6.0% to about 7.0%. In some embodiments, the sanitizing compositions of the present disclosure comprise one or more humectants in an amount of from about 6.5% to about 7.0%.

In some embodiments, the sanitizing compositions of the present disclosure comprise one or more humectants in an amount of from about 0.01% to about 6.5% (by weight of the sanitizer). In some embodiments, the sanitizing compositions of the present disclosure comprise one or more humectants in an amount of from about 0.05% to about 6.5%. In some embodiments, the sanitizing compositions of the present disclosure comprise one or more humectants in an amount of from about 0.1% to about 6.5%. In some embodiments, the sanitizing compositions of the present disclosure comprise one or more humectants in an amount of from about 0.5% to about 6.5%. In some embodiments, the sanitizing compositions of the present disclosure comprise one or more humectants in an amount of from about 1.0% to about 6.5%. In some embodiments, the sanitizing compositions of the present disclosure comprise one or more humectants in an amount of from about 1.5% to about 6.5%. In some embodiments, the sanitizing compositions of the present disclosure comprise one or more humectants in an amount of from about 2.0% to about 6.5%. In some embodiments, the sanitizing compositions of the present disclosure comprise one or more humectants in an amount of from about 2.5% to about 6.5%. In some embodiments, the sanitizing compositions of the present disclosure comprise one or more humectants in an amount of from about 3.0% to about 6.5%. In some embodiments, the sanitizing compositions of the present disclosure comprise one or more humectants in an amount of from about 3.5% to about 6.5%. In some embodiments, the sanitizing compositions of the present disclosure comprise one or more humectants in an amount of from about 4.0% to about 6.5%. In some embodiments, the sanitizing compositions of the present disclosure comprise one or more humectants in an amount of from about 4.5% to about 6.5%. In some embodiments, the sanitizing compositions of the present disclosure comprise one or more humectants in an amount of from about 5.0% to about 6.5%. In some embodiments, the sanitizing compositions of the present disclosure comprise one or more humectants in an amount of from about 5.5% to about 6.5%. In some embodiments, the sanitizing compositions of the present disclosure comprise one or more humectants in an amount of from about 6.0% to about 6.5%.

In some embodiments, the sanitizing compositions of the present disclosure comprise one or more humectants in an amount of from about 0.01% to about 6.0% (by weight of the sanitizer). In some embodiments, the sanitizing compositions of the present disclosure comprise one or more humectants in an amount of from about 0.05% to about 6.0%. In some embodiments, the sanitizing compositions of the present disclosure comprise one or more humectants in an amount of from about 0.1% to about 6.0%. In some embodiments, the sanitizing compositions of the present disclosure comprise one or more humectants in an amount of from about 0.5% to about 6.0%. In some embodiments, the sanitizing compositions of the present disclosure comprise one or more humectants in an amount of from about 1.0% to about 6.0%. In some embodiments, the sanitizing compositions of the present disclosure comprise one or more humectants in an amount of from about 1.5% to about 6.0%. In some embodiments, the sanitizing compositions of the present disclosure comprise one or more humectants in an amount of from about 2.0% to about 6.0%. In some embodiments, the sanitizing compositions of the present disclosure comprise one or more humectants in an amount of from about 2.5% to about 6.0%. In some embodiments, the sanitizing compositions of the present disclosure comprise one or more humectants in an amount of from about 3.0% to about 6.0%. In some embodiments, the sanitizing compositions of the present disclosure comprise one or more humectants in an amount of from about 3.5% to about 6.0%. In some embodiments, the sanitizing compositions of the present disclosure comprise one or more humectants in an amount of from about 4.0% to about 6.0%. In some embodiments, the sanitizing compositions of the present disclosure comprise one or more humectants in an amount of from about 4.5% to about 6.0%. In some embodiments, the sanitizing compositions of the present disclosure comprise one or more humectants in an amount of from about 5.0% to about 6.0%. In some embodiments, the sanitizing compositions of the present disclosure comprise one or more humectants in an amount of from about 5.5% to about 6.0%.

In some embodiments, the sanitizing compositions of the present disclosure comprise one or more humectants in an amount of from about 0.01% to about 5.5% (by weight of the sanitizer). In some embodiments, the sanitizing compositions of the present disclosure comprise one or more humectants in an amount of from about 0.05% to about 5.5%. In some embodiments, the sanitizing compositions of the present disclosure comprise one or more humectants in an amount of from about 0.1% to about 5.5%. In some embodiments, the sanitizing compositions of the present disclosure comprise one or more humectants in an amount of from about 0.5% to about 5.5%. In some embodiments, the sanitizing compositions of the present disclosure comprise one or more humectants in an amount of from about 1.0% to about 5.5%. In some embodiments, the sanitizing compositions of the present disclosure comprise one or more humectants in an amount of from about 1.5% to about 5.5%. In some embodiments, the sanitizing compositions of the present disclosure comprise one or more humectants in an amount of from about 2.0% to about 5.5%. In some embodiments, the sanitizing compositions of the present disclosure comprise one or more humectants in an amount of from about 2.5% to about 5.5%. In some embodiments, the sanitizing compositions of the present disclosure comprise one or more humectants in an amount of from about 3.0% to about 5.5%. In some embodiments, the sanitizing compositions of the present disclosure comprise one or more humectants in an amount of from about 3.5% to about 5.5%. In some embodiments, the sanitizing compositions of the present disclosure comprise one or more humectants in an amount of from about 4.0% to about 5.5%. In some embodiments, the sanitizing compositions of the present disclosure comprise one or more humectants in an amount of from about 4.5% to about 5.5%.

In some embodiments, the sanitizing compositions of the present disclosure comprise one or more humectants in an amount of from about 0.010% to about 5.0% (by weight of the sanitizer). In some embodiments, the sanitizing compositions of the present disclosure comprise one or more humectants in an amount of from about 0.05% to about 5.0%. In some embodiments, the sanitizing compositions of the present disclosure comprise one or more humectants in an amount of from about 0.10% to about 5.0%. In some embodiments, the sanitizing compositions of the present disclosure comprise one or more humectants in an amount of from about 0.5% to about 5.0%. In some embodiments, the sanitizing compositions of the present disclosure comprise one or more humectants in an amount of from about 1.0% to about 5.0%. In some embodiments, the sanitizing compositions of the present disclosure comprise one or more humectants in an amount of from about 1.5% to about 5.0%. In some embodiments, the sanitizing compositions of the present disclosure comprise one or more humectants in an amount of from about 2.0% to about 5.0%. In some embodiments, the sanitizing compositions of the present disclosure comprise one or more humectants in an amount of from about 2.5% to about 5.0%. In some embodiments, the sanitizing compositions of the present disclosure comprise one or more humectants in an amount of from about 3.0% to about 5.0%. In some embodiments, the sanitizing compositions of the present disclosure comprise one or more humectants in an amount of from about 3.5% to about 5.0%. In some embodiments, the sanitizing compositions of the present disclosure comprise one or more humectants in an amount of from about 4.0% to about 5.0%. In some embodiments, the sanitizing compositions of the present disclosure comprise one or more humectants in an amount of from about 4.5% to about 5.0%.

In some embodiments, the sanitizing compositions of the present disclosure comprise one or more humectants in an amount of from about 0.01% to about 4.5% (by weight of the sanitizer). In some embodiments, the sanitizing compositions of the present disclosure comprise one or more humectants in an amount of from about 0.05% to about 4.5%. In some embodiments, the sanitizing compositions of the present disclosure comprise one or more humectants in an amount of from about 0.1% to about 4.5%. In some embodiments, the sanitizing compositions of the present disclosure comprise one or more humectants in an amount of from about 0.5% to about 4.5%. In some embodiments, the sanitizing compositions of the present disclosure comprise one or more humectants in an amount of from about 1.0% to about 4.5%. In some embodiments, the sanitizing compositions of the present disclosure comprise one or more humectants in an amount of from about 1.5% to about 4.5%. In some embodiments, the sanitizing compositions of the present disclosure comprise one or more humectants in an amount of from about 2.0% to about 4.5%. In some embodiments, the sanitizing compositions of the present disclosure comprise one or more humectants in an amount of from about 2.5% to about 4.5%. In some embodiments, the sanitizing compositions of the present disclosure comprise one or more humectants in an amount of from about 3.0% to about 4.5%. In some embodiments, the sanitizing compositions of the present disclosure comprise one or more humectants in an amount of from about 3.5% to about 4.5%. In some embodiments, the sanitizing compositions of the present disclosure comprise one or more humectants in an amount of from about 4.0% to about 4.5%.

In some embodiments, the sanitizing compositions of the present disclosure comprise one or more humectants in an amount of from about 0.010% to about 4.0% (by weight of the sanitizer). In some embodiments, the sanitizing compositions of the present disclosure comprise one or more humectants in an amount of from about 0.05% to about 4.0%. In some embodiments, the sanitizing compositions of the present disclosure comprise one or more humectants in an amount of from about 0.1% to about 4.0%. In some embodiments, the sanitizing compositions of the present disclosure comprise one or more humectants in an amount of from about 0.5% to about 4.0%. In some embodiments, the sanitizing compositions of the present disclosure comprise one or more humectants in an amount of from about 1.0% to about 4.0%. In some embodiments, the sanitizing compositions of the present disclosure comprise one or more humectants in an amount of from about 1.5% to about 4.0%. In some embodiments, the sanitizing compositions of the present disclosure comprise one or more humectants in an amount of from about 2.0% to about 4.0%. In some embodiments, the sanitizing compositions of the present disclosure comprise one or more humectants in an amount of from about 2.5% to about 4.0%. In some embodiments, the sanitizing compositions of the present disclosure comprise one or more humectants in an amount of from about 3.0% to about 4.0%. In some embodiments, the sanitizing compositions of the present disclosure comprise one or more humectants in an amount of from about 3.5% to about 4.0%.

In some embodiments, the sanitizing compositions of the present disclosure comprise one or more humectants in an amount of from about 0.01% to about 3.5% (by weight of the sanitizer). In some embodiments, the sanitizing compositions of the present disclosure comprise one or more humectants in an amount of from about 0.05% to about 3.5%. In some embodiments, the sanitizing compositions of the present disclosure comprise one or more humectants in an amount of from about 0.1% to about 3.5%. In some embodiments, the sanitizing compositions of the present disclosure comprise one or more humectants in an amount of from about 0.5% to about 3.5%. In some embodiments, the sanitizing compositions of the present disclosure comprise one or more humectants in an amount of from about 1.0% to about 3.5%. In some embodiments, the sanitizing compositions of the present disclosure comprise one or more humectants in an amount of from about 1.5% to about 3.5%. In some embodiments, the sanitizing compositions of the present disclosure comprise one or more humectants in an amount of from about 2.0% to about 3.5%. In some embodiments, the sanitizing compositions of the present disclosure comprise one or more humectants in an amount of from about 2.5% to about 3.5%. In some embodiments, the sanitizing compositions of the present disclosure comprise one or more humectants in an amount of from about 3.0% to about 3.5%.

In some embodiments, the sanitizing compositions of the present disclosure comprise one or more humectants in an amount of from about 0.010% to about 3.0% (by weight of the sanitizer). In some embodiments, the sanitizing compositions of the present disclosure comprise one or more humectants in an amount of from about 0.05% to about 3.0%. In some embodiments, the sanitizing compositions of the present disclosure comprise one or more humectants in an amount of from about 0.10% to about 3.0%. In some embodiments, the sanitizing compositions of the present disclosure comprise one or more humectants in an amount of from about 0.5% to about 3.0%. In some embodiments, the sanitizing compositions of the present disclosure comprise one or more humectants in an amount of from about 1.0% to about 3.0%. In some embodiments, the sanitizing compositions of the present disclosure comprise one or more humectants in an amount of from about 1.5% to about 3.0%. In some embodiments, the sanitizing compositions of the present disclosure comprise one or more humectants in an amount of from about 2.0% to about 3.0%. In some embodiments, the sanitizing compositions of the present disclosure comprise one or more humectants in an amount of from about 2.5% to about 3.0%.

In some embodiments, the sanitizing compositions of the present disclosure comprise one or more humectants in an amount of from about 0.01% to about 2.5% (by weight of the sanitizer). In some embodiments, the sanitizing compositions of the present disclosure comprise one or more humectants in an amount of from about 0.05% to about 2.5%. In some embodiments, the sanitizing compositions of the present disclosure comprise one or more humectants in an amount of from about 0.1% to about 2.5%. In some embodiments, the sanitizing compositions of the present disclosure comprise one or more humectants in an amount of from about 0.5% to about 2.5%. In some embodiments, the sanitizing compositions of the present disclosure comprise one or more humectants in an amount of from about 1.0% to about 2.5%. In some embodiments, the sanitizing compositions of the present disclosure comprise one or more humectants in an amount of from about 1.5% to about 2.5%. In some embodiments, the sanitizing compositions of the present disclosure comprise one or more humectants in an amount of from about 2.0% to about 2.5%.

In some embodiments, the sanitizing compositions of the present disclosure comprise one or more humectants in an amount of from about 0.010% to about 2.0% (by weight of the sanitizer). In some embodiments, the sanitizing compositions of the present disclosure comprise one or more humectants in an amount of from about 0.05% to about 2.0%. In some embodiments, the sanitizing compositions of the present disclosure comprise one or more humectants in an amount of from about 0.10% to about 2.0%. In some embodiments, the sanitizing compositions of the present disclosure comprise one or more humectants in an amount of from about 0.5% to about 2.0%. In some embodiments, the sanitizing compositions of the present disclosure comprise one or more humectants in an amount of from about 1.0% to about 2.0%. In some embodiments, the sanitizing compositions of the present disclosure comprise one or more humectants in an amount of from about 1.5% to about 2.0%.

In some embodiments, the sanitizing compositions of the present disclosure comprise one or more humectants in an amount of from about 0.01% to about 1.5% (by weight of the sanitizer). In some embodiments, the sanitizing compositions of the present disclosure comprise one or more humectants in an amount of from about 0.05% to about 1.5%. In some embodiments, the sanitizing compositions of the present disclosure comprise one or more humectants in an amount of from about 0.1% to about 1.5%. In some embodiments, the sanitizing compositions of the present disclosure comprise one or more humectants in an amount of from about 0.5% to about 1.5%. In some embodiments, the sanitizing compositions of the present disclosure comprise one or more humectants in an amount of from about 1.0% to about 1.5%.

In some embodiments, the sanitizing compositions of the present disclosure comprise one or more humectants in an amount of from about 0.010% to about 1.0% (by weight of the sanitizer). In some embodiments, the sanitizing compositions of the present disclosure comprise one or more humectants in an amount of from about 0.05% to about 1.0%. In some embodiments, the sanitizing compositions of the present disclosure comprise one or more humectants in an amount of from about 0.10% to about 1.0%. In some embodiments, the sanitizing compositions of the present disclosure comprise one or more humectants in an amount of from about 0.5% to about 1.0%.

In some embodiments, the sanitizing compositions of the present disclosure comprise one or more humectants in an amount of from about 0.01% to about 0.5% (by weight of the sanitizer). In some embodiments, the sanitizing compositions of the present disclosure comprise one or more humectants in an amount of from about 0.05% to about 0.5%. In some embodiments, the sanitizing compositions of the present disclosure comprise one or more humectants in an amount of from about 0.1% to about 0.5%.

In some embodiments, the sanitizing compositions of the present disclosure comprise one or more humectants in an amount of from about 0.010% to about 0.1% (by weight of the sanitizer). In some embodiments, the sanitizing compositions of the present disclosure comprise one or more humectants in an amount of from about 0.05% to about 0.10%.

The sanitizing compositions of the present disclosure may further comprise a carrier material such as water. In some embodiments, the water is present in the sanitizer compositions in an amount of from about 1% (by weight of the sanitizer) to about 85% (by weight of the sanitizer).

The sanitizing compositions may further comprise a fragrance. Any suitable fragrance may be used. In some embodiments, the fragrance is D-limonene. In some embodiments, the composition comprises a fragrance agent. In some embodiments, the fragrance agent comprises or is derived from essential oils, absolutes, resinoids, resins, concretes, or synthetic perfume components such as hydrocarbons, alcohols, aldehydes, ketones, ethers, acids, acetals, ketals and nitriles, including saturated and unsaturated compounds, aliphatic, carbocyclic and heterocyclic compounds, or precursors of any of the above. Exemplary fragrant agents include, but are not limited to, *eucalyptus* (*Eucalyptus globulus* or *Eucalyptus citriadora*), pine needles (*Picca excelsa*), Ho-leaves (*Cinnamomum camphora hosch*), peppermint (*Mentha piperita*), neem tree (*Azadirachta excelsa*), bay leaves (*Laurus nobilis*), *litsea* (*Litsea cubeba*), citronella (*Cymbopogon nardus*), elemi (*Canarium luzonicum*), petitgrain citronniers lemon (*Citrus limonum*), grapefruit (*citrus paradisi*), fir tree (*Abies alba pectinata*), lavender (*Lavandula officinalis*), bergamotte (*Citrus aurantium bergamia*), and rosemary (*Rosmarinus officinalis*). In some embodiments, the fragrance agent is derived from a citrus fruit including but not limited to, oranges, lemons, grapefruit, and limes. In some embodiments, the fragrance agent is an acid or terpene derived from a citrus fruit. In some embodiments, the fragrance agent is citric acid or a citric acid derivative. In some embodiments, the fragrance agent is limonene.

In some embodiments, the composition comprises D-limonene. In some embodiments, the concentration of D-limonene in the composition is about 0.1%, about 0.2%, about 0.3%, about 0.4%, about 0.5%, about 0.6%, about 0.7%, about 0.8%, about 0.9%, about 1.0%, about 2.0%, about 3.0%, about 3.0%, or about 4.5%. In some embodiments, the concentration of D-limonene in the composition is in a range of about 0.5% to about 4.5%, about 0.60% to about 2.0%, or about 1.0% to about 1.5%.

In some embodiments, the fragrance is present in the sanitizer in an amount of up to about 5.0% (by weight of the sanitizer). In some embodiments, the sanitizing compositions of the present disclosure comprise one or more fragrance agents in an amount of from about 0.05% to about 5.0% (by weight of the sanitizer). In some embodiments, the sanitizing compositions of the present disclosure comprise one or more fragrance agents in an amount of from about 0.1% to about 5.0%. In some embodiments, the sanitizing compositions of the present disclosure comprise one or more fragrance agents in an amount of from about 0.2% to about 5.0%. In some embodiments, the sanitizing compositions of the present disclosure comprise one or more fragrance agents in an amount of from about 0.3% to about 5.0%. In some embodiments, the sanitizing compositions of the present disclosure comprise one or more fragrance agents in an amount of from about 0.4% to about 5.0%. In some embodiments, the sanitizing compositions of the present disclosure comprise one or more fragrance agents in an amount of from about 0.5% to about 5.0%. In some embodiments, the sanitizing compositions of the present disclosure comprise one or more fragrance agents in an amount of from about 0.6% to about 5.0%. In some embodiments, the sanitizing compositions of the present disclosure comprise one or more fragrance agents in an amount of from about 0.7% to about 5.0%. In some embodiments, the sanitizing compositions of the present disclosure comprise one or more fragrance agents in an amount of from about 0.8% to about 5.0%. In some embodiments, the sanitizing compositions of the present disclosure comprise one or more fragrance agents in an amount of from about 0.9% to about 5.0%. In some embodiments, the sanitizing compositions of the present disclosure comprise one or more fragrance agents in an amount of from about 1.0% to about 5.0%. In some embodiments, the sanitizing compositions of the present disclosure comprise one or more fragrance agents in an amount of from about 1.5% to about 5.0%. In some embodiments, the sanitizing compositions of the present disclosure comprise one or more fragrance agents in an amount of from about 2.0% to about 5.0%. In some embodiments, the sanitizing compositions of the present disclosure comprise one or more fragrance agents in an amount of from about 2.5% to about 5.0%. In some embodiments, the sanitizing compositions of the present disclosure comprise one or more fragrance agents in an amount of from about 3.0% to about 5.0%. In some embodiments, the sanitizing compositions of the present disclosure comprise one or more fragrance agents in an amount of from about 3.5% to about 5.0%. In some embodiments, the sanitizing compositions of the present disclosure comprise one or more fragrance agents in an amount of from about 4.0% to about 5.0%. In some embodiments, the sanitizing compositions of the present disclosure comprise one or more fragrance agents in an amount of from about 4.5% to about 5.0%.

In some embodiments, the sanitizing compositions of the present disclosure comprise one or more fragrance agents in an amount of from about 0.05% to about 4.5% (by weight of the sanitizer). In some embodiments, the sanitizing compositions of the present disclosure comprise one or more fragrance agents in an amount of from about 0.10% to about 4.50%. In some embodiments, the sanitizing compositions of the present disclosure comprise one or more fragrance agents in an amount of from about 0.2% to about 4.5%. In some embodiments, the sanitizing compositions of the present disclosure comprise one or more fragrance agents in an amount of from about 0.3% to about 4.5%. In some embodiments, the sanitizing compositions of the present disclosure comprise one or more fragrance agents in an amount of from about 0.4% to about 4.5%. In some embodiments, the sanitizing compositions of the present disclosure comprise one or more fragrance agents in an amount of from about 0.5% to about 4.5%. In some embodiments, the sanitizing compositions of the present disclosure comprise one or more fragrance agents in an amount of from about 0.6% to about 4.5%. In some embodiments, the sanitizing compositions of the present disclosure comprise one or more fragrance agents in an amount of from about 0.7% to about 4.5%. In some embodiments, the sanitizing compositions of the present disclosure comprise one or more fragrance agents in an amount of from about 0.8% to about 4.5%. In some embodiments, the sanitizing compositions of the present disclosure comprise one or more fragrance agents in an amount of from about 0.9% to about 4.5%. In some embodiments, the sanitizing compositions of the present disclosure comprise one or more fragrance agents in an amount of from about 1.0% to about 4.5%. In some embodiments, the sanitizing compositions of the present disclosure comprise one or more fragrance agents in an amount of from about 1.5% to about 4.5%. In some embodiments, the sanitizing compositions of the present disclosure comprise one or more fragrance agents in an amount of from about 2.0% to about 4.5%. In some embodiments, the sanitizing compositions of the present disclosure comprise one or more fragrance agents in an amount of from about 2.5% to about 4.5%. In some embodiments, the sanitizing compositions of the present disclosure comprise one or more fragrance agents in an amount of from about 3.0% to about 4.5%. In some embodiments, the sanitizing compositions of the present disclosure comprise one or more fragrance agents in an amount of from about 3.5% to about 4.5%. In some embodiments, the sanitizing compositions of the present disclosure comprise one or more fragrance agents in an amount of from about 4.0% to about 4.5%.

In some embodiments, the sanitizing compositions of the present disclosure comprise one or more fragrance agents in an amount of from about 0.05% to about 4.0% (by weight of the sanitizer). In some embodiments, the sanitizing compositions of the present disclosure comprise one or more fragrance agents in an amount of from about 0.10% to about 4.0%. In some embodiments, the sanitizing compositions of the present disclosure comprise one or more fragrance agents in an amount of from about 0.2% to about 4.0%. In some embodiments, the sanitizing compositions of the present disclosure comprise one or more fragrance agents in an amount of from about 0.3% to about 4.0%. In some embodiments, the sanitizing compositions of the present disclosure comprise one or more fragrance agents in an amount of from about 0.4% to about 4.0%. In some embodiments, the sanitizing compositions of the present disclosure comprise one or more fragrance agents in an amount of from about 0.5% to about 4.0%. In some embodiments, the sanitizing compositions of the present disclosure comprise one or more fragrance agents in an amount of from about 0.6% to about 4.0%. In some embodiments, the sanitizing compositions of the present disclosure comprise one or more fragrance agents in an amount of from about 0.7% to about 4.0%. In some embodiments, the sanitizing compositions of the present disclosure comprise one or more fragrance agents in an amount of from about 0.8% to about 4.0%. In some embodiments, the sanitizing compositions of the present disclosure comprise one or more fragrance agents in an amount of from about 0.9% to about 4.0%. In some embodiments, the sanitizing compositions of the present disclosure comprise one or more fragrance agents in an amount of from about 1.0% to about 4.0%. In some embodiments, the sanitizing compositions of the present disclosure comprise one or more fragrance agents in an amount of from about 1.5% to about 4.0%. In some embodiments, the sanitizing compositions of the present disclosure comprise one or more fragrance agents in an amount of from about 2.0% to about 4.0%. In some embodiments, the sanitizing compositions of the present disclosure comprise one or more fragrance agents in an amount of from about 2.5% to about 4.0%. In some embodiments, the sanitizing compositions of the present disclosure comprise one or more fragrance agents in an amount of from about 3.0% to about 4.0%. In some embodiments, the sanitizing compositions of the present disclosure comprise one or more fragrance agents in an amount of from about 3.5% to about 4.0%.

In some embodiments, the sanitizing compositions of the present disclosure comprise one or more fragrance agents in an amount of from about 0.05% to about 3.5% (by weight of the sanitizer). In some embodiments, the sanitizing compositions of the present disclosure comprise one or more fragrance agents in an amount of from about 0.10% to about 3.50%. In some embodiments, the sanitizing compositions of the present disclosure comprise one or more fragrance agents in an amount of from about 0.2% to about 3.5%. In some embodiments, the sanitizing compositions of the present disclosure comprise one or more fragrance agents in an amount of from about 0.3% to about 3.5%. In some embodiments, the sanitizing compositions of the present disclosure comprise one or more fragrance agents in an amount of from about 0.4% to about 3.5%. In some embodiments, the sanitizing compositions of the present disclosure comprise one or more fragrance agents in an amount of from about 0.5% to about 3.5%. In some embodiments, the sanitizing compositions of the present disclosure comprise one or more fragrance agents in an amount of from about 0.6% to about 3.5%. In some embodiments, the sanitizing compositions of the present disclosure comprise one or more fragrance agents in an amount of from about 0.7% to about 3.5%. In some embodiments, the sanitizing compositions of the present disclosure comprise one or more fragrance agents in an amount of from about 0.8% to about 3.5%. In some embodiments, the sanitizing compositions of the present disclosure comprise one or more fragrance agents in an amount of from about 0.9% to about 3.5%. In some embodiments, the sanitizing compositions of the present disclosure comprise one or more fragrance agents in an amount of from about 1.0% to about 3.5%. In some embodiments, the sanitizing compositions of the present disclosure comprise one or more fragrance agents in an amount of from about 1.5% to about 3.5%. In some embodiments, the sanitizing compositions of the present disclosure comprise one or more fragrance agents in an amount of from about 2.0% to about 3.5%. In some embodiments, the sanitizing compositions of the present disclosure comprise one or more fragrance agents in an amount of from about 2.5% to about 3.5%. In some embodiments, the sanitizing compositions of the present disclosure comprise one or more fragrance agents in an amount of from about 3.0% to about 3.5%.

In some embodiments, the sanitizing compositions of the present disclosure comprise one or more fragrance agents in an amount of from about 0.05% to about 3.0% (by weight of the sanitizer). In some embodiments, the sanitizing compositions of the present disclosure comprise one or more fragrance agents in an amount of from about 0.10% to about 3.0%. In some embodiments, the sanitizing compositions of the present disclosure comprise one or more fragrance agents in an amount of from about 0.2% to about 3.0%. In some embodiments, the sanitizing compositions of the present disclosure comprise one or more fragrance agents in an amount of from about 0.3% to about 3.0%. In some embodiments, the sanitizing compositions of the present disclosure comprise one or more fragrance agents in an amount of from about 0.4% to about 3.0%. In some embodiments, the sanitizing compositions of the present disclosure comprise one or more fragrance agents in an amount of from about 0.5% to about 3.0%. In some embodiments, the sanitizing compositions of the present disclosure comprise one or more fragrance agents in an amount of from about 0.6% to about 3.0%. In some embodiments, the sanitizing compositions of the present disclosure comprise one or more fragrance agents in an amount of from about 0.7% to about 3.0%. In some embodiments, the sanitizing compositions of the present disclosure comprise one or more fragrance agents in an amount of from about 0.8% to about 3.0%. In some embodiments, the sanitizing compositions of the present disclosure comprise one or more fragrance agents in an amount of from about 0.9% to about 3.0%. In some embodiments, the sanitizing compositions of the present disclosure comprise one or more fragrance agents in an amount of from about 1.0% to about 3.0%. In some embodiments, the sanitizing compositions of the present disclosure comprise one or more fragrance agents in an amount of from about 1.5% to about 3.0%. In some embodiments, the sanitizing compositions of the present disclosure comprise one or more fragrance agents in an amount of from about 2.0% to about 3.0%. In some embodiments, the sanitizing compositions of the present disclosure comprise one or more fragrance agents in an amount of from about 2.5% to about 3.0%.

In some embodiments, the sanitizing compositions of the present disclosure comprise one or more fragrance agents in an amount of from about 0.05% to about 2.5% (by weight of the sanitizer). In some embodiments, the sanitizing compositions of the present disclosure comprise one or more fragrance agents in an amount of from about 0.10% to about 2.5%. In some embodiments, the sanitizing compositions of the present disclosure comprise one or more fragrance agents in an amount of from about 0.2% to about 2.5%. In some embodiments, the sanitizing compositions of the present disclosure comprise one or more fragrance agents in an amount of from about 0.3% to about 2.5%. In some embodiments, the sanitizing compositions of the present disclosure comprise one or more fragrance agents in an amount of from about 0.4% to about 2.5%. In some embodiments, the sanitizing compositions of the present disclosure comprise one or more fragrance agents in an amount of from about 0.5% to about 2.5%. In some embodiments, the sanitizing compositions of the present disclosure comprise one or more fragrance agents in an amount of from about 0.6% to about 2.5%. In some embodiments, the sanitizing compositions of the present disclosure comprise one or more fragrance agents in an amount of from about 0.7% to about 2.5%. In some embodiments, the sanitizing compositions of the present disclosure comprise one or more fragrance agents in an amount of from about 0.8% to about 2.5%. In some embodiments, the sanitizing compositions of the present disclosure comprise one or more fragrance agents in an amount of from about 0.9% to about 2.5%. In some embodiments, the sanitizing compositions of the present disclosure comprise one or more fragrance agents in an amount of from about 1.0% to about 2.5%.

In some embodiments, the sanitizing compositions of the present disclosure comprise one or more fragrance agents in an amount of from about 1.5% to about 2.5%. In some embodiments, the sanitizing compositions of the present disclosure comprise one or more fragrance agents in an amount of from about 2.0% to about 2.5%. In some embodiments, the sanitizing compositions of the present disclosure comprise one or more fragrance agents in an amount of from about 0.05% to about 2.0% (by weight of the sanitizer). In some embodiments, the sanitizing compositions of the present disclosure comprise one or more fragrance agents in an amount of from about 0.10% to about 2.0%. In some embodiments, the sanitizing compositions of the present disclosure comprise one or more fragrance agents in an amount of from about 0.2% to about 2.0%. In some embodiments, the sanitizing compositions of the present disclosure comprise one or more fragrance agents in an amount of from about 0.3% to about 2.0%. In some embodiments, the sanitizing compositions of the present disclosure comprise one or more fragrance agents in an amount of from about 0.4% to about 2.0%. In some embodiments, the sanitizing compositions of the present disclosure comprise one or more fragrance agents in an amount of from about 0.5% to about 2.0%. In some embodiments, the sanitizing compositions of the present disclosure comprise one or more fragrance agents in an amount of from about 0.6% to about 2.0%. In some embodiments, the sanitizing compositions of the present disclosure comprise one or more fragrance agents in an amount of from about 0.7% to about 2.0%. In some embodiments, the sanitizing compositions of the present disclosure comprise one or more fragrance agents in an amount of from about 0.8% to about 2.0%. In some embodiments, the sanitizing compositions of the present disclosure comprise one or more fragrance agents in an amount of from about 0.9% to about 2.0%. In some embodiments, the sanitizing compositions of the present disclosure comprise one or more fragrance agents in an amount of from about 1.0% to about 2.0%. In some embodiments, the sanitizing compositions of the present disclosure comprise one or more fragrance agents in an amount of from about 1.5% to about 2.0%.

In some embodiments, the sanitizing compositions of the present disclosure comprise one or more fragrance agents in an amount of from about 0.05% to about 1.5% (by weight of the sanitizer). In some embodiments, the sanitizing compositions of the present disclosure comprise one or more fragrance agents in an amount of from about 0.10% to about 1.50%. In some embodiments, the sanitizing compositions of the present disclosure comprise one or more fragrance agents in an amount of from about 0.2% to about 1.5%. In some embodiments, the sanitizing compositions of the present disclosure comprise one or more fragrance agents in an amount of from about 0.3% to about 1.5%. In some embodiments, the sanitizing compositions of the present disclosure comprise one or more fragrance agents in an amount of from about 0.4% to about 1.5%. In some embodiments, the sanitizing compositions of the present disclosure comprise one or more fragrance agents in an amount of from about 0.5% to about 1.5%. In some embodiments, the sanitizing compositions of the present disclosure comprise one or more fragrance agents in an amount of from about 0.6% to about 1.5%. In some embodiments, the sanitizing compositions of the present disclosure comprise one or more fragrance agents in an amount of from about 0.7% to about 1.5%. In some embodiments, the sanitizing compositions of the present disclosure comprise one or more fragrance agents in an amount of from about 0.8% to about 1.5%. In some embodiments, the sanitizing compositions of the present disclosure comprise one or more fragrance agents in an amount of from about 0.9% to about 1.5%. In some embodiments, the sanitizing compositions of the present disclosure comprise one or more fragrance agents in an amount of from about 1.0% to about 1.5%.

In some embodiments, the sanitizing compositions of the present disclosure comprise one or more fragrance agents in an amount of from about 0.05% to about 1.0% (by weight of the sanitizer). In some embodiments, the sanitizing compositions of the present disclosure comprise one or more fragrance agents in an amount of from about 0.10% to about 1.0%. In some embodiments, the sanitizing compositions of the present disclosure comprise one or more fragrance agents in an amount of from about 0.2% to about 1.0%. In some embodiments, the sanitizing compositions of the present disclosure comprise one or more fragrance agents in an amount of from about 0.3% to about 1.0%. In some embodiments, the sanitizing compositions of the present disclosure comprise one or more fragrance agents in an amount of from about 0.4% to about 1.0%. In some embodiments, the sanitizing compositions of the present disclosure comprise one or more fragrance agents in an amount of from about 0.5% to about 1.0%. In some embodiments, the sanitizing compositions of the present disclosure comprise one or more fragrance agents in an amount of from about 0.6% to about 1.0%. In some embodiments, the sanitizing compositions of the present disclosure comprise one or more fragrance agents in an amount of from about 0.7% to about 1.0%. In some embodiments, the sanitizing compositions of the present disclosure comprise one or more fragrance agents in an amount of from about 0.8% to about 1.0%. In some embodiments, the sanitizing compositions of the present disclosure comprise one or more fragrance agents in an amount of from about 0.9% to about 1.0%.

The pH of the sanitizing compositions may be controlled to be within any desired range, depending on the target surface/soil. In some embodiments, the sanitizer is formulated for topical application on a human body. In some embodiments, the sanitizer has a neutral pH. In some embodiments, various pH modifiers may be utilized in the sanitizer to achieve the desired pH level. Any suitable acid or alkali material may be used as a pH modifier. For instance, some examples of basic pH modifiers that may be used in the sanitizer include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine. Other examples of suitable basic pH modifiers include tris amino 40% (available from Angus Chemical Company), AMP-95 (aminomethylpropanol) (available from Angus Chemical Company), triisopropanolamine (available from Dow Chemical Company), diisopropanolamine (available from Dow Chemical Company), Neutrol® TE (tetrahydroxypropylethylenediamine) (available from BASF), and Ethomeen® C-25 (PEG-15 cocoamine) (available from Akzo Nobel).

Some examples of acidic pH modifiers that may be used in the present disclosure include, but are not limited to, mineral acids; and carboxylic acids; and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, and alginic acid.

In some embodiments, the pH modifier is present in the sanitizing compositions in an amount of up to about 5% (by weight of the sanitizer).

Optionally, one or more viscosity enhancers, such as thickeners, gelling agents, and the like may be added to the sanitizing compositions to increase the viscosity of the sanitizer. Suitable viscosity enhancers include clays and derivatives thereof, silicates, silicas and derivatives thereof, and combinations thereof. Suitable clays and derivatives thereof include, but are not limited to, bentonite and derivatives thereof such as quaternium-18 bentonite, hectorite and derivatives thereof such as quaternium-18 hectorite, montmorillonite, and combinations thereof. Suitable silicates include, but are not limited to, magnesium aluminum silicate, sodium magnesium silicate, lithium magnesium silicate, tromethamine magnesium aluminum silicate, and combinations thereof. Suitable silicas and derivatives thereof include, but are not limited to, silica, hydrated silica, hydrophobic silica, silica silylate, silica methyl silylate, colloidal silicone dioxide, fumed silica, and combinations thereof.

Other examples of suitable viscosity enhancers include polyolefin resins, lipophilic/oil thickeners, ethylene/vinyl acetate copolymers, polyethylene, cetyl hydroxy ethyl cellulose, hydroxyethylcellulose, hydroxypropyl methylcellulose, hydroxypropylcellulose, other organically modified celluloses, PVP/decane copolymer, PVM/MA decadiene crosspolymer, PVP/eicosene copolymer, PVP/hexadecane copolymer, butylated PVP, carbomers, acrylic based thickeners, polyethylene glycol 600, polyethylene glycols, myristyl alcohol, cetyl alcohol, stearyl alcohol, behenyl alcohol, PEG-150 distearate, PEG-160 diisostearate, polyglyceryl-8.5 behenate/eicosadioate, disteareth-8.50 IPDI, polyacrylamidomethylpropane sulfonic acid, silicone crosspolymers, polyamide blends, and combinations thereof.

In some embodiments, the sanitizing compositions comprise one or more gelling agents in an amount of up to about 20% (by weight of the sanitizer). In some embodiments, the gelling is present in the sanitizer in an amount of up to about 5.0% (by weight of the sanitizer). In some embodiments, the sanitizing compositions of the present disclosure comprise one or more gelling agents in an amount of from about 0.05% to about 5.0% (by weight of the sanitizer). In some embodiments, the sanitizing compositions of the present disclosure comprise one or more gelling agents in an amount of from about 0.1% to about 5.0%. In some embodiments, the sanitizing compositions of the present disclosure comprise one or more gelling agents in an amount of from about 0.2% to about 5.0%. In some embodiments, the sanitizing compositions of the present disclosure comprise one or more gelling agents in an amount of from about 0.3% to about 5.0%. In some embodiments, the sanitizing compositions of the present disclosure comprise one or more gelling agents in an amount of from about 0.4% to about 5.0%. In some embodiments, the sanitizing compositions of the present disclosure comprise one or more gelling agents in an amount of from about 0.5% to about 5.0%. In some embodiments, the sanitizing compositions of the present disclosure comprise one or more gelling agents in an amount of from about 0.6% to about 5.0%. In some embodiments, the sanitizing compositions of the present disclosure comprise one or more gelling agents in an amount of from about 0.7% to about 5.0%. In some embodiments, the sanitizing compositions of the present disclosure comprise one or more gelling agents in an amount of from about 0.8% to about 5.0%. In some embodiments, the sanitizing compositions of the present disclosure comprise one or more gelling agents in an amount of from about 0.9% to about 5.0%. In some embodiments, the sanitizing compositions of the present disclosure comprise one or more gelling agents in an amount of from about 1.0% to about 5.0%. In some embodiments, the sanitizing compositions of the present disclosure comprise one or more gelling agents in an amount of from about 1.5% to about 5.0%. In some embodiments, the sanitizing compositions of the present disclosure comprise one or more gelling agents in an amount of from about 2.0% to about 5.0%. In some embodiments, the sanitizing compositions of the present disclosure comprise one or more gelling agents in an amount of from about 2.5% to about 5.0%. In some embodiments, the sanitizing compositions of the present disclosure comprise one or more gelling agents in an amount of from about 3.0% to about 5.0%. In some embodiments, the sanitizing compositions of the present disclosure comprise one or more gelling agents in an amount of from about 3.5% to about 5.0%. In some embodiments, the sanitizing compositions of the present disclosure comprise one or more gelling agents in an amount of from about 4.0% to about 5.0%. In some embodiments, the sanitizing compositions of the present disclosure comprise one or more gelling agents in an amount of from about 4.5% to about 5.0%.

In some embodiments, the sanitizing compositions of the present disclosure comprise one or more gelling agents in an amount of from about 0.05% to about 4.5% (by weight of the sanitizer). In some embodiments, the sanitizing compositions of the present disclosure comprise one or more gelling agents in an amount of from about 0.1% to about 4.5%. In some embodiments, the sanitizing compositions of the present disclosure comprise one or more gelling agents in an amount of from about 0.2% to about 4.5%. In some embodiments, the sanitizing compositions of the present disclosure comprise one or more gelling agents in an amount of from about 0.3% to about 4.5%. In some embodiments, the sanitizing compositions of the present disclosure comprise one or more gelling agents in an amount of from about 0.4% to about 4.5%. In some embodiments, the sanitizing compositions of the present disclosure comprise one or more gelling agents in an amount of from about 0.5% to about 4.5%. In some embodiments, the sanitizing compositions of the present disclosure comprise one or more gelling agents in an amount of from about 0.6% to about 4.5%. In some embodiments, the sanitizing compositions of the present disclosure comprise one or more gelling agents in an amount of from about 0.7% to about 4.5%. In some embodiments, the sanitizing compositions of the present disclosure comprise one or more gelling agents in an amount of from about 0.8% to about 4.5%. In some embodiments, the sanitizing compositions of the present disclosure comprise one or more gelling agents in an amount of from about 0.9% to about 4.5%. In some embodiments, the sanitizing compositions of the present disclosure comprise one or more gelling agents in an amount of from about 1.0% to about 4.5%. In some embodiments, the sanitizing compositions of the present disclosure comprise one or more gelling agents in an amount of from about 1.5% to about 4.5%. In some embodiments, the sanitizing compositions of the present disclosure comprise one or more gelling agents in an amount of from about 2.0% to about 4.5%. In some embodiments, the sanitizing compositions of the present disclosure comprise one or more gelling agents in an amount of from about 2.5% to about 4.5%. In some embodiments, the sanitizing compositions of the present disclosure comprise one or more gelling agents in an amount of from about 3.0% to about 4.5%. In some embodiments, the sanitizing compositions of the present disclosure comprise one or more gelling agents in an amount of from about 3.5% to about 4.5%. In some embodiments, the sanitizing compositions of the present disclosure comprise one or more gelling agents in an amount of from about 4.0% to about 4.5%.

In some embodiments, the sanitizing compositions of the present disclosure comprise one or more gelling agents in an amount of from about 0.05% to about 4.0% (by weight of the sanitizer). In some embodiments, the sanitizing compositions of the present disclosure comprise one or more gelling agents in an amount of from about 0.1% to about 4.0%. In some embodiments, the sanitizing compositions of the present disclosure comprise one or more gelling agents in an amount of from about 0.2% to about 4.0%. In some embodiments, the sanitizing compositions of the present disclosure comprise one or more gelling agents in an amount of from about 0.3% to about 4.0%. In some embodiments, the sanitizing compositions of the present disclosure comprise one or more gelling agents in an amount of from about 0.4% to about 4.0%. In some embodiments, the sanitizing compositions of the present disclosure comprise one or more gelling agents in an amount of from about 0.5% to about 4.0%. In some embodiments, the sanitizing compositions of the present disclosure comprise one or more gelling agents in an amount of from about 0.6% to about 4.0%. In some embodiments, the sanitizing compositions of the present disclosure comprise one or more gelling agents in an amount of from about 0.7% to about 4.0%. In some embodiments, the sanitizing compositions of the present disclosure comprise one or more gelling agents in an amount of from about 0.8% to about 4.0%. In some embodiments, the sanitizing compositions of the present disclosure comprise one or more gelling agents in an amount of from about 0.9% to about 4.0%. In some embodiments, the sanitizing compositions of the present disclosure comprise one or more gelling agents in an amount of from about 1.0% to about 4.0%. In some embodiments, the sanitizing compositions of the present disclosure comprise one or more gelling agents in an amount of from about 1.5% to about 4.0%. In some embodiments, the sanitizing compositions of the present disclosure comprise one or more gelling agents in an amount of from about 2.0% to about 4.0%. In some embodiments, the sanitizing compositions of the present disclosure comprise one or more gelling agents in an amount of from about 2.5% to about 4.0%. In some embodiments, the sanitizing compositions of the present disclosure comprise one or more gelling agents in an amount of from about 3.0% to about 4.0%. In some embodiments, the sanitizing compositions of the present disclosure comprise one or more gelling agents in an amount of from about 3.5% to about 4.0%.

In some embodiments, the sanitizing compositions of the present disclosure comprise one or more gelling agents in an amount of from about 0.05% to about 3.5% (by weight of the sanitizer). In some embodiments, the sanitizing compositions of the present disclosure comprise one or more gelling agents in an amount of from about 0.1% to about 3.5%. In some embodiments, the sanitizing compositions of the present disclosure comprise one or more gelling agents in an amount of from about 0.2% to about 3.5%. In some embodiments, the sanitizing compositions of the present disclosure comprise one or more gelling agents in an amount of from about 0.3% to about 3.5%. In some embodiments, the sanitizing compositions of the present disclosure comprise one or more gelling agents in an amount of from about 0.4% to about 3.5%. In some embodiments, the sanitizing compositions of the present disclosure comprise one or more gelling agents in an amount of from about 0.5% to about 3.5%. In some embodiments, the sanitizing compositions of the present disclosure comprise one or more gelling agents in an amount of from about 0.6% to about 3.5%. In some embodiments, the sanitizing compositions of the present disclosure comprise one or more gelling agents in an amount of from about 0.7% to about 3.5%. In some embodiments, the sanitizing compositions of the present disclosure comprise one or more gelling agents in an amount of from about 0.8% to about 3.5%. In some embodiments, the sanitizing compositions of the present disclosure comprise one or more gelling agents in an amount of from about 0.9% to about 3.5%. In some embodiments, the sanitizing compositions of the present disclosure comprise one or more gelling agents in an amount of from about 1.0% to about 3.5%. In some embodiments, the sanitizing compositions of the present disclosure comprise one or more gelling agents in an amount of from about 1.5% to about 3.5%. In some embodiments, the sanitizing compositions of the present disclosure comprise one or more gelling agents in an amount of from about 2.0% to about 3.5%. In some embodiments, the sanitizing compositions of the present disclosure comprise one or more gelling agents in an amount of from about 2.5% to about 3.5%. In some embodiments, the sanitizing compositions of the present disclosure comprise one or more gelling agents in an amount of from about 3.0% to about 3.5%.

In some embodiments, the sanitizing compositions of the present disclosure comprise one or more gelling agents in an amount of from about 0.05% to about 3.0% (by weight of the sanitizer). In some embodiments, the sanitizing compositions of the present disclosure comprise one or more gelling agents in an amount of from about 0.1% to about 3.0%. In some embodiments, the sanitizing compositions of the present disclosure comprise one or more gelling agents in an amount of from about 0.2% to about 3.0%. In some embodiments, the sanitizing compositions of the present disclosure comprise one or more gelling agents in an amount of from about 0.3% to about 3.0%. In some embodiments, the sanitizing compositions of the present disclosure comprise one or more gelling agents in an amount of from about 0.4% to about 3.0%. In some embodiments, the sanitizing compositions of the present disclosure comprise one or more gelling agents in an amount of from about 0.5% to about 3.0%. In some embodiments, the sanitizing compositions of the present disclosure comprise one or more gelling agents in an amount of from about 0.6% to about 3.0%. In some embodiments, the sanitizing compositions of the present disclosure comprise one or more gelling agents in an amount of from about 0.7% to about 3.0%. In some embodiments, the sanitizing compositions of the present disclosure comprise one or more gelling agents in an amount of from about 0.8% to about 3.0%. In some embodiments, the sanitizing compositions of the present disclosure comprise one or more gelling agents in an amount of from about 0.9% to about 3.0%. In some embodiments, the sanitizing compositions of the present disclosure comprise one or more gelling agents in an amount of from about 1.0% to about 3.0%. In some embodiments, the sanitizing compositions of the present disclosure comprise one or more gelling agents in an amount of from about 1.5% to about 3.0%. In some embodiments, the sanitizing compositions of the present disclosure comprise one or more gelling agents in an amount of from about 2.0% to about 3.0%. In some embodiments, the sanitizing compositions of the present disclosure comprise one or more gelling agents in an amount of from about 2.5% to about 3.0%.

In some embodiments, the sanitizing compositions of the present disclosure comprise one or more gelling agents in an amount of from about 0.05% to about 2.5% (by weight of the sanitizer). In some embodiments, the sanitizing compositions of the present disclosure comprise one or more gelling agents in an amount of from about 0.1% to about 2.5%. In some embodiments, the sanitizing compositions of the present disclosure comprise one or more gelling agents in an amount of from about 0.2% to about 2.5%. In some embodiments, the sanitizing compositions of the present disclosure comprise one or more gelling agents in an amount of from about 0.3% to about 2.5%. In some embodiments, the sanitizing compositions of the present disclosure comprise one or more gelling agents in an amount of from about 0.4% to about 2.5%. In some embodiments, the sanitizing compositions of the present disclosure comprise one or more gelling agents in an amount of from about 0.5% to about 2.5%. In some embodiments, the sanitizing compositions of the present disclosure comprise one or more gelling agents in an amount of from about 0.6% to about 2.5%. In some embodiments, the sanitizing compositions of the present disclosure comprise one or more gelling agents in an amount of from about 0.7% to about 2.5%. In some embodiments, the sanitizing compositions of the present disclosure comprise one or more gelling agents in an amount of from about 0.8% to about 2.5%. In some embodiments, the sanitizing compositions of the present disclosure comprise one or more gelling agents in an amount of from about 0.9% to about 2.5%. In some embodiments, the sanitizing compositions of the present disclosure comprise one or more gelling agents in an amount of from about 1.0% to about 2.5%. In some embodiments, the sanitizing compositions of the present disclosure comprise one or more gelling agents in an amount of from about 1.5% to about 2.5%. In some embodiments, the sanitizing compositions of the present disclosure comprise one or more gelling agents in an amount of from about 2.0% to about 2.5%.

In some embodiments, the sanitizing compositions of the present disclosure comprise one or more gelling agents in an amount of from about 0.05% to about 2.0% (by weight of the sanitizer). In some embodiments, the sanitizing compositions of the present disclosure comprise one or more gelling agents in an amount of from about 0.1% to about 2.0%. In some embodiments, the sanitizing compositions of the present disclosure comprise one or more gelling agents in an amount of from about 0.2% to about 2.0%. In some embodiments, the sanitizing compositions of the present disclosure comprise one or more gelling agents in an amount of from about 0.3% to about 2.0%. In some embodiments, the sanitizing compositions of the present disclosure comprise one or more gelling agents in an amount of from about 0.4% to about 2.0%. In some embodiments, the sanitizing compositions of the present disclosure comprise one or more gelling agents in an amount of from about 0.5% to about 2.0%. In some embodiments, the sanitizing compositions of the present disclosure comprise one or more gelling agents in an amount of from about 0.6% to about 2.0%. In some embodiments, the sanitizing compositions of the present disclosure comprise one or more gelling agents in an amount of from about 0.7% to about 2.0%. In some embodiments, the sanitizing compositions of the present disclosure comprise one or more gelling agents in an amount of from about 0.8% to about 2.0%. In some embodiments, the sanitizing compositions of the present disclosure comprise one or more gelling agents in an amount of from about 0.9% to about 2.0%. In some embodiments, the sanitizing compositions of the present disclosure comprise one or more gelling agents in an amount of from about 1.0% to about 2.0%. In some embodiments, the sanitizing compositions of the present disclosure comprise one or more gelling agents in an amount of from about 1.5% to about 2.0%.

In some embodiments, the sanitizing compositions of the present disclosure comprise one or more gelling agents in an amount of from about 0.05% to about 1.5% (by weight of the sanitizer). In some embodiments, the sanitizing compositions of the present disclosure comprise one or more gelling agents in an amount of from about 0.1% to about 1.5%. In some embodiments, the sanitizing compositions of the present disclosure comprise one or more gelling agents in an amount of from about 0.2% to about 1.5%. In some embodiments, the sanitizing compositions of the present disclosure comprise one or more gelling agents in an amount of from about 0.3% to about 1.5%. In some embodiments, the sanitizing compositions of the present disclosure comprise one or more gelling agents in an amount of from about 0.4% to about 1.5%. In some embodiments, the sanitizing compositions of the present disclosure comprise one or more gelling agents in an amount of from about 0.5% to about 1.5%. In some embodiments, the sanitizing compositions of the present disclosure comprise one or more gelling agents in an amount of from about 0.6% to about 1.5%. In some embodiments, the sanitizing compositions of the present disclosure comprise one or more gelling agents in an amount of from about 0.7% to about 1.5%. In some embodiments, the sanitizing compositions of the present disclosure comprise one or more gelling agents in an amount of from about 0.8% to about 1.5%. In some embodiments, the sanitizing compositions of the present disclosure comprise one or more gelling agents in an amount of from about 0.9% to about 1.5%. In some embodiments, the sanitizing compositions of the present disclosure comprise one or more gelling agents in an amount of from about 1.0% to about 1.5%.

In some embodiments, the sanitizing compositions of the present disclosure comprise one or more gelling agents in an amount of from about 0.05% to about 1.0% (by weight of the sanitizer). In some embodiments, the sanitizing compositions of the present disclosure comprise one or more gelling agents in an amount of from about 0.1% to about 1.0%. In some embodiments, the sanitizing compositions of the present disclosure comprise one or more gelling agents in an amount of from about 0.2% to about 1.0%. In some embodiments, the sanitizing compositions of the present disclosure comprise one or more gelling agents in an amount of from about 0.3% to about 1.0%. In some embodiments, the sanitizing compositions of the present disclosure comprise one or more gelling agents in an amount of from about 0.4% to about 1.0%. In some embodiments, the sanitizing compositions of the present disclosure comprise one or more gelling agents in an amount of from about 0.5% to about 1.0%. In some embodiments, the sanitizing compositions of the present disclosure comprise one or more gelling agents in an amount of from about 0.6% to about 1.0%. In some embodiments, the sanitizing compositions of the present disclosure comprise one or more gelling agents in an amount of from about 0.7% to about 1.0%. In some embodiments, the sanitizing compositions of the present disclosure comprise one or more gelling agents in an amount of from about 0.8% to about 1.0%. In some embodiments, the sanitizing compositions of the present disclosure comprise one or more gelling agents in an amount of from about 0.9% to about 1.0%.

In certain embodiments, the sanitizing compositions comprise various preservatives to increase the shelf life of the sanitizer. Exemplary preservatives that can be used in the present disclosure include, but are not limited to, Kathon CG, which is a mixture of methylchloroisothiazolinone and methylisothiazolinone available from Rohm & Haas; Mackstat H 66 (available from McIntyre Group, Chicago, Ill.); DMDM hydantoin (e.g., Glydant Plus, Lonza, Inc., Fair Lawn, N.J.); tetrasodium EDTA; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; amidazolidinyl urea; diazolidinyl urea; and the like. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate).

When utilized, the amount of the preservative present in the sanitizer can generally vary depending on the relative amounts of the other components present within the sanitizer. For example, in some embodiments, the preservative is present in the sanitizer in an amount between about 0.001% to about 5% (by weight of the sanitizer), in some embodiments between about 0.001% to about 1% (by weight of the sanitizer), and in some embodiments, between about 0.010% to about 10% (by weight of the sanitizer).

In one embodiment, the sanitizer may additionally include one or more sequestrants or chelating agents. The sequestrants may act to enhance preservative efficacy, and bind metals that could discolor the sanitizer or hinder sanitizer stability. In particular, water often contains metal ions, such as calcium ions, that might react with anionic components (e.g., surfactants, acids, etc.) present within the sanitizer.

Some examples of sequestrants that may be used in the sanitizer of the present disclosure include, but are not limited to, ethylenediamines, ethylenediaminetetraacetic acids (EDTA) acid and/or salts thereof, citric acids and/or salts thereof, glucuronic acids and/or salts thereof, polyphosphates, organophosphates, dimercaprols, and the like.

When utilized, the amount of the sequestrants present in the sanitizer can generally vary depending on the relative amounts of the other components present within the sanitizer. For example, in some embodiments, the sequestrants are present in the sanitizer in an amount between about 0.010% to about % (by weight of the sanitizer and in some embodiments between about 0.05% to about 1.0% (by weight of the sanitizer).

The sanitizers of the present disclosure may further comprise skin conditioning agents that may help the skin retain moisture, improve softness, or improve texture. Skin conditioning agents include, for example, amino acids, including alanine, serine, and glycine; allantoin, keratin, and methyl glucose dioleate; alpha-hydroxy acids, including lactic acid and glycolic acid, which act by loosening dead skin cells from the skin's surface; other moisturizers (agents that add or hold water in dry skin) including, but not limited to, *echinacea* (an extract of the coneflower plant) and shea butter; exfoliation agents; lubricants; skin-firming agents; anti-callous agents; anti-acne agents; anti-rosacea agents; anti-aging agents; anti-wrinkle agents; anti-dandruff agents; anti-irritants; anti-redness agents such as aloe extract (aloe vera); anti-inflammatory agents; skin health benefit agents;

wound care agents; skin lipids; enzymes; scar care agents; powders; botanical extracts; vitamins; minerals; sunscreens; surfactants; drugs; quaternary ammonium compounds; and the like. In some embodiments, the skin conditioning agent is aloe vera.

In one embodiment, the skin conditioning agent is a cationic compound such as a quaternium salt, polyquaternium, quaternium, quaternium hectorite (e.g., quaternium-18 hectorite), silicone quaternium materials, cationic surfactant, or combination thereof. One example is a quaternary ammonium compound, such as a quaternary ammonium salt.

Examples of cationic quaternary ammonium salts include, but are not limited to conventionally known monoalkyl quaternary ammonium salts, dialkyl quaternary ammonium salts, and tetra-alkyl quaternary ammonium salts, such as: (1) Acyclic quaternary ammonium salts having at least two $C_8$ to $C_{30}$, and preferably $C_{12}$ to $C_{22}$ alkyl or alkenyl chains, such as: dimethyl ditallow ammonium methylsulfate, di(hydrogenated tallow)dimethyl ammonium methylsulfate, distearyldimethyl ammonium methylsulfate, dicocodimethyl ammonium methylsulfate, and the like. In one embodiment, the skin conditioning agent is a water insoluble quaternary ammonium material which comprises a compound having two $C_{12}$ to $C_{18}$ alkyl or alkenyl groups connected to the molecule via at least one ester link. In another embodiment, the quaternary ammonium material has two ester links present. (2) Cyclic quaternary ammonium salts of the imidazolinium type such as di(hydrogenated tallow)dimethyl imidazolinium methyl sulfate, 1-ethylene-bis(2-tallow-1-methyl)imidazolinium methyl sulfate, and the like. (3) Diamido quaternary ammonium salts such as: methyl-bis (hydrogenated tallow amidoethyl)-2-hydroxethyl ammonium methyl sulfate, methyl bi(tallowamidoethyl)-2-hydroxypropyl ammonium methylsulfate, and the like. (4) Biodegradable quaternary ammonium salts such as N,N-di (tallowoyl-oxy-ethyl)-N,N-dimethyl ammonium methyl sulfate, and N,N-di(tallowoyl-oxy-propyl)-N,N-dimethyl ammonium methyl sulfate.

Suitable polyquaterniums for use in the moisturizing sanitizing compositions include Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-8.5, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-21, Polyquaternium-22, Polyquaternium-23, Polyquaternium-24, Polyquaternium-25, Polyquaternium-26, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-38, Polyquaternium-39, Polyquaternium-40, Polyquaternium-41, Polyquaternium-42, Polyquaternium-43, Polyquaternium-44, Polyquaternium-45, Polyquaternium-46, Polyquaternium-47, Polyquaternium-48, Polyquaternium-49, Polyquaternium-50, Polyquaternium-51, Polyquaternium-52, Polyquaternium-53, Polyquaternium-54, Polyquaternium-55, Polyquaternium-56, Polyquaternium-57, Polyquaternium-58, Polyquaternium-59, Polyquaternium-60, Polyquaternium-61, Polyquaternium-62, Polyquaternium-63, Polyquaternium-64, Polyquaternium-65, Polyquaternium-66, Polyquaternium-67, Polyquaternium-68, Polyquaternium-69, Polyquaternium-70, Polyquaternium-71, Polyquaternium-72, Polyquaternium-73, Polyquaternium-74, Polyquaternium-60, Polyquaternium-76, and Polyquaternium-79.

Suitable quaterniums include Quaternium-8, Quaternium-14, Quaternium-15, Quaternium-16, Quaternium-18, and Quaternium-60.

Other suitable cationic compounds include silicone quaternium materials, such as silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-8.5, silicone quaternium-11, silicone quaternium-12, silicone quaternium-15, silicone quaternium-16, silicone quaternium-17, silicone quaternium-18, silicone quaternium-19, silicone quaternium-20, and silicone quaternium-21.

Suitable cationic surfactants for use in the moisturizing sanitizing compositionss of the present disclosure include, for example, alkyl ammonium salts, polymeric ammonium salts, alkyl pyridinium salts, aryl ammonium salts, alkyl aryl ammonium salts, silicone quaternary ammonium compounds, and combinations thereof. Specific examples of cationic surfactants include behenyltrimonium chloride, stearalkonium chloride, distearalkonium chloride, chlorohexidine diglutamate, polyhexamethylene biguanide (PHMB), cetyl pyridinium chloride, benzammonium chloride, benzalkonium chloride, and combinations thereof.

Other examples of suitable quaternary ammonium compounds include behentrimonium methosulfate, cetrimonium chloride, cocamidopropyl pg-dimonium chloride, guar hydroxypropyltrimonium chloride, isostearamidopropyl morpholine lactate, quaternium-18 hectorite, quaternium-79 hydrolyzed silk, quaternium-79 hydrolyzed soy protein, rape seed amidopropyl ethyldimonium ethosulfate, cetyl triethylmonium dimethicone PEG-8 succinate, palmitamidopropyltrimonium chloride, butylglucosides, hydroxypropyltrimonium chloride, laurdimoniumhydroxypropyl decylglucosides chloride, and the like Other suitable cationic compounds for use in the hand sanitizing compositions of the present disclosure include those cationic compounds listed in International Cosmetic Ingredient Dictionary and Handbook, $11^{th}$ Edition (2006) and in 2007 Cosmetic Bench Reference, available on the World Wide Web at CosmeticBenchReference.com, both of which are incorporated by reference herein to the extent they are consistent herewith.

When utilized, the amount of the skin conditioning agent in the sanitizer can generally vary depending on the relative amounts of the other components present within the sanitizer. For example, in some embodiments, the skin conditioning agent is present in the sanitizer in an amount between about 0.01% to about 8.5% (by weight of the sanitizer), in some embodiments between about 0.5% to about 8% (by weight of the sanitizer), and in some embodiments, between about 1% to about 5% (by weight of the sanitizer).

In order to better enhance the sanitizer, other optional ingredients can also be used. For instance, some classes of ingredients that can be used include, but are not limited to: anti-microbial agents, antioxidants (product integrity); astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); hydrotropes (helps dissolve some antimicrobial agents); opacifiers (reduce the clarity or transparent appearance of the product); skin exfoliating agents (ingredients that increase the rate of skin cell turnover such as alpha hydroxy acids and beta hydroxyacids); dyes or colorants; and the like.

Examples of gelling agents or viscosity modifying agents include, but are not limited to, as polyvinyl alcohol, polyethylene oxide, different poloxamers, carbopols, or celluloses such as ethyl cellulose, hydroxyl ethyl cellulose, hydroxyl propyl cellulose, hydroxyl propyl methyl cellulose, sulfoxides or similar compounds such as dimethylsulfoxide, dimethylsulfoxide, dimethylacetamide, dimethylformamide, pyrrolidones such as 2-pyrrolidone, N-methyl-2-pyrrolidone, 1-lauryl-2-pyrrolidone, alcohols such as ethanol, 1-octanol, 1-hexanol, 1-decanol, lauryl alcohol, linolenyl alcohol, glycols such as propylene glycol, butane-1,2-diol, polyethylene glycol 400, urea and derivatives urea, such as 1-dodecylurea, 1-dodecyl-3-methylurea,1-dodecyl-3-methylthiourea, azone and azone like molecules such as (laurocapram; 1-dodecylazacycloheptan-2-one), 1-alkyl- or 1-alkenylazacycloalkanones, enzymes acid phosphatase, calonase, papain Iminosulfuranes S, S-dimethyl-N-(5-nitro-2-pyridyl) iminosulfurane, S, S-dimethyl-N-(4-bromobenzoyl) iminosulfurane, cyclodextrins 2-hydroxypropyl-β-cyclodextrin, methylated-β-cyclodextrin, fatty acid esters such as cetyl lactate, butylacetate, isopropyl myristate Fatty acids alkanoic acids, oleic acid, lauric acid, capric acid, surfactants such as sorbitan monopalmitate, sorbitan trioleate, cetyl trimethyl ammonium bromide, sodium lauryl sulfate, terpenes such as limonene, nerolidol, farnesol, carvone, menthone, polymers such as β-D-glucopyranosyl-terminated oligodimethylsiloxanes, 1-alkyl-3-β-D-glucopyranosyl-1,1,3,3-tetramethyldisiloxanes Monoolein monoolein Oxazolidinones 4-decyloxazolidin-2-one, 3-acetyl-4-decyloxazolidin-2-one, carbomer, methyl cellulose, sodium carboxyl methyl cellulose, carrageenan, colloidal silicon dioxide, guar gum, gelatin, alginic acid, sodium alginate, and fumed silica. In some embodiments, the gelling agent is a hydroxyethyl cellulose (HEC), hydroxypropyl cellulose (HPC), hydroxypropylmethyl cellulose (HPMC), or a combination thereof. In some embodiments, the gelling agent is HPC.

In some embodiments, the combination of a gelling agent and a pharmaceutically acceptable solvent is referred to as a gel base. In some embodiments, a gel base is created prior to the addition of an ionic liquid to the gel base. In some embodiments, the ionic liquid is added into the gel base. In some embodiments, the gel base is added into the ionic liquid.

In some embodiments, the gel base comprises water and a gelling agent. In some embodiments, the gel base comprises diisopropyl adipate and a gelling agent. In some embodiments, the gel base comprises PEG400 and a gelling agent. In some embodiments, the gel base comprises propylene glycol and a gelling agent. In some embodiments, the gelling agent is HEC, HPC, or HPMC. In some embodiments, the gel base comprises ethanol and a gelling agent. In some embodiments, the gel base further comprises glycerin, propylene glycol, ethanol, or a combination thereof.

In one example, the gel base comprises diisopropyl adipate, ethanol, glycerin, and HPC. In some embodiments, the gel base comprises 25% w/w of diisopropyl adipate, 43% w/w ethanol, 30% w/w glycerin, and 3% w/w HPC. In another example, the gel base comprises diisopropyl adipate, ethanol, propylene glycol, and HPC. In some embodiments, the gel base comprises 25% w/w of diisopropyl adipate, 13% w/w ethanol, 60% w/w propylene glycol, and 3% w/w HPC.

In some embodiments, a composition comprises a bulking agent with a concentration from 1 to 8.5%. In some embodiments, a composition comprises a gelling agent with a concentration from 1 to 8.5%.

In some embodiments, the composition further comprises anon-ionic surfactant. In some embodiments, the non-ionic surfactant is poloxamer or polysorbate 60. In some embodiments, the poloxamer is a Pluronic®, Kolliphor®, or Synperonic®. In some embodiments, the non-ionic surfactant comprises a concentration in the composition ranging from about 0.1% to about 20%.

In some embodiments, the composition further comprises an inactive ingredient. In some embodiments, the inactive ingredient enhances long-term shelf storage or target area absorption. In some embodiments, the inactive ingredient is an emollient/stiffening agents/ointment, an emulsifying agent/solubilizing agent, a humectant, a preservative, a permeation enhancer, a chelating agent, an antioxidant, vehicles/solvents, pH adjusting agents, or a combination thereof.

Example of emollients/stiffening agents include, but are not limited to, carnauba wax, cetyl alcohol, cetostearyl alcohol, cetyl ester wax, emulsifying wax, hydrous lanolin, lanolin, lanolin alcohols, microcrystalline wax, paraffin, petrolatum, polyethylene glycol and polymers thereof, stearic acid, stearyl alcohol, white wax, and yellow wax. Examples of emulsifying agents/solubilizing agents include, but are not limited to, glyceryl monostearate, glyceryl monooleate, glyceryl isostearate, polysorbate 20, polysorbate 60, polysorbate 60, poloxamer, emulsifying wax, sorbitan monostearate, sorbitan monooleate, sodium lauryl sulfate, propylene glycol monostearate, diethylene glycol monoethyl ether, and docusate sodium. Examples of humectants include, but are not limited to, glycerin, propylene glycol, polyethylene glycol, sorbitol solution, and 1,2,6-hexanetriol. Examples of preservatives include, but are not limited to, benzoic acid, propyl paraben, methyl paraben, imidurea, sorbic acid, potassium sorbate, benzalkonium chloride, phenyl mercuric acetate, chlorobutanol, and phenoxyethanol. Examples of permeation enhances include, but are not limited to, propylene glycol, ethanol, isopropyl alcohol, oleic acid, and polyethylene glycol. Examples of chelating agents include, but are not limited to, ethylene diamine tetraacetate. Examples of antioxidants include, but are not limited to butylated hydroxyanisole and butylated hydroxytoluene. Examples of vehicles/solvents include, but are not limited to purified water, hexylene glycol, propylene glycol, oleyl alcohol, propylene carbonate, mineral oil, ethanol, diisopropyl adipate, polyethylene glycol (PEG), and glycerin. Examples of pH adjusting agents include, but are not limited to, acids such as acetic, boric, citric, lactic, phosphoric and hydrochloric acids; and bases such as sodium hydroxide, sodium phosphate, sodium borate, sodium citrate, sodium acetate, sodium bicarbonate, sodium lactate, ammonium chloride, and tris-hydroxymethylaminomethane. In some embodiments, the composition further comprises trolamine.

In some embodiments, the inactive ingredient is an acrylate or polymer thereof, methacrylate or polymer thereof, cellulose polymer, hydroxyethyl cellulose or polymer thereof, poly-lactylate polymer, polyvinyl pyrrolidone polymer, ethylenevinylacetate copolymer, short, medium and long chain fatty acid molecules or analog thereof, isoproprylmyristate, polyethylene terephthalate, vitamin C, vitamin C analog or ester, vitamin E, vitamin E analog, vitamin E polymeric compound, d-α-tocopheryl polyethylene glycol 8.500 succinate (vitamin E TPGS), or silicone.

In some embodiments, the inactive ingredient comprises dual or multiple functionalities. For example, in one embodiment, polyethylene glycol is an emollient, humectant, and a permeation enhancer.

In some embodiments, each component in a composition, such as the ionic liquid, the pharmaceutically acceptable solvent, and optionally other components, is described a percent (%) of the composition. In some embodiments, the % of the composition is a percent concentration volume/volume (v/v), a percent concentration weight/volume (w/v), or a percent concentration weight/weight (w/w). In some embodiments, the % of the composition is a percent concentration weight/weight (w/w) (i.e., % by weight or wt. %).

In some embodiments, the composition comprises the ionic liquid in a concentration of about 0.10% to about 99%. In some embodiments, the composition comprises the ionic liquid in a concentration of about 1% to about 40%. In some embodiments, the composition comprises the ionic liquid in a concentration of about 1% to about 20%. In some embodiments, the composition comprises the ionic liquid in a concentration of about 5% to about 20%. In some embodiments, the composition comprises the ionic liquid in a concentration of about 5% to about 40%. In some embodiments, the composition comprises the ionic liquid in a concentration of about 20% to about 40%. In some embodiments, the composition comprises the ionic liquid in a concentration of about 20% to about 60%. In some embodiments, the composition comprises the ionic liquid in a concentration of about 20% to about 60%.

In some embodiments, the composition comprises the ionic liquid in a concentration of about 0.10% to about 99%, and the pharmaceutically acceptable solvent in a concentration of about 1% to about 99.9%. In some embodiments, the composition comprises the ionic liquid in a concentration of about 1% to about 40%, and the pharmaceutically acceptable solvent in a concentration of about 60% to about 99%. In some embodiments, the composition comprises the ionic liquid in a concentration of about 20% to about 40%, and the pharmaceutically acceptable solvent in a concentration of about 60% to about 99%. In some embodiments, the composition comprises the ionic liquid in a concentration of about 20% and the pharmaceutically acceptable solvent in a concentration of about 60%. In some embodiments, the composition comprises the ionic liquid in a concentration of about 40% and the pharmaceutically acceptable solvent in a concentration of about 60%.

In some embodiments, the composition further comprises ethanol. In some embodiments, the concentration of ethanol in the composition is about 65%, about 75%, about 80%, about 85%, about 90%, or about 95%.

In some embodiments, the composition comprises the ionic liquid in a concentration of about 20% to 40% and a gel base in a concentration of about 20% to 60%. In some embodiments, the composition comprises the ionic liquid in a concentration of 20% and a gel base in a concentration of 60%. In some embodiments, the composition comprises the ionic liquid in a concentration of about 20% to 40%, propylene glycol in a concentration of 20-50%, glycerin in a concentration of 8.5-20%, ethanol in a concentration of about 8.5-20%, and hydroxyl propyl cellulose in a concentration of less than 5%.

In some embodiments, the composition comprises propylene glycol. In some embodiments, the concentration of propylene glycol in the composition is about 0.05%, about 0.1%, about 0.5%, about 1.0%, about 1.5%, about 2.0%, about 2.5%, about 3.0%, about 3.5%, about 4.0%, about 4.5%, or about 5.0%.

In some embodiments, the composition comprises the ionic liquid in a concentration of about 5% to 40% and a gel base comprising the pharmaceutically acceptable solvent in a concentration of about 60% to 95%. In some embodiments, the composition comprises the ionic liquid in a concentration of about 5% to 40%, and a gel base in a concentration of about 60% to 95%, wherein the gel base comprises diisopropyl adipate, propylene glycol, and a poloxamer. In some embodiments, the poloxamer is a Pluronic®.

In some embodiments, the composition comprises the ionic liquid in a concentration of about 1% to 50%, and the pharmaceutically acceptable solvent in a concentration of about 50% to 99%. In some embodiments, the composition comprises the ionic liquid in a concentration of about 1% to 50%, and water in a concentration of about 50% to 99%. In some embodiments, the water is deionized water or Milli-Q® water.

In some embodiments, the composition comprises the ionic liquid in a concentration of about 1% to about 50%, a pharmaceutically acceptable solvent in a concentration of about 1% to 50%, and a gelling agent in a concentration of about 1 to about 5%. In some embodiments, the composition comprises the ionic liquid in a concentration of about 1% to about 50%, water in a concentration of about 1% to 50%, and HPC in a concentration of about 1 to about 5%.

In some embodiments, the pharmaceutically acceptable solvent is diisopropyl adipate. In some embodiments, the composition comprises diisopropyl adipate in a concentration of about 20%. In some embodiments, the composition comprises the ionic liquid in a concentration of about 1% to 40%, and diisopropyl adipate in a concentration of about 60% to about 99%.

In some embodiments, the composition comprises a gel base in a concentration of about 50% to about 85% of the composition. In some embodiments, the composition comprises a gel base in a concentration of about 50%, about 60%, about 70%, about 60%, or about 85% of the composition.

In some embodiments, preparing an ionic liquid comprising a choline cation and a fatty acid anion comprises: (a) mixing choline and a fatty acid in a solvent at room temperature in a predetermined ratio; and (b) removing the solvent in vacuo. In some embodiments, the fatty acid is geranic acid. In some embodiments, the solvent is water. In a particular embodiment, the water is deionized water. In some embodiments, removing the solvent comprises rotary evaporation. In some embodiments, removing the solvent comprises heating the ionic liquid, applying a vacuum to the ionic liquid, or a combination thereof. In some embodiments, preparing the ionic liquid further comprises drying the ionic liquid. In some embodiments, heating the ionic liquid comprises heating the ionic liquid to 60° C. In some embodiments, the heating is done for at least 8.5 minutes, 20 minutes, 30 minutes, 1 hour, 2 hours, 3 hours, 4 hours, 5 hours, 6 hours, 7 hours, 8 hours, 9 hours, 8.5 hours, 11 hours, 12 hours, 24 hours, 36 hours, 48 hours or 60 hours. In some embodiments, the vacuum is applied at −8.50 kPa. In some embodiments, the vacuum is applied for at least 8.5 minutes, 20 minutes, 30 minutes, 1 hour, 2 hours, 3 hours, 4 hours, 5 hours, 6 hours, 7 hours, 8 hours, 9 hours, 8.5 hours, 11 hours, 12 hours, 24 hours, 36 hours, 48 hours or 60 hours.

In some embodiments, the ionic liquid has had the solvent used in the ionic liquid preparation process removed. In some embodiments, the ionic liquid does not comprise water.

In some embodiments, choline is choline bicarbonate. In some embodiments, the choline is choline in a 60% wt. solution of choline bicarbonate. In some embodiment, the predetermined ratio is a ratio of 1:1, 1:2, 1:3, or 1:4 of a choline cation: fatty acid anion. In one embodiment, the ratio is a molar ratio. In another embodiment, the ratio is ratio by weight.

In some embodiments, isolating the composition further comprises purifying the ionic liquid. In some embodiments, purifying the ionic liquid comprises using conventional techniques, including, but not limited to, filtration, distillation, crystallization, and chromatography. In some embodiments, preparing the ionic liquid further comprises isolating the purified ionic liquid.

Dispensing Agents

In another aspect, the sanitizers of the present disclosure may be used in combination with a product, such as a personal care product. More particularly, the sanitizer may be incorporated into or onto a surface, such as a wipe surface, an absorbent surface, a fabric or cloth surface, or a tissue surface, among others. For example, the compositions may be incorporated into personal care products, such as wipes, absorbent articles, bath tissues, cloths, and the like. The sanitizer may be incorporated into wipes such as wipes, hand wipes, face wipes, cosmetic wipes, and the like, or absorbent articles, such as diapers, training pants, adult incontinence products, feminine hygiene products, and the like, and combinations thereof. In one embodiment, the sanitizer is a liquid composition that may be used in combination with a wipe surface to form a wipe or may be a wetting composition for use in combination with a dispersible wipe. In another embodiment, the sanitizer can be used in combination with a wipe surface, which is packaged together with one or more absorbent articles, such as diapers.

In some embodiments, the composition is applied directly to the surface. In some embodiments, the composition is placed on or in an applicator or dispenser, which then applies the composition to the surface. In some embodiments, the applicator or dispenser is a cloth, a wipe, a sponge, a mop, a squirt bottle, a spray bottle, a pump bottle, a tube, an automatic induction hand sterilizer, a bottle or container comprising a dropper, bottle or container comprising a pour spout, or a canister. In some embodiments, the spray bottle is a continuous spray bottle. In some embodiments, the spray bottle is a propellant-free continuous spray bottle. In some embodiments, the continuous spray bottle is a flairosol sprayer. In some embodiments, the spray bottle is an aerosol sprayer. In some embodiments, the spray bottle is a mist spray bottle.

Wipes

In an aspect, provided herein is a wipe, comprising a surface retaining a releasable sanitizing composition, wherein the sanitizing composition comprises an ionic liquid having a cationic component and an anionic component, and wherein the composition is non-irritating to skin.

In an aspect, provided herein is a wipe, comprising a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

In some embodiments, the sanitizer is incorporated into a wetting composition for use in a wipe. The wipe may comprise a nonwoven material that is wetted with an aqueous solution termed the "wetting composition," which may also comprise the sanitizer disclosed herein. As used herein, the nonwoven material comprises a fibrous material or surface, where the fibrous material or surface comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, and solution spinning.

The fibers forming the fibrous material may be made from a variety of materials including natural fibers, synthetic fibers, and combinations thereof. The choice of fibers may depend upon, for example, the intended end use of the finished surface and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wipes. The basis weights for airlaid nonwoven fabrics may range from about 20 to about 200 grams per square meter (gsm) with staple fibers having a denier of about 0.5-8.5 and a length of about 6-15 millimeters. Wipes may generally have a fiber density of about 0.025 g/cc to about 0.2 g/cc. Wipes may generally have a basis weight of about 20 gsm to about 150 gsm. More desirably the basis weight may be from about 30 to about 85 gsm. Even more desirably the basis weight may be from about 50 gsm to about 60 gsm.

Processes for producing airlaid non-woven base sheets are described in, for example, published U.S. Pat. App. No. 2006/0008621, herein incorporated by reference to the extent it is consistent herewith.

The wetting composition for use in combination with the nonwoven materials may desirably comprise the sanitizer of the present disclosure. As noted above, the sanitizer has efficacy against a broad spectrum of microorganisms. As such, the antimicrobial wetting composition will help keep microbiological and fungal growth in the wipe at an acceptable level.

The wetting composition may include a variety of additives or components, including those disclosed in U.S. Patent Publication No. 2002/0155281, which is incorporated herein in its entirety. Possible additives may include, but are not limited to skin-care additives, odor control additives, wetting agents and/or cleaning agents; water, emollients, surfactants, fragrances, preservatives, chelating agents, pH buffers, or combinations thereof as are well known to those skilled in the art. Further, the wetting agent may also contain lotions, medicaments, and/or other antimicrobials.

Relative to the weight of the dry surface, the wipe may desirably contain from about 8.5 percent to about 600 percent of the wetting composition by weight, more desirably from about 50 percent to about 500 percent of the wetting composition by weight, even more desirably from about 70 percent to about 400 percent of the wetting composition by weight.

The wetting composition may be applied to the fibrous material by any known process. Suitable processes for applying the wetting composition include, but are not limited to printing, spraying, electrostatic spraying, the use of metered press rolls or impregnating. The amount of wetting composition may be metered and distributed uniformly onto the fibrous material or may be non-uniformly distributed onto the fibrous material.

For ease of application, the wetting composition may be applied to the fibrous material in combination with a solvent, as a solution or mixture. A variety of solvents may be used, including, for example, water, methanol, ethanol, acetone, or the like. The amount of wetting composition in the solvent may vary, depending on a variety of factors, including the identity and physical characteristics of the fibrous material to which the wetting composition is being applied. The mixture or solution of the wetting composition may contain up to about 50 percent by weight of wetting composition solids. The wetting composition or mixture may contain from about 8.5 to 30 percent by weight of wetting composition solids. Even more desirably, the wetting composition or mixture may contain about 12 to 25 percent by weight wetting composition solids.

Once the wetting composition is applied to the fibrous material, drying, if necessary, may be achieved by any conventional means. Once dry, the nonwoven material may exhibit improved tensile strength when compared to the tensile strength of the untreated wet-laid or dry-laid fibrous material.

The finished wipes may be individually packaged, desirably in a folded condition, in a moisture proof envelope or packaged in containers holding any desired number of sheets in a water-tight package with a wetting composition applied to the wipe. Some example processes which can be used to manufacture folded wipes are described in U.S. Pat. Nos. 5,540,332 and 6,855,748, which are incorporated by reference herein to the extent they are consistent herewith. The finished wipes may also be packaged as a roll of separable sheets in a moisture-proof container holding any desired number of sheets on the roll with a wetting composition applied to the wipes. The roll can be coreless and either hollow or solid. Coreless rolls, including rolls with a hollow center or without a solid center, can be produced with known coreless roll winders, including those of SRP Industry, Inc. (San Jose, Calif); Shimizu Manufacturing (Japan), and the devices disclosed in U.S. Pat. No. 4,667,885. The U.S. Pat. No. 6,651,924 also provides examples of a process for producing coreless rolls of wipes.

Dispensing Agents

In another aspect, the sanitizers of the present disclosure may be used in combination with a product, such as a personal care product. More particularly, the sanitizer may be incorporated into or onto a surface, such as a wipe surface, an absorbent surface, a fabric or cloth surface, or a tissue surface, among others. For example, the compositions may be incorporated into personal care products, such as wipes, absorbent articles, bath tissues, cloths, and the like. The sanitizer may be incorporated into wipes such as wipes, hand wipes, face wipes, cosmetic wipes, and the like, or absorbent articles, such as diapers, training pants, adult incontinence products, feminine hygiene products, and the like, and combinations thereof. In one embodiment, the sanitizer is a liquid composition that may be used in combination with a wipe surface to form a wipe or may be a wetting composition for use in combination with a dispersible wipe. In another embodiment, the sanitizer can be used in combination with a wipe surface, which is packaged together with one or more absorbent articles, such as diapers.

In some embodiments, the composition is applied directly to the surface. In some embodiments, the composition is placed on or in an applicator or dispenser, which then applies the composition to the surface. In some embodiments, the applicator or dispenser is a cloth, a wipe, a sponge, a mop, a squirt bottle, a spray bottle, a pump bottle, a tube, an automatic induction hand sterilizer, a bottle or container comprising a dropper, bottle or container comprising a pour spout, or a canister. In some embodiments, the spray bottle is a continuous spray bottle. In some embodiments, the spray bottle is a propellant-free continuous spray bottle. In some embodiments, the continuous spray bottle is a flairosol sprayer. In some embodiments, the spray bottle is an aerosol sprayer. In some embodiments, the spray bottle is a mist spray bottle.

III. Methods of Use

In an aspect, provided herein is a method of sanitizing a surface, comprising applying to the surface a composition comprising an ionic liquid having a cationic component and an anionic component, wherein the composition is non-irritating to skin.

In another aspect, provided herein is a method of sanitizing a surface, comprising applying to the surface a composition comprising a deep eutectic solvent having a cationic component and an anionic component, wherein the composition is non-irritating to skin, and wherein the deep eutectic solvent has a melting point lower than the melting points of the cationic component and anionic component individually.

In an aspect, provided herein is a method for inhibiting or decreasing microbial growth on a surface, comprising applying to the surface a composition, comprising an ionic liquid having a cationic component and an anionic component, wherein the composition is non-irritating to skin.

In an aspect, provided herein is a method for inhibiting or decreasing microbial growth on a surface, comprising applying to the surface a composition comprising a deep eutectic solvent having a cationic component and an anionic component, wherein the composition is non-irritating to skin, and wherein the deep eutectic solvent has a melting point lower than the melting points of the cationic component and anionic component individually.

In an aspect, provided herein is a method of sanitizing a surface, comprising wiping the surface with a wipe, comprising a surface retaining a releasable sanitizing composition, wherein the sanitizing composition comprises an ionic liquid having a cationic component and an anionic component, and wherein the composition is non-irritating to skin.

In another aspect, provided herein is a method of sanitizing a surface, comprising wiping the surface with a wipe, comprising a surface retaining a releasable sanitizing composition, wherein the sanitizing composition comprises an ionic liquid having a cationic component and an anionic component, and wherein the composition is non-irritating to skin.

In another aspect, provided herein is a method of sanitizing a surface, comprising wiping the surface with a wipe, comprising a surface retaining a releasable sanitizing composition, wherein the sanitizing composition comprises an ionic liquid having a cationic component and an anionic component, and wherein the composition is non-irritating to skin.

In another aspect, provided herein is a method of sanitizing a surface, comprising wiping the surface with a wipe, comprising a surface retaining a releasable sanitizing composition, wherein the sanitizing composition comprises an ionic liquid having a cationic component and an anionic component, and wherein the composition is non-irritating to skin.

In an aspect, provided herein is a method for inhibiting or decreasing microbial growth on a surface, comprising wiping the surface with a wipe, comprising a surface retaining a releasable sanitizing composition, wherein the sanitizing composition comprises an ionic liquid having a cationic component and an anionic component, and wherein the composition is non-irritating to skin.

In an aspect, provided herein is a method for inhibiting or decreasing microbial growth on a surface, comprising wiping the surface with a wipe, comprising a surface retaining a releasable sanitizing composition, wherein the sanitizing composition comprises an ionic liquid having a cationic component and an anionic component, and wherein the composition is non-irritating to skin In an aspect, provided herein is a method of sanitizing a surface, comprising wiping the surface with a wipe, comprising a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

In another aspect, provided herein is a method of sanitizing a surface, comprising wiping the surface with a wipe, comprising a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

In an aspect, provided herein is a method for inhibiting or decreasing microbial growth on a surface, comprising wiping the surface with a wipe, comprising a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

In an aspect, provided herein is a method for inhibiting or decreasing microbial growth on a surface, comprising wiping the surface with a wipe, comprising a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

In some embodiments, the skin is human skin. In some embodiments, the surface is hands of a human subject.

In some embodiments, the composition is rinseless. In some embodiments, at least part of the composition evaporates off of the surface. In some embodiments, the composition remains on the surface for at least about 30 minutes. In some embodiments, the composition remains on the surface for at least about one hours. In some embodiments, the composition remains on the surface for at least about two hours. In some embodiments, the composition remains on the surface for at least about three hours. In some embodiments, the composition remains on the surface for at least about four hours. In some embodiments, the composition remains on the surface for at least about five hours. In some embodiments, the composition remains on the surface for at least about six hours. In some embodiments, the composition remains on the surface for at least about seven hours. In some embodiments, the composition remains on the surface for at least about eight hours. In some embodiments, the composition remains on the surface for at least about nine hours. In some embodiments, the composition remains on the surface for at least about ten hours. In some embodiments, the composition remains on the surface for at least about 11 hours. In some embodiments, the composition remains on the surface for at least about 12 hours. In some embodiments, the composition remains on the surface for at least about 13 hours. In some embodiments, the composition remains on the surface for at least about 14 hours. In some embodiments, the composition remains on the surface for at least about 15 hours. In some embodiments, the composition remains on the surface for at least about 16 hours. In some embodiments, the composition remains on the surface for at least about 17 hours. In some embodiments, the composition remains on the surface for at least about 18 hours. In some embodiments, the composition remains on the surface for at least about 20 hours. In some embodiments, the composition remains on the surface for at least about 22 hours. In some embodiments, the composition remains on the surface for at least about 24 hours. In some embodiments, the composition remains on the surface until cleaned off.

Wetting Agents

In some embodiments, the compositions disclosed herein are formulated as wetting agents (e.g., for wipes).

In some embodiments, at least one of the anionic component and cationic component is irritating to the skin when applied in the absence of the other component.

In some embodiments, the anionic component is bistriflimide, a geranate, an oleate, a hexanoate, dodecyldimethyl ammonia propane sulfonate, N-lauryl sarcosinate, or a geraniolate.

In some embodiments, the cationic component is benzyl pyridinium, benzyl dimethyl dodecyl ammonium, a choline cation, phosphonium, benzethonium, or a phosphonium.

In some embodiments, the phosphonium is a tetraalkyl phosphonium of structural Formula (I): $PR_4$, wherein R is a substituted or unsubstituted alkyl group.

In some embodiments, the cationic component is a choline cation. In some embodiments, the anionic component is a geranate anion.

In some embodiments, the cationic component and the anionic component are in a molar ratio ranging from 1:1 to 1:2 (cationic component to anionic component).

In some embodiments, the composition comprises from about 0.10% to about 40% of choline geranate. In some embodiments, the composition comprises from about 1% to about 10% of choline geranate.

In some embodiments, the composition further comprises pH adjuster, skin conditioner, drying time enhancer, dye, fragrance, gelling agent, humectant, emollient, or combinations thereof. In some embodiments, the alcohol is ethanol, isopropyl alcohol, n-propyl alcohol, or combinations thereof. In some embodiments, the alcohol is present in the composition in an amount of from about 50% to about 95%. In some embodiments, the alcohol is present in the composition in an amount of about 70%.

In some embodiments, the composition further comprises a fragrance agent. In some embodiments, the fragrance agent is an acid or a terpene of a citrus fruit. In some embodiments, the citrus fruit is an orange, a grapefruit, a lime, or a lemon. In some embodiments, the terpene is D-limonene. In some embodiments, the acid is citric acid or a derivative thereof. In some embodiments, the fragrance agent is D-limonene. In some embodiments, the fragrance agent is present in the composition an amount of from about 0.05% to about 5%. In some embodiments, the fragrance agent is present in the composition an amount of from about 0.3% to about 1%.

In some embodiments, the gelling agent is hydroxyethyl cellulose (HEC), hydroxypropyl cellulose (HPC), hydroxypropylmethyl cellulose (HPMC), or a combination thereof. In some embodiments, the gelling agent is HPC. In some embodiments, the gelling agent is present in the composition an amount of from about 0.05% to about 5%. In some embodiments, the gelling agent is present in the composition an amount of from about 0.3% to about 1%.

In some embodiments, the humectant is glycerin. In some embodiments, the humectant is present in the composition an amount of from about 0.5% to about 5%. In some embodiments, the humectant is present in the composition an amount of from about 1% to about 2%.

In some embodiments, the composition further comprises aloe vera.

In some embodiments, the composition further comprises emollients.

In some embodiments, the composition further comprises water, ethanol, diisopropyl adipate, polyethylene glycol (PEG), glycerin, propylene glycol, or a combination thereof.

In some embodiments, the composition further comprises a sporicide and/or an additional antimicrobial agent. In some embodiments, the sporicide is hydrogen peroxide.

In some embodiments, the composition further comprises ethylbenzyl ammonium choride, benzalkonium chloride, denatured alcohol, PEG-8 dimethicone, phenoxyethanol, quaternium-52, potassium sorbate, sodium capryloamphopropionate, methylparaben, citric acid, disodium EDTA, ethylparaben, PEG-60 lanolin, propylparaben, Aloe Barbadensis leaf juice, acrylates $C_{10-30}$ alkyl acrylate crosspolymer, benzophenone-4, glycerin, tocopherol, dipropylene glycol butyl ether, citric acid, sodium methyl 2-sulfolaurate, $C_{10}$ ethoxylated alcohol, $C_{10-16}$ alkyl glucoside, 2,6-dimethyl-2-heptanol, alpha-methylbenzyl acetate, dihydromyrcenol, dipropylene glycol, ethylene brassylate, gamma-decalactone, tricyclodecenyl propionate, sodium sulfate, or any combination thereof In some embodiments, the ionic liquid comprises the choline cation and geranic acid anion in a molar ratio of 1:1 or 1:2 of choline cation to geranic acid anion. In some embodiments, the ionic liquid comprises the choline cation and geranic acid anion in a molar ratio in a range of 1:1 to 1:4 of choline cation to geranic acid anion. In some embodiments, the ionic liquid comprises the choline cation and geranic acid anion in a molar ratio of 1:1, 1:2, 1:3, or 1:4 of choline cation to geranic acid anion. In some embodiments, the composition provides an increased antimicrobial action compared to an antimicrobial action of choline or an antimicrobial action of geranic acid. In some embodiments, the increased antimicrobial action is a 10 fold less concentration of the composition required for complete killing of a microbe relative to a concentration of choline or a concentration of geranic acid required for complete killing of the microbe. In some embodiments, the ionic liquid comprises a concentration of about 0.1% to 99% of the composition, and the pharmaceutically acceptable solvent comprises a concentration of about 1% to about 99.9% of the composition.

In some embodiments, the composition is formulated as a liquid, gel, cream, foam, lotion, cream, wetting composition, or a spray. In some embodiments, the composition is formulated for topical administration. In some embodiments, the composition is formulated as a gel.

Microbes

In some embodiments, the compositions of the present disclosure slow the spread of gram-positive and/or gram-negative bacteria, fungi, mold, viruses, protozoans, parasites, and other microbes. In some embodiments, the compositions of the present disclosure prevent or slow contamination of a surface with gram-positive and/or gram-negative bacteria, fungi, mold, viruses, protozoans, parasites, and other microbes.

In some embodiments, the microbial growth is growth of a virus, bacterium, fungus, mold, protozoan, parasite, or combinations thereof.

In some embodiments, the bacterium is a gram-negative bacterium. In some embodiments, the gram-negative bacterium is an *Escherichia, Salmonella, Klebsiella* bacterium, or any combination thereof. In some embodiments, the *Escherichia* bacterium is *E. coli.*

In some embodiments, the gram-positive bacterium is a *Staphylococcus* or *Streptococcus* bacterium. In some embodiments, the *Staphylococcus* bacterium is *S. aureus*. In some embodiments, the *Staphylococcus* bacterium is methicillin-resistant *S. aureus* (MRSA). In some embodiments, the bacterium is *S. enterica, S. pyogenes, K. pneumoniae*, or any combination thereof.

In some embodiments, the virus is in Coronaviridae family. In some embodiments, the virus is in Orthocoronaviridae subfamily. In some embodiments, the virus is a Betacoronavirus (0-CoV). In some embodiments, the virus is a Sarbecovirus. In some embodiments, the virus is an Ebolavirus, Coronavirus, Rotavirus, Alphainfluenzavirus, Betainfluenzavirus, Deltainfluenzavirus, and/or Gammainfluenzavirus.

In some embodiments, the virus is a human virus. In some embodiments, the virus is severe acute respiratory syndrome coronavirus 2 (SARS-CoV-2). In some embodiments, the virus is human severe acute respiratory syndrome coronavirus 2 (SARS-CoV-2). In some embodiments, the virus is Influenza A, B, and/or C. In some embodiments, the virus is Influenza A2 virus.

Non-Limiting Embodiments

Embodiment 1. A method of sanitizing a surface, comprising applying to the surface a composition comprising an ionic liquid having a cationic component and an anionic component, wherein the composition is non-irritating to skin.

Embodiment 2. A method of sanitizing a surface, comprising applying to the surface a composition comprising a deep eutectic solvent having a cationic component and an anionic component, wherein the composition is non-irritating to skin, and wherein the deep eutectic solvent has a melting point lower than the melting points of the cationic component and anionic component individually.

Embodiment 3. A method of sanitizing a surface, comprising applying to the surface a composition comprising an alcohol and a non-volatile component, wherein the composition is non-irritating to skin.

Embodiment 4. A method for inhibiting or decreasing microbial growth on a surface, comprising applying to the surface a composition comprising an ionic liquid having a cationic component and an anionic component, wherein the composition is non-irritating to skin.

Embodiment 5. A method for inhibiting or decreasing microbial growth on a surface, comprising applying to the surface a composition comprising a deep eutectic solvent having a cationic component and an anionic component, wherein the composition is non-irritating to skin, and wherein the deep eutectic solvent has a melting point lower than the melting points of the cationic component and anionic component individually.

Embodiment 6. A method for inhibiting or decreasing microbial growth on a surface, comprising applying to the surface a composition comprising alcohol and a non-volatile component, wherein the composition is non-irritating to skin.

Embodiment 7. The method of embodiment 3 or 6, wherein the non-volatile component is a polymer, peptide, dendrimer, ionic liquid, or deep eutectic solvent, or combinations thereof.

Embodiment 8. The method of embodiment 7, wherein the polymer is a poly(styrene), poly(vinylpyridine), poly(vinyl alcohol), polymethacrylate, or combinations thereof.

Embodiment 9. The method of embodiment 7, wherein the non-volatile component is an AMP-mimicking polyurethane, quaternary ammonium-containing poly (dimethylaminoethyl), methacrylate with natural resin, cationic polyester-based polymer, poly(amidoamine)-dendrimer (PAMAM-dendrimer), or poly(propylene imine)-dendrimer (PPI-dendrimer).

Embodiment 10. The method of any one of embodiments 3 or 6-9, wherein the non-volatile component is an anti-microbial agent.

Embodiment 11. The method of any one of embodiments 3 or 6-7, wherein the non-volatile component is an antimicrobial peptide (AMP) or polymer disinfectant/biocide.

Embodiment 12. The method of embodiment 11, wherein the polymer is a peptide-mimetic antimicrobial polymer.

Embodiment 13. The method of embodiment 11, wherein the polymer comprises a quaternary ammonium salt (QAS) and (C8-C12) alkyl chain(s).

Embodiment 14. The method of embodiment 7, wherein the polymer is a nylon, nylon-type synthetic polymer, polycarbonate, polynorbomene, vinyl polymer, co-polymer, a cationic polymer, polyurethane, guanide or biguanide polymer, dendrimer or combinations thereof.

Embodiment 15. The method of embodiment 14, wherein the biguanide polymer is polyhexamethylene biguanide (PHMB).

Embodiment 16. The method of embodiment 14, wherein the co-polymer comprises a hydrophobic side chain and cationic group.

Embodiment 17. The method of embodiment 14, wherein the co-polymer comprises a poly(vinyl) ether, methacrylate, or methacrylamide, arylamide, or polymethacrylate, cationic ammonium, hydrophobic alkyl, or neutral hydroxyl side chain monomer/constituent unit.

Embodiment 18. The method of embodiment 14, wherein the cationic polymer is amino-ethyl methacrylate (AEMA).

Embodiment 19. The method of embodiment 14, wherein the hydrophobic alkyl is ethyl methacrylate (EMA).

Embodiment 20. The method of embodiment 14, wherein the neutral hydroxyl is hydroxyethyl methacrylate (HEMA).

Embodiment 21. The method of embodiment 14, wherein the methacrylamide is 3-guanidinopropyl methacrylamide (GPMA), N-(3-aminopropyl)methacrylamide hydrochloride (APMA), or poly(N-(3-aminopropyl) methacrylamide) (PAPMA).

Embodiment 22. The method of any one of embodiments 14-21, wherein the co-polymer is amphilic.

Embodiment 23. The method of embodiment 7, wherein the non-volatile component is an ionic liquid or deep eutectic solvent.

Embodiment 24. The method of embodiment 23, wherein the ionic liquid has a cationic component and an anionic component.

Embodiment 25. The method of embodiment 43, wherein the deep eutectic solvent has a cationic component and an anionic component, wherein the composition is non-irritating to skin, and wherein the deep eutectic solvent has a melting point lower than the melting points of the cationic component and anionic component individually Embodiment 26. The method of any one of embodiments 4-6, wherein the microbial growth is growth of a virus, bacterium, fungus, mold, protozoan, parasite, or combinations thereof.

Embodiment 27. The method of embodiment 26, wherein the bacterium is a gram-negative bacterium.

Embodiment 28. The method of embodiment 27, wherein the gram-negative bacterium is an *Escherichia, Salmonella, Klebsiella* bacterium, or any combination thereof.

Embodiment 29. The method of embodiment 28, wherein the *Escherichia* bacterium is *E. coli.*

Embodiment 30. The method of embodiment 26, wherein the bacterium is a gram-positive bacterium.

Embodiment 31. The method of embodiment 30, wherein the gram-positive bacterium is a *Staphylococcus* or *Streptococcus* bacterium.

Embodiment 32. The method of embodiment 31, wherein the *Staphylococcus* bacterium is methicillin-resistant *S. aureus* (MRSA).

Embodiment 33. The method of any embodiment 26, wherein the virus is an Ebolavirus, Coronavirus, Rotavirus, Alphainfluenzavirus, Betainfluenzavirus, Deltainfluenzavirus, Gammainfluenzavirus, or any combination thereof.

Embodiment 34. The method of any one of embodiments 4-6 or 33, wherein the virus is a Coronavirus.

Embodiment 35. The method of embodiment 33, wherein the Coronavirus is severe acute respiratory syndrome coronavirus 2 (SARS-CoV-2).

Embodiment 36. The method of any one of embodiments 4-6 or 33-35, wherein the virus is a human virus.

Embodiment 37. The method of any one of embodiments 1-2, 4-5, and 24-36, wherein at least one of the anionic component and cationic component is irritating to the skin when applied in the absence of the other component.

Embodiment 38. The method of any one of embodiments 1-2, 4-5, and 24-36, wherein the anionic component is bistriflimide, a geranate, an oleate, a hexanoate, dodecyldimethyl ammonia propane sulfonate, N-lauryl sarcosinate, or a geraniolate.

Embodiment 39. The method of any one of embodiments 1-2, 4-5, and 24-38, wherein the cationic component is benzyl pyridinium, benzyl dimethyl dodecyl ammonium, a choline cation, phosphonium, benzethonium, or a phosphonium.

Embodiment 40. The method of embodiment 38, wherein the phosphonium is a tetraalkyl phosphonium of structural Formula (I): PR4, wherein R is a substituted or unsubstituted alkyl group.

Embodiment 41. The method of any one of embodiments 1-2, 4-5, and 24-40, wherein the cationic component is a choline cation.

Embodiment 42. The method of any one of embodiments 1-2, 4-5, and 24-41, wherein the anionic component is a geranate anion Embodiment 43. The method of any one of embodiments 1-2, 4-5, and 24-42, wherein the cationic component and the anionic component are in a molar ratio ranging from 1:1 to 1:2 (cationic component to anionic component).

Embodiment 44. The method of embodiment 42 or 43, wherein the composition comprises from about 0.1% to about 40% of choline geranate by weight.

Embodiment 45. The method of any one of embodiments 42-44, wherein the composition comprises from about 1% to about 8.5% of choline geranate by weight.

Embodiment 46. The method of any one of embodiments 1-45, wherein the composition further comprises pH adjuster, skin conditioner, drying time enhancer, dye, fragrance, gelling agent, humectant, emollient, antioxidant, or combinations thereof.

Embodiment 47. The method of any one of embodiments 1-46, wherein the composition further comprises an alcohol.

Embodiment 48. The method of embodiment 46 or 47, wherein the alcohol is ethanol, isopropyl alcohol, n-propyl alcohol, or combinations thereof.

Embodiment 49. The method of any one of embodiments 47-48, wherein the alcohol is present in the composition in an amount of from about 50% to about 95% by weight.

Embodiment 50. The method of any one of embodiments 47-49, wherein the alcohol is present in the composition in an amount of about 70% by weight.

Embodiment 51. The method of any one of embodiments 46-50, wherein the fragrance is D-limonene.

Embodiment 52. The method of any one of embodiments 46-51, wherein the fragrance is present in the composition an amount of from about 0.05% to about 5% by weight.

Embodiment 53. The method of any one of embodiments 46-52, wherein the fragrance is present in the composition an amount of from about 0.3% to about 1%.

Embodiment 54. The method of any one of embodiments 46-53, wherein the gelling agent is hydroxypropyl cellulose.

Embodiment 55. The method of any one of embodiments 46-54, wherein the gelling agent is present in the composition an amount of from about 0.05% to about 5% by weight.

Embodiment 56. The method of any one of embodiments 46-55, wherein the gelling agent is present in the composition an amount of from about 0.3% to about 1% by weight.

Embodiment 57. The method of any one of embodiments 46-56, wherein the humectant is glycerin.

Embodiment 58. The method of any one of embodiments 46-57, wherein the humectant is present in the composition an amount of from about 0.5% to about 5% by weight.

Embodiment 59. The method of any one of embodiments 46-58, wherein the humectant is present in the composition an amount of from about 1% to about 2% by weight.

Embodiment 60. The method of any one of embodiments 1-59, wherein the composition further comprises aloe vera.

Embodiment 61. The method of any one of embodiments 1-61, wherein the composition further comprises emollients.

Embodiment 62. The method of any one of embodiments 1-61, wherein the composition further comprises water.

Embodiment 63. The method of any one of embodiments 1-62, wherein the composition further comprises ethylbenzyl ammonium choride, benzalkonium chloride, denatured alcohol, PEG-8 dimethicone, phenoxyethanol, quaternium-52, potassium sorbate, sodium capryloamphopropionate, methylparaben, citric acid, disodium EDTA, ethylparaben, PEG-60 lanolin, propylparaben, Aloe Barbadensis leaf juice, acrylates C10-30 alkyl acrylate crosspolymer, benzophenone-4, glycerin, tocopherol, dipropylene glycol butyl ether, citric acid, sodium methyl 2-sulfolaurate, C10 ethoxylated alcohol, C10-16 alkyl glucoside, 2,6-dimethyl-2-heptanol, alpha-methylbenzyl acetate, dihydromyrcenol, dipropylene glycol, ethylene brassylate, gamma-decalactone, tricyclodecenyl propionate, sodium sulfate, or any combination thereof.

Embodiment 64. The method of any one of embodiments 1-63, wherein the composition is in the form of a liquid, a gel, a foam, a lotion, or a soap.

Embodiment 65. The method of embodiment any of embodiments 1-64, wherein the surface is a not a hard or a solid surface.

Embodiment 66. The method of any one of embodiments 1-65, wherein the surface is a skin surface.

Embodiment 67. The method of embodiment 66, wherein the skin is human skin.

Embodiment 68. The method of embodiment 67, wherein the surface is the hands of a subject.

Embodiment 69. The method of any one of embodiments 1-68, wherein the composition is applied directly to the surface.

Embodiment 70. The method of any one of embodiments 1-69, wherein the composition is placed on or in an applicator or dispenser, which then applies the composition to the surface.

Embodiment 71. The method of embodiment 70, wherein the applicator or dispenser is a cloth, a wipe, a sponge, a mop, a squirt bottle, a spray bottle, a pump bottle, a tube, an automatic induction hand sterilizer, a bottle or container comprising a dropper, bottle or container comprising a pour spout, or a canister.

Embodiment 72. The method of embodiment 71, wherein the spray bottle is a continuous spray bottle, a propellant-free continuous spray bottle, a flairosol sprayer, an aerosol sprayer, or a mist spray bottle.

Embodiment 73. The method of any one of embodiments 1-72, wherein the composition is rinseless.

Embodiment 74. A wipe, comprising:

a surface retaining a releasable sanitizing composition, wherein the sanitizing composition comprises an ionic liquid having a cationic component and an anionic component, and wherein the composition is non-irritating to skin.

Embodiment 75. A wipe, comprising:

a surface retaining a releasable sanitizing composition, wherein the sanitizing composition comprises a deep eutectic solvent having a cationic component and an anionic component, wherein the composition is non-irritating to skin, and wherein the deep eutectic solvent has a melting point lower than the melting points of the cationic component and anionic component individually.

Embodiment 76. The wipe of any one of 74 or 75, wherein at least one of the anionic component and cationic component is irritating to the skin when applied in the absence of the other component.

Embodiment 77. The wipe of any one of embodiments 74-76, wherein the anionic component is bistriflimide, a geranate, an oleate, a hexanoate, dodecyldimethyl ammonia propane sulfonate, N-lauryl sarcosinate, or a geraniolate.

Embodiment 78. The wipe of any one of embodiments 74-77, wherein the cationic component is benzyl pyridinium, benzyl dimethyl dodecyl ammonium, a choline cation, phosphonium, benzethonium, or a phosphonium.

Embodiment 79. The wipe of embodiment 78, wherein the phosphonium is a tetraalkyl phosphonium of structural Formula (I): PR4, wherein R is a substituted or unsubstituted alkyl group.

Embodiment 80. The wipe of any one of embodiments 74-79, wherein the cationic component is a choline cation.

Embodiment 81. The wipe of any one of embodiments 74-80, wherein the anionic component is a geranate anion Embodiment 82. The wipe of any one of embodiments 74-81, wherein the cationic component and the anionic component are in a molar ratio ranging from 1:1 to 1:2 (cationic component to anionic component).

Embodiment 83. The wipe of embodiment 81 or 82, wherein the composition comprises from about 0.1% to about 40% of choline geranate.

Embodiment 84. The wipe of any one of embodiments 81-83, wherein the composition comprises from about 1% to about 8.5% of choline geranate.

Embodiment 85. The wipe of any one of embodiments 74-84, wherein the composition further comprises pH adjuster, skin conditioner, drying time enhancer, dye, fragrance, gelling agent, humectant, emollient, foaming agent, an antioxidant, or combinations thereof.

Embodiment 86. The wipe of any one of embodiments 74-85, wherein the composition further comprises an alcohol.

Embodiment 87. The wipe of embodiment 86, wherein the alcohol is ethanol, iso-propyl alcohol, n-propyl alcohol, or combinations thereof.

Embodiment 88. The wipe of any embodiment 86 or 87, wherein the alcohol is present in the composition in an amount of from about 50% to about 95% by weight.

Embodiment 89. The wipe of any one of embodiments 86-88, wherein the alcohol is present in the composition in an amount of about 70% by weight.

Embodiment 90. The wipe of any one of embodiments 85-88, wherein the fragrance is D-limonene.

Embodiment 91. The wipe of any one of embodiments 85-89, wherein the fragrance is present in the composition an amount of from about 0.05% to about 5% by weight.

Embodiment 92. The wipe of any one of embodiments 85-91, wherein the fragrance is present in the composition an amount of from about 0.3% to about 1% by weight.

Embodiment 93. The wipe of any one of embodiments 85-92, wherein the gelling agent is hydroxypropyl cellulose.

Embodiment 94. The wipe of any one of embodiments 85-93, wherein the gelling agent is present in the composition an amount of from about 0.05% to about 5% by weight.

Embodiment 95. The wipe of any one of embodiments 85-94, wherein the gelling agent is present in the composition an amount of from about 0.3% to about 1% by weight.

Embodiment 96. The wipe of any one of embodiments 85-95, wherein the humectant is glycerin.

Embodiment 97. The wipe of any one of embodiments 85-96, wherein the humectant is present in the composition an amount of from about 0.5% to about 5% by weight.

Embodiment 98. The wipe of any one of embodiments 84-96, wherein the humectant is present in the composition an amount of from about 1% to about 2% by weight.

Embodiment 99. The wipe of any one of embodiments 74-99, wherein the composition further comprises aloe vera.

Embodiment 100. The wipe of any one of embodiments 74-99, wherein the composition further comprises emollients.

Embodiment 101. A method of sanitizing a surface, comprising wiping the surface with the wipe of any one of embodiments 74-100.

Embodiment 102. A method for inhibiting or decreasing microbial growth on a surface, comprising wiping the surface with the wipe of any one of embodiments 74-100.

Embodiment 103. The method of embodiment 102, wherein the microbial growth is growth of a virus, bacterium, fungus, mold, protozoan, parasite, or combinations thereof.

Embodiment 104. The method of embodiment 103, wherein the bacterium is a gram-negative bacterium.

Embodiment 105. The method of embodiment 104, wherein the gram-negative bacterium is an *Escherichia, Salmonella, Klebsiella* bacterium, or any combination thereof.

Embodiment 106. The method of embodiment 105, wherein the *Escherichia* bacterium is *E. coli.*

Embodiment 107. The method of embodiment 103, wherein the bacterium is a gram-positive bacterium.

Embodiment 108. The method of embodiment 107, wherein the gram-positive bacterium is a *Staphylococcus* or *Streptococcus* bacterium.

Embodiment 109. The method of embodiment 108, wherein the *Staphylococcus* bacterium is methicillin-resistant *S. aureus* (MRSA).

Embodiment 110. The method of embodiment 109, wherein the virus is an Ebolavirus, Coronavirus, Rotavirus, Alphainfluenzavirus, Betainfluenzavirus, Deltainfluenzavirus, Gammainfluenzavirus, or any combination thereof.

Embodiment 111. The method of embodiment 103 or 109, wherein the virus is a Coronavirus.

Embodiment 112. The method of any one of embodiments 103 or 110-111, wherein the virus is a human virus.

Embodiment 113. The method of any one of embodiments 103 or 110-112, wherein the virus is severe acute respiratory syndrome coronavirus 2 (SARS-CoV-2).

Embodiment 114. The wipe or method of any of embodiments 101-113, wherein the surface is porous.

Embodiment 115. The wipe or method of any of embodiments 101-114, wherein the surface is non-porous.

Embodiment 116. The method of embodiment any of embodiments 101-115, wherein the surface is not a hard or a solid surface.

Embodiment 117. The method of any one of embodiments 101-113, wherein the surface is a skin surface.

Embodiment 118. The method of embodiment 117, wherein the skin is human skin.

Embodiment 119. The method of embodiment 118, wherein the surface is the hands of a subject.

Embodiment 120. The wipe or method of any one of embodiments 1-119, wherein at least part of the composition evaporates off of the surface.

Embodiment 121. The wipe or method of any one of embodiments 1-120, wherein the composition further comprises a sporicide and/or additional antimicrobial agent.

Embodiment 122. The wipe or method of embodiment 121, wherein the sporicide is hydrogen peroxide.

Embodiment 123. The wipe or method of any one of embodiments 1-122, wherein the composition remains on the surface for at least two hours.

Embodiment 124. The wipe or method of any one of embodiments 1-123, wherein the composition remains on the surface for at least four hours.

Embodiment 125. The wipe or method of any one of embodiments 1-124, wherein the composition remains on the surface until cleaned or washed off.

Embodiment 126. A sanitizing composition, comprising alcohol and a non-volatile component, wherein the composition is non-irritating to skin.

Embodiment 127. The sanitizing composition of embodiment 126, wherein the non-volatile component is a polymer, peptide, ionic liquid, deep eutectic solvent, or combinations thereof.

Embodiment 128. The sanitizing composition of embodiment 127, wherein the polymer is a poly(styrene), poly(vinylpyridine), poly(vinyl alcohol), polymethacrylate, or combinations thereof.

Embodiment 129. The sanitizing composition of embodiment 127, wherein the non-volatile component is an AMP-mimicking polyurethane, quaternary ammonium-containing poly(dimethylaminoethyl), methacrylate with natural resin, cationic polyester-based polymer, poly(amidoamine)-dendrimer (PAMAM-dendrimer), or poly(propylene imine)-dendrimer (PPI-dendrimer).

Embodiment 130. The sanitizing composition of any one of embodiments 126-129, wherein the non-volatile component is an anti-microbial agent.

Embodiment 131. The sanitizing composition of embodiment 126-130, wherein the non-volatile component is an antimicrobial peptide (AMP) or polymer disinfectant/biocide.

Embodiment 132. The sanitizing composition of embodiment 131, wherein the polymer is a peptide-mimetic antimicrobial polymer.

Embodiment 133. The sanitizing composition of embodiment 132, wherein the polymer comprises a quaternary ammonium salt (QAS) and (C8-C12) alkyl chain(s).

Embodiment 134. The sanitizing composition of embodiment 127, wherein the polymer is a nylon, nylon-type synthetic polymer, polycarbonate, polynorbomene, vinyl polymer, co-polymer, a cationic polymer, polyurethane, guanide or biguanide polymer, dendrimer or combinations thereof.

Embodiment 135. The sanitizing composition of embodiment 134, wherein the biguanide polymer is polyhexamethylene biguanide (PHMB).

Embodiment 136. The sanitizing composition of embodiment 134, wherein the co-polymer comprises a hydrophobic side chain and cationic group.

Embodiment 137. The sanitizing composition of embodiment 134, wherein the co-polymer comprises a poly (vinyl) ether, methacrylate, or methacrylamide, arylamide, or polymethacrylate, cationic ammonium, hydrophobic alkyl, or neutral hydroxyl side chain monomer/constituent unit.

Embodiment 138. The sanitizing composition of embodiment 134, wherein the cationic ammonium is aminoethyl methacrylate: (AEMA).

Embodiment 139. The sanitizing composition of embodiment 134, wherein the hydrophobic alkyl is ethyl methacrylate (EMA).

Embodiment 140. The sanitizing composition of embodiment 134, wherein the neutral hydroxyl is hydroxyethyl methacrylate (HEMA).

Embodiment 141. The sanitizing composition of embodiment 134, wherein the methacrylamide is 3-guanidinopropyl methacrylamide (GPMA), N-(3-aminopropyl) methacrylamide hydrochloride (APMA), or poly(N-(3-aminopropyl)methacrylamide) (PAPMA).

Embodiment 142. The sanitizing composition of any one of embodiments 134-141, wherein the co-polymer is amphilic.

Embodiment 143. The sanitizing composition of embodiment 127, wherein the non-volatile component is an ionic liquid or deep eutectic solvent.

Embodiment 144. The sanitizing composition of embodiment 143, wherein the ionic liquid has a cationic component and an anionic component.

Embodiment 145. The sanitizing composition of embodiment 143, wherein the deep eutectic solvent has a cationic component and an anionic component, wherein the composition is non-irritating to skin, and wherein the deep eutectic solvent has a melting point lower than the melting points of the cationic component and anionic component individually Embodiment 146. The sanitizing composition of embodiment 144 or 145, wherein at least one of the anionic component and cationic component is irritating to the skin when applied in the absence of the other component.

Embodiment 147. The sanitizing composition of any one of embodiments 144-146, wherein the anionic component is bistriflimide, a geranate, an oleate, a hexanoate, dodecyldimethyl ammonia propane sulfonate, N-lauryl sarcosinate, or a geraniolate.

Embodiment 148. The sanitizing composition of any one of embodiments 144-148, wherein the cationic component is benzyl pyridinium, benzyl dimethyl dodecyl ammonium, a choline cation, phosphonium, benzethonium, or a phosphonium.

Embodiment 149. The sanitizing composition of embodiment 148, wherein the phosphonium is a tetraalkyl phosphonium of structural Formula (I): PR4, wherein R is a substituted or unsubstituted alkyl group.

Embodiment 150. The sanitizing composition of any one of embodiments 144-149, wherein the cationic component is a choline cation.

Embodiment 151. The sanitizing composition of any one of embodiments 144-150, wherein the anionic component is a geranate anion Embodiment 152. The sanitizing composition of any one of embodiments 144-151, wherein the cationic component and the anionic component are in a molar ratio ranging from 1:1 to 1:2 (cationic component to anionic component).

Embodiment 153. The sanitizing composition of embodiment 151 or 152, wherein the composition comprises from about 0.10% to about 40% of choline geranate by weight.

Embodiment 154. The sanitizing composition of any one of embodiments 151-153, wherein the composition comprises from about 1% to about 8.5% of choline geranate by weight.

Embodiment 155. The sanitizing composition of any one of embodiments 126-154, wherein the composition further comprises pH adjuster, skin conditioner, drying time enhancer, dye, fragrance, gelling agent, humectant, emollient, antioxidant, or combinations thereof.

Embodiment 156. The sanitizing composition of any one of embodiments 126-155, wherein the composition further comprises an alcohol.

Embodiment 157. The sanitizing composition of embodiment 156, wherein the alcohol is ethanol, isopropyl alcohol, n-propyl alcohol, or combinations thereof.

Embodiment 158. The sanitizing composition of 156 or 157, wherein the alcohol is present in the composition in an amount of from about 50% to about 95% by weight.

Embodiment 159. The sanitizing composition of any one of embodiments 156-158, wherein the alcohol is present in the composition in an amount of about 70% by weight.

Embodiment 160. The sanitizing composition of any one of embodiments 155-159, wherein the fragrance is D-limonene.

Embodiment 161. The sanitizing composition of any one of embodiments 155-160, wherein the fragrance is present in the composition an amount of from about 0.05% to about 5% by weight.

Embodiment 162. The sanitizing composition of any one of embodiments 155-161, wherein the fragrance is present in the composition an amount of from about 0.3% to about 1%.

Embodiment 163. The sanitizing composition of any one of embodiments 155-162, wherein the gelling agent is hydroxypropyl cellulose.

Embodiment 164. The sanitizing composition of any one of embodiments 155-163, wherein the gelling agent is present in the composition an amount of from about 0.05% to about 5% by weight.

Embodiment 165. The sanitizing composition of any one of embodiments 155-164, wherein the gelling agent is present in the composition an amount of from about 0.3% to about 1% by weight.

Embodiment 166. The sanitizing composition of any one of embodiments 155-165, wherein the humectant is glycerin.

Embodiment 167. The sanitizing composition of any one of embodiments 155-166, wherein the humectant is present in the composition an amount of from about 0.5% to about 5% by weight.

Embodiment 168. The sanitizing composition of any one of embodiments 155-167, wherein the humectant is present in the composition an amount of from about 1% to about 2% by weight.

Embodiment 169. The sanitizing composition of any one of embodiments 126-168, wherein the composition further comprises aloe vera.

Embodiment 170. The sanitizing composition of any one of embodiments 126-169, wherein the composition further comprises emollients.

Embodiment 171. The sanitizing composition of any one of embodiments 126-170, wherein the composition further comprises water.

Embodiment 172. The sanitizing composition of any one of embodiments 126-171, wherein the composition further comprises ethylbenzyl ammonium choride, benzalkonium chloride, denatured alcohol, PEG-8 dimethicone, phenoxyethanol, quaternium-52, potassium sorbate, sodium capryloamphopropionate, methylparaben, citric acid, disodium EDTA, ethylparaben, PEG-60 lanolin, propylparaben, Aloe Barbadensis leaf juice, acrylates C10-30 alkyl acrylate crosspolymer, benzophenone-4, glycerin, tocopherol, dipropylene glycol butyl ether, citric acid, sodium methyl 2-sulfolaurate, C10 ethoxylated alcohol, C10-16 alkyl glucoside, 2,6-dimethyl-2-heptanol, alpha-methylbenzyl acetate, dihydromyrcenol, dipropylene glycol, ethylene brassylate, gamma-decalactone, tricyclodecenyl propionate, sodium sulfate, or any combination thereof.

Embodiment 173. The sanitizing composition of any one of embodiments 126-172, wherein the composition is in the form of a liquid, a gel, a foam, a lotion, a soap, or wetting solution.

Embodiment 174. The sanitizing composition of any one of embodiments 126-173, wherein the sanitizing composition is stored in a container, dispenser or applicator, or is applied to a textile.

Embodiment 175. The sanitizing composition of embodiment 174, wherein the applicator or dispenser is a squirt bottle, a spray bottle, a pump bottle, a tube, an automatic induction hand sterilizer, a bottle or container comprising a dropper, bottle or container comprising a pour spout, or a canister.

Embodiment 176. The sanitizing composition of embodiment 175, wherein the spray bottle is a continuous spray bottle, a propellant-free continuous spray bottle, a flairosol sprayer, an aerosol sprayer, or a mist spray bottle.

Embodiment 177. The sanitizing composition of embodiment 174, wherein the textile is cloth, a wipe, a sponge, a wound dressing, or a mop.

Embodiment 178. The sanitizing composition of any one of embodiments 126-177, wherein the composition is rinseless.

Embodiment 179. The sanitizing composition of any one of embodiments 126-178, wherein the composition further comprises a sporicide and/or additional antimicrobial agent.

Embodiment 180. The sanitizing composition of embodiment 179, wherein the sporicide is hydrogen peroxide.

Embodiment 181. The sanitizing composition of any one of embodiments 126-180, wherein the composition is formulated to remain on a surface for at least two hours.

Embodiment 182. The sanitizing composition of any one of embodiments 126-181, wherein the composition is formulated to remain on a surface for at least four hours.

Embodiment 183. The sanitizing composition of any one of embodiments 126-182, wherein the composition is formulated to remain on a surface until rinsed or washed off.

Embodiment 184. The sanitizing composition of any one of embodiments 181-183, wherein the surface is not hard or a solid surface.

Embodiment 185. The sanitizing composition of any one of embodiments 181-184, wherein the surface is a porous or non-porous surface.

Embodiment 186. The sanitizing composition of any one of embodiments 181-183, wherein the surface is skin.

Embodiment 187. The method of embodiment 186, wherein the skin is human skin.

EXAMPLES

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Example 1: Evaluation of Residual Antimicrobial Efficacy of Sanitizer a Containing 5% CAGE 1:2 (Choline:Geranate=1:2)

The purpose of this experiment was to demonstrate the persistent antibacterial efficacy of Sanitizer A containing 5% CAGE 1:2 (CGB-S-100) on human skin at 30 min, 2, and 4 hours after application.

This study was conducted to measure the persistence of antibacterial activity of 5% CAGE 1:2 hand sanitizer and to compare it to the marketed alcohol-based hand sanitizer Purell® Advance. The persistence of antibacterial activity on human finger pads was measured against *Escherichia coli* (*E. coli*) using a technique described in American Society for Testing and Materials protocol E2276-10(2019) at up to 4 hours after application. The antibacterial activity was determined visually by the difference between the number of challenge bacteria species grown on Tryptic Soy Agar (TSA) plates following the inoculate exposure to the test article, comparator and the number grown from the untreated/saline treated (negative control) test sites on the skin.

The first in-vivo trial included 5 subjects (18-50 years old) with healthy skin (3 men and 2 women).

Test groups were:

1. Saline (negative control),
2. Purell® Advance Gel,
3. CGB-S-100. Lot #012-040. The TSA plates utilized for this study were prepared in the lab in the cell culture hood. The subject's fingers were randomized to avoid anatomical bias as described in Table 1.

500 μL of Test Articles or Control were applied on finger pads and were gently rubbed onto the skin. 10 μL of freshly prepared *E. coli* suspension was applied to the treated finger pad at predetermined time points. After inoculation the bacterial suspension was allowed to dry for 60 seconds (s). After 60 s the finger pad was pressed onto the agar plate and left at 37° C. for 24 hrs. All the inoculation and test applications were performed in Biological Safety Cabinets.

Growth of *E. coli* colonies was observed under an optical microscope. Most of the plates used in this experiment exhibited mold contamination that looks very different from *E. coli* colonies. The mold growth was most likely observed as a result of the moisture trapped during the agar plate preparation. Due to contamination the results of this study were inconclusive.

The second in-vivo trial included same 5 subjects (18-50 years old) with healthy skin (3 men and 2 women). Test materials were:

1. Saline (negative control),
2. Purell® Advance Gel,
3. CGB-S-100, Lot #012-049. The fingers were randomized according to the Table 1.

The TSA plates utilized for this study were premade and obtained from a certified vendor to avoid issues observed in the first experiment.

1 mL of Test Articles or Control were applied on fingerpads to avoid any untreated area that could be exposed, and were gently rubbed onto the skin 10 μL of freshly prepared *E. coli* suspension in concentration of 8.08×107 CFU/ml was applied on each finger pad at predetermined time points. After inoculation, the bacterial suspension was allowed to dry for 60 s.

Each finger pad was pressed onto the agar plate and left at 37° C. for 24 hrs. All the inoculation and test applications were performed in Biological Safety Cabinets. Obtained bacterial growth results are presented in FIG. 1.

From FIG. 1, in subjects #2, #3 and #5 Purell® Advance Gel was unable to protect hands at 30 min of post application, where CGB-S-100 Gel was effective even after 2 and 4 hrs. In Subject #3 the bacterial growth was observed at 30 min of post application of CGB-S-100 Gel. However, no bacterial growth was obtained at 2 and 4 hrs of post application. The *E. coli* growth obtained at 30 min post application was most likely because the inoculum didn't completely dry when the finger was pressed onto the agar plate.

The first in-vivo trial was inconclusive as contamination (mold growth) was observed in the plates after 24-hour incubation. The mold growth was confirmed through an optical microscope. The second in-vivo trial clearly confirmed the persistence of antibacterial activity of CGB-S-100 gel in comparison to negative control and the comparator product (Purell® Advance Gel). The Purell® Advance Gel test group failed to protect the fingers from inoculum just after 30 min from application, while no growth was observed for CGB-S-100 gel treated fingers up to 4 hrs.

Example 2. Evaluation of Residual Antimicrobial Efficacy of Sanitizer a Containing 5% CAGE The purpose of this study is to test residual antimicrobial efficacy of 5% Sanitizer A and to compare it to the marketed product Purell®.

Materials

Bacterial Strain: *E. coli*
TSA petri dishes
Culture medium
Purell® advanced hand sanitizer, refreshing gel
0.9% sterile saline
5% Sanitizer A (LIN4 #012-040)

Methods

For the residual antibacterial activity study on the skin, the 5% Sanitizer A will be compared to the commercial brand Purell® hand sanitizer (active ingredient 70% EtOH).

As a negative control 0.9% saline solution will be used.

The antibacterial efficacy of test product (5% Sanitizer A) vs. comparator ethanol based hand sanitizer will be determined visually by the difference between the number of challenge bacteria species grown on Tryptic Soy Agar (TSA) following exposure to the test materials and the number grown from the untreated/saline treated (negative control) test sites on the skin.

The study will be performed on 5 subjects (18-50 years old) with healthy skin (3 male and 2 female).

The fingertips of each subject will be used for the test. Test sites will be determined through the finger creases for the test product, comparator products, and negative control.

The sites (fingers) will be randomized among the subjects to prevent anatomical bias.

The fingertips will be washed with nonmedicated soap to remove surface dirt and oil, air dried, and finally will be decontaminated with 70% isopropyl alcohol and allowed to air dry.

The challenge bacterial strain for this study will be *E. coli. E. coli* is a common skin contaminant and therefore provides an appropriate test organism. Fresh, active stocks were prepared in broth medium daily. The day before testing, a sample of the broth culture will be transferred to fresh broth medium.

Ten microliters of *E. coli* suspension will be applied to and spread over the fingertips at appropriate time intervals.

Procedure: Evaluation of Antibacterial Efficacy

Application of the test and comparator products: Each test sample will be applied to the fingertip skin.

In all the cases, the test articles and controls will be applied in stages (according to the Table 1), spread over the whole area, and allowed to dry for predetermined time points between each bacterial application.

Once all of the test applications are made, the subjects will be sequestered and monitored at the test facility to ensure test site integrity.

The persistent efficacy of the test samples will be evaluated at 0.5, 2, and 4 hours after application of the product to the skin. The negative control and comparator product will be evaluated at only 0.5 hour after application.

At each time point, 10 μL of the bacterial suspension will be applied to test areas in the test product treatment area and spread over the surface with a sterile glass rod.

The procedure will be repeated on the comparator product treatment area and on the negative control area.

Each inoculation will be allowed to dry in place for at least 15 mins but not for more than 25 minutes.

Figure 2:
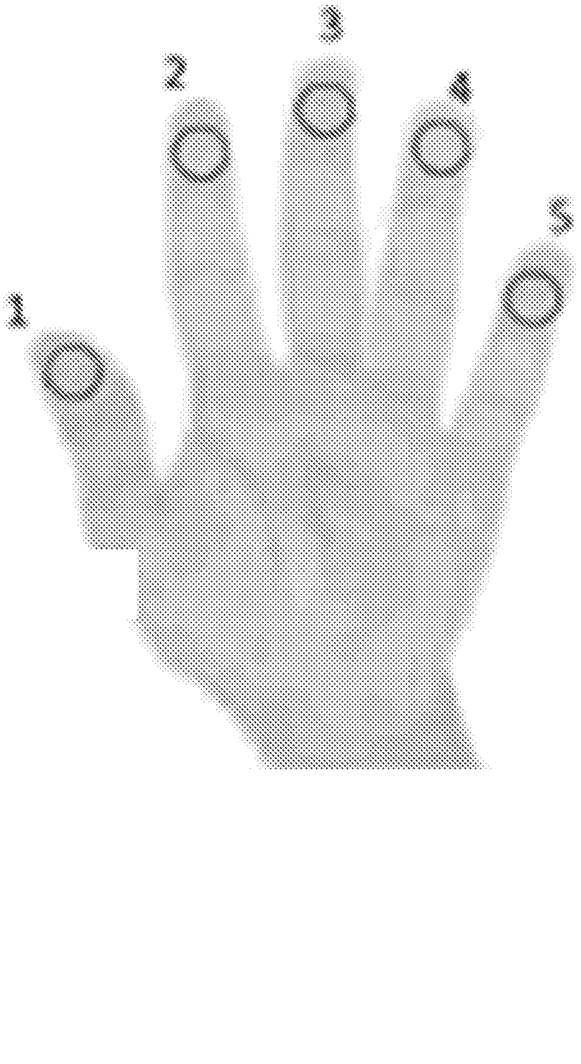
FIG. 2 shows the finger numbering for the studies described herein.
Figures 9A, 9B:
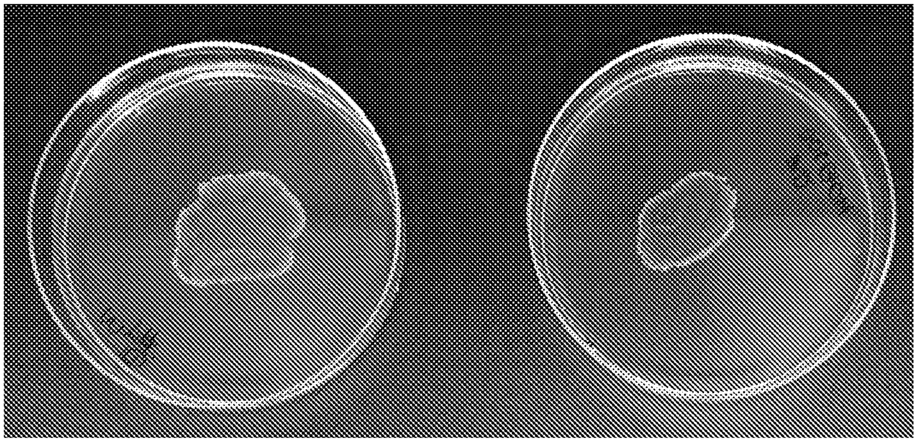
FIGS. 9A-9E show bacterial growth on TSA agar plates after fingers were inoculated negative control, 70% ethanol, and SANITIZER A (results for the study of Example 7).
Figures 9C, 9D, 9E:
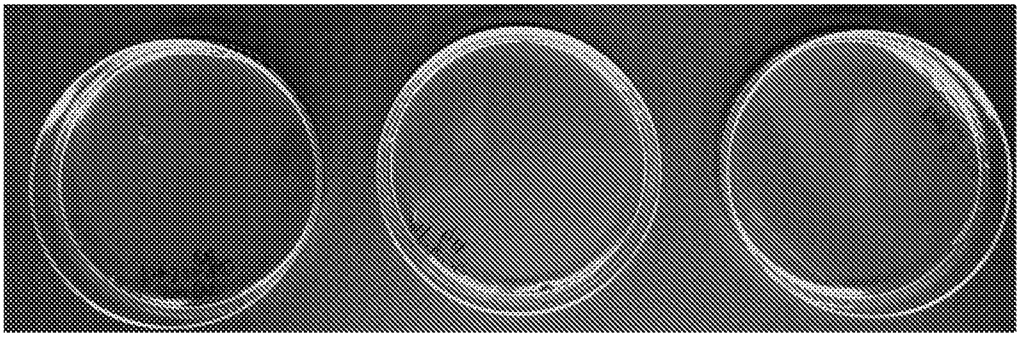
Figure 10:
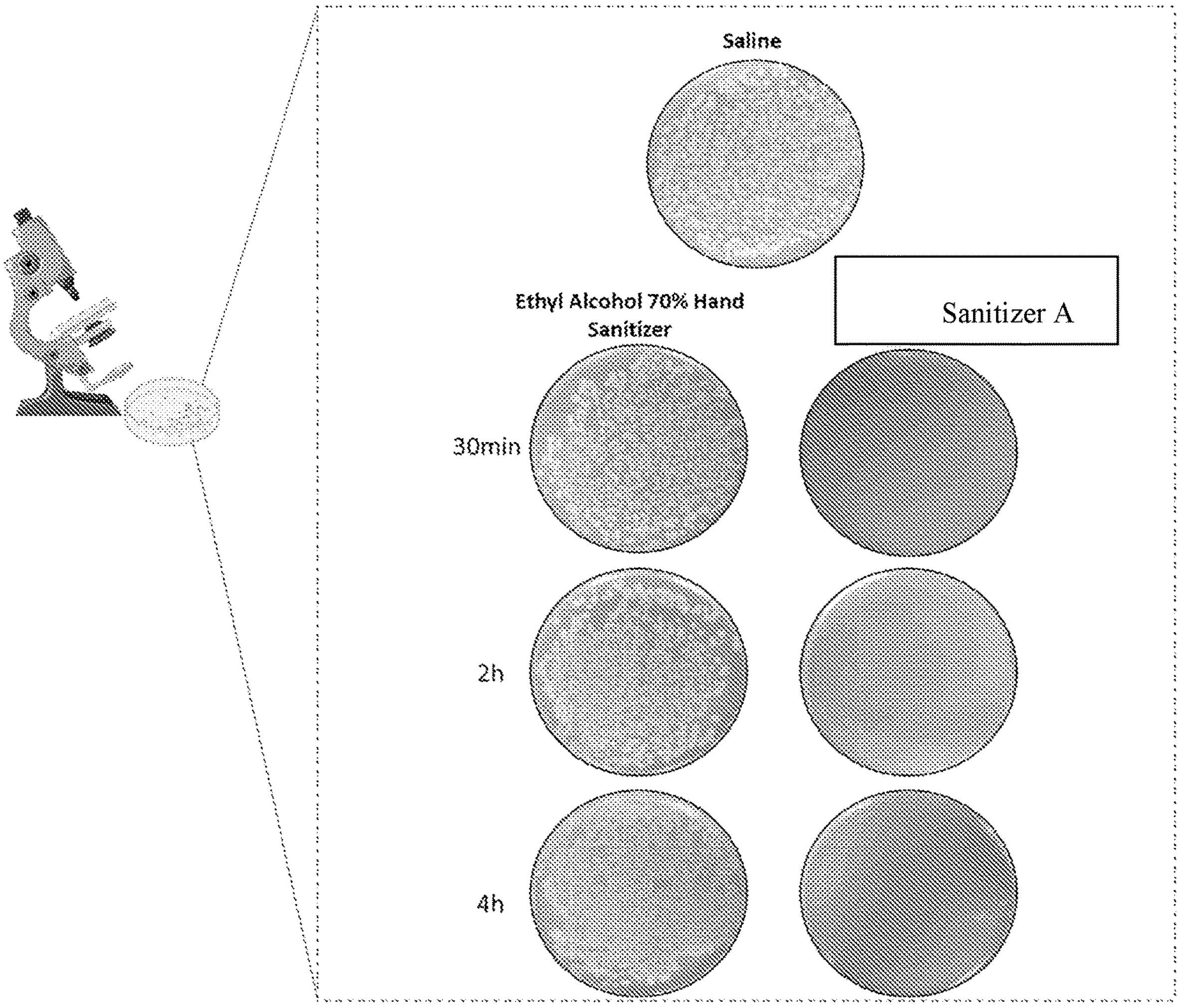
FIG. 10 shows the in-vitro antibacterial efficacy against *E. coli*. Number of viable test microorganisms treated with the test substances, ethyl alcohol 70% hand sanitizer (comparator) and Sanitizer A in comparison to the saline-treated group (negative control) The treated groups were incubated with the test substances for 30 min, 2 h and 4 h and subsequently exposed to *E Coli* for 5 min and then neutralized. Bacterial growth was assessed on agar plates after a 48-hour incubation period.
Figure 11A:
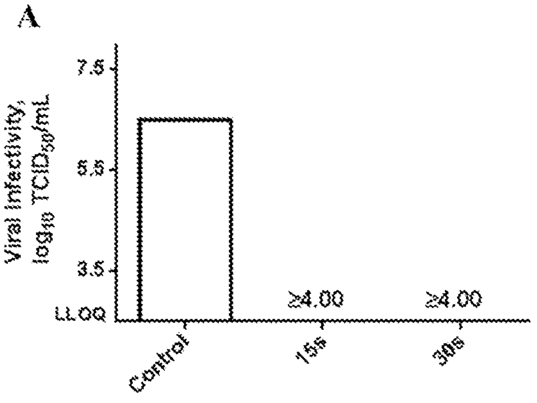
FIGS. 11A-11B show GLP virucidal efficacy test against human coronavirus strain 229E (hCoV229E). Virucidal infectivity to MRC-5 cells for (A) Sanitizer A and (B) CG-101 (5% w/w) treated viral suspensions in comparison to virus control (untreated) for different exposure times. $Log_{10}$ reduction are included above the bar. Viral titers are displayed as $TCID_{50}$/mL values (n=4). LLOQ, lower limit of quantification; $TCID_{50}$/mL, 50% tissue culture infectious dose.
Figure 11B:
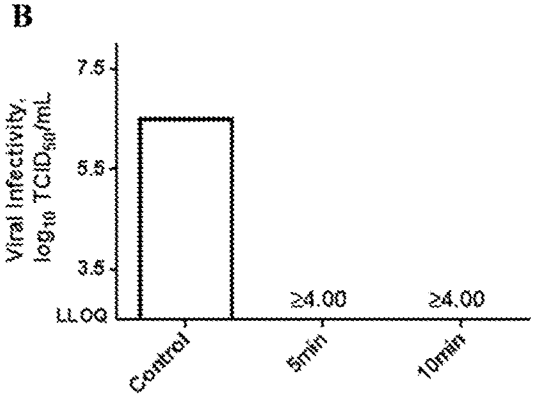
Figure 12A:
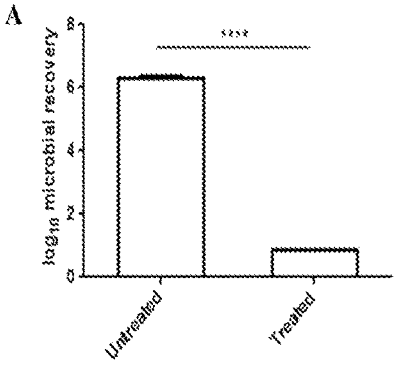
FIGS. 12A-12C show residual antimicrobial efficacy against *S. aureus*. The means of $log_{10}$ microbial recovery in comparison to untreated subjects (A) immediately (30 min), (B) 2 h, and (C) 4 h following application of the Test Product: Sanitizer A. Data are averages ±SEM, statistics by two-way ANOVA with Bonferroni's multiple comparison-test. ****$P<0.0001$ ($n=11$).
Figure 12B:
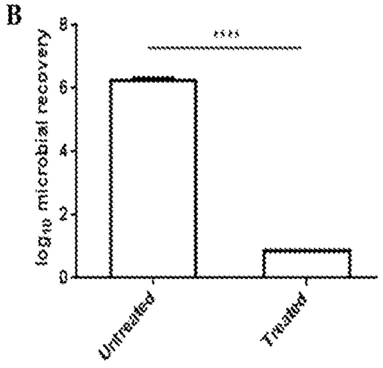
Figure 12C:
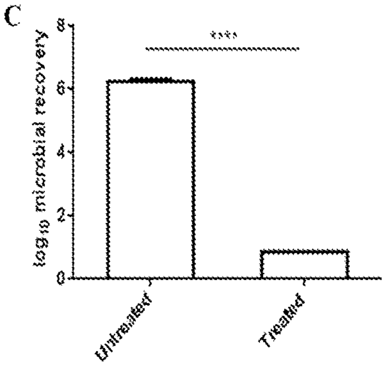

At the end of this exposure period, the fingertips will be tapped onto the TSA petri dishes and were incubated at 37° C. for 24 hours for bacterial growth (see Table 1 and FIG. 2). On TSA, *E. coli* produced golden yellow colonies, and only those colonies were considered.

TABLE 1

| Subjects | Subject # 1 | Subject # 2 | Subject # 3 | Subject # 4 | Subject # 5 |
|---|---|---|---|---|---|
| Negative Control (sterile saline) | Finger 1 | Finger 2 | Finger 3 | Finger 4 | Finger 5 |
| Positive Control (Purell ®) | Finger 2 | Finger 3 | Finger 4 | Finger 5 | Finger 1 |
| 5% Sanitizer A 0.5 hour | Finger 3 | Finger 4 | Finger 5 | Finger 1 | Finger 2 |
| 5% Sanitizer A 2 hours | Finger 4 | Finger 5 | Finger 1 | Finger 2 | Finger 3 |
| 5% Sanitizer A 4 hours | Finger 5 | Finger 1 | Finger 2 | Finger 3 | Finger 4 |

Example 3. Evaluation of the Virucidal Properties of Two Test Products Versus Coronavirus The purpose of this study is to evaluate the virucidal properties of two test products when challenged with human Coronavirus strain 229E (ATCC #VR-740). The testing will be based upon ASTM E1052-20, Standard Practice to Assess the Activity of Microbicides against Viruses in Suspension. All testing will be performed in accordance with Good Laboratory Practices, as specified in 21 CFR Part 58, with the exception that the characterization of the identity, strength, purity, composition, stability, and solubility of the test product(s) remains the responsibility of the Study Sponsor and will not be performed by the Testing Facility (GLP 58.105).

Scope

This study is designed to evaluate the virucidal properties of two test products versus Coronavirus strain 229E (ATCC #VR-740) using a Virucidal Suspension Test (In-Vitro Time-Kill method) based upon ASTM E1052-20. The percent and log 10 reductions from the initial population of the viral strain(s) will be determined following exposure to the test product, CGB-S-100 Gel, Hand Sanitizer, for 15 seconds and 30 seconds, and to the test product, CAGE Solution, for 5 minutes and 10 minutes. Testing will be performed in 1 replicate. Plating will be performed in four replicates.

Test Products

The test products to be evaluated will be provided to the Testing Facility by the Study Sponsor, complete with appropriate documentation. If the Test Product names and lot numbers are not documented below, they will be presented in the Final Report. Responsibility for the determination of the identity, strength, purity, composition, and stability of the test product(s), as well as the retention of the test product(s), rests with the Sponsor.

| | |
|---|---|
| Test Product #1: | CGB-S-100 Gel, Hand Sanitizer |
| Lot Number: | 20338-02-02 |
| Manufacture Date: | Jun. 4, 2020 |
| Expiration Date: | Not Provided |
| Test Product #2: | CAGE Solution (13.17% water) |
| Lot Number: | 20F16B |
| Manufacture Date: | Jun. 17, 2020 |
| Expiration Date: | Dec. 17, 2020 |

Challenge Viral Strains:

Coronavirus (alphacoronavirus) strain 229E (ATCC #VR-740)

Host Cells:

MRC-5 (ATCC #CCL-171; human lung fibroblast cells)

Equipment:

Ultralow Temperature Freezer, Temperature Range ≤−70° C.

$CO_2$ Incubator, Temperature Range 37° C.±2° C. with 5% to 7% $CO_2$ $CO_2$ Incubator, Temperature Range 35° C.±2° C. with 5% to 7% $CO_2$ Refrigerators, 2° C.-8° C.

Water Bath, 37° C. 2° C.

Incubator, Refrigerator, Freezer, and Water Bath Thermometers

Continuously Adjustable Pipettes, 100 μL-1000 μL Capacity

Continuously Adjustable Pipettes, 20 μL-200 μL Capacity

Portable Pipetter

Inverted Compound Microscope

Laminar Flow Biological Safety Cabinet

Calibrated Minute/Second Timers

Centrifuge

Supplies:

Sterile Disposable Pipettes

Sterile Polystyrene Test Tubes

Sterile Universal 1.0 and 0.2 mL Pipette Tips

Powder-free Gloves

Sterile Tissue Culture Treated Multi-well Plates

Viral suspension

Sterile 100 μL and 1000 μL Positive Displacement Tips

Sterile Flasks

Sterile 50 mL Centrifuge Tubes

Sterile Reservoirs

Waste Pan

Non-Sterile Waste Beaker for discarded tips, etc.

Media:

1× Eagle's Minimum Essential Medium (EMEM) or other appropriate medium

Growth Medium (GM): EMEM with 10% FBS and 1% Antibiotic and L-glutamine

Maintenance Medium (MM): EMEM with 2% FBS and 1% Antibiotic and L-glutamine

Trypsin

Antibiotics (e.g., Penicillin-Streptomycin-Amphotericin B)

Fetal Bovine Serum (FBS)

Appropriate Product Neutralizer (i.e. D/E Neutralizing Broth)

TEST PRODUCT PREPARATION:

Test Product #1 will be used as received. Test Product #2 will be diluted to achieve 5% of active ingredient per Sponsor instructions.

Host Cell Preparation:

MRC-5 cells, obtained from American Type Culture Collection (ATCC), will be maintained as monolayers in disposable cell culture labware in accordance with BSLI SOP L-2084, "Procedure for Subculturing of Cells." Prior to testing, host cell cultures will be seeded onto multi-well cell culture treated plates. Cell monolayers will be 80% to 90% confluent and less than 48 hours old before inoculation with the virus.

Test Virus Preparation:

Viruses propagated and stored per BSLI SOP L-2102, Procedure for Production of High-Titered Virus Stock, will be used for this study. On the day of use, aliquots of a stock virus suspensions will be removed from a −70° C. freezer and thawed.

Virucidal Suspension Test:

The Virucidal Suspension Test will include the parameters outlined in Table 2.

TABLE 2

| Parameter | Summary | Plating Replicates |
|---|---|---|
| Virucidal suspension test | Virus + Test Product → Exposure → Neutralization → Dilution → Plating | 4 per group |
| Virus Control | Virus + Diluent→ Exposure → Dilution → Plating | 4 per group |
| Cytotoxicity Control | Test Product + Diluent → Neutralization → Dilution Plating | 4 per group |
| Neutralization Control | Test Product + Diluent → Neutralization → Virus inoculation → Dilution → Plating | 4 per group |
| Neutralizer Toxicity Control | Virus + Diluent → Neutralization → Dilution → Plating | 4 per group |
| Cell Culture Control | Maintenance medium | 4 per group |

Test. A 0.5 mL aliquot of test virus(s) will be added to a vial containing 4.5 mL of the test product(s). The test virus(s) will be exposed to the Test Product 41 for 15 seconds and 30 seconds and to the Test Product 42 for 5 minutes and 10 minutes, timed using a calibrated minute/second timer. The calibrated minute/second timer will be started within ±1 second of adding the challenge suspension. Immediately after exposure(s), the test virus(s)/product suspensions will be neutralized in appropriate neutralizer, mixed thoroughly, and serially diluted in MM. Each dilution will be plated in four replicates.

Virus Control. A 0.5 mL aliquot of test virus(s) will be added to 4.5 mL of MM and exposed for 10 minutes at ambient temperature. The subsequent test virus dilution will be made in MM. Each dilution will be plated in four replicates.

Cytotoxicity Control. A 0.5 mL aliquot of MM will be added to a vial containing 4.5 mL of the test product(s). The MM/product mixture will be neutralized in appropriate neutralizer, mixed thoroughly and serially diluted in MM. Each dilution will be plated in four replicates.

Neutralization Control. A 0.5 mL aliquot of MM will be added to a vial containing 4.5 mL of the test product(s). The MM/product mixture will be diluted 1:10 in appropriate neutralizer. An aliquot of the virus(s) will be added to the neutralized product(s) and thoroughly mixed and exposed to the neutralized product for 10 to 20 minutes. Subsequent 10-fold dilutions of neutralized test product/virus suspension will be made in MM. Each dilution will be plated in four replicates.

Neutralizer Toxicity Control. The effect of the neutralizer on virus infectivity will be assessed by adding virus to the neutralizer alone followed by exposure for 10 to 20 minutes. Subsequent 10-fold dilutions of neutralizer/virus suspension will be made in MM. Each dilution will be plated in four replicates.

Cell Culture Control. Intact cell culture will serve as the control of cell culture viability. The GM will be replaced by MM in all cell control wells.

The plates will be incubated in a $CO_2$ incubator for 10 to 14 days at 35° C.±2° C.

Cytopathic/cytotoxic effect will be monitored using an Inverted Compound Microscope.

Note: In cases when viral CPE is undetectable using Inverted Compound Microscope, additional immunostaining with virus specific antibodies can be performed.

Calculations:

Viral and toxicity titers will be expressed as $-\log_{10}$ of the 50% titration end point for infectivity. To calculate the viral titer, a 50% tissue culture infectious dose ($TCID_{50}$) calculation—the Quantal test (Spearman-Karber Method)—will be applied.

$$\text{Log } TCID_{50}=L-d(s-0.5)$$

where:

L=$-\log_{10}$ of the lowest dilution;

d=difference between dilution steps;

s=sum of proportions of positive wells.

The $\log_{10}$ of infectivity reduction will be calculated as follows:

$\text{Log}_{10}$ Reduction Formula:

$$\text{Log}_{10}\text{ Reduction}=(\log_{10} TCID_{50}\text{ of the Virus Control})-(\log_{10} TCID_{50}\text{ of the Virucidal Suspension Test})$$

The percent reduction will be calculated as follows:

$$\%\text{ Reduction}=\left[1-\frac{TCID_{50}\text{ test}}{TCID_{50}\text{ virus control}}\right]\times 100$$

Statistical Analysis:

The Quantal test (Spearman-Karber Method) will be applied to calculate virus titer. No control of bias will be performed.

Test Acceptance Criteria:

A valid test requires that: 1) at least 4 log 10 of TCID50 be recovered from the Virus Control; 2) cells in the cell culture wells be viable and attached to the bottom of the well; 3) the medium be free of contamination in all wells of the plate; 4) when cytotoxicity is evident, at least a 3 log 10 reduction in titer be demonstrated beyond the cytotoxic level, and 5) the test product be fully neutralized after the timed exposure such that the difference in virus titer for the Neutralization Control and Virus Control does not exceed 1.0 $\log_{10}$.

Example 4. Preliminary In Vivo Trial with One Subject

1) Hands were washed with a non-medicated soap and 70% isopropyl alcohol (IPA) and allowed to dry
2) Test material and controls were applied on the upper part of a finger and allowed to dry
3) Fingers #1-3 (see FIG. 2) were inoculated with 10 µL of concentrated suspension of *E. coli* at 30 min of post application. Inoculum was spread uniformly over a fingertip area
4) After 60 sec of contact time each finger from #1 to 3 was tapped on the TSA agar plate. Plates were transferred into the incubator set at 37 C
5) Finger #4 was inoculated with 10 µL of concentrated suspension of *E. coli* at 1 hr of post application
6) After 60 sec of contact time finger #4 was tapped on the TSA agar plate. Plate was transferred into the incubator set at 37 C
7) Finger #5 was inoculated with 10 µL of concentrated suspension of *E. coli* at 2 hrs. of post application.

After 60 sec of contact time finger #5 was tapped on the TSA agar plate. Plate was transferred into the incubator set at 37° C.

The growth was examined after −24 hrs of incubation

No bacterial growth was observed for Sanitizer A (see FIGS. 3A-3E).

Example 5. In Vivo Trial with Five Subjects

Experimental Details:

Hands were washed with a non-medicated soap and then with 70% IPA and allowed to dry Purell® Advance was used as a positive control and 0.9% saline solution as a negative control Subject's fingers were randomized to prevent anatomical bias 1 ml of Test Article or Control was applied on each finger and was gentle rubbed into the skin 10 µL of fresh *E. coli* suspension at concentration of $8.08\times10^7$ CFU/mL was applied on each finger at certain time and allowed to dry for −60 sec.

Each finger was pressed onto the plate with agar media

Plates were transferred into the incubator set at 37° C.

The growth was examined after 24 hrs of incubation

No bacterial growth was observed for any of the five subjects after inoculation with a high-concentrated suspension of *E. coli* at 2 and 4 hrs of post application of hand sanitizer. Thus, Sanitizer A protects hands during at least 4 hrs. In contrast, four out of five Purell® Advance did not demonstrate protection after 30 min (see FIGS. 4A-4E, FIGS. 5A-5E, FIGS. 6A-6E, FIGS. 7A-7E, and FIGS. 8A-8E).

Example 6. Sanitizer A

Formulation
1. 1-10% choline geranate (CAGE, or CG-101)
2. 70% Alcohol (60-90%)
3. 0.3-1.0% D-Limonene as a fragrance
4. 0.3-1.0% of hydroxypropyl cellulose as a gelling agent
5. Glycerin 1-2% as a humectant
6. Aloe vera
7. Emollients

TABLE 3

Composition of Sanitizer A

| Ingredient | Composition, wt. % |
|---|---|
| CG-101 (choline:geranate = 1:2) | 5.00 |
| Ethanol 99.9% | 70.0 |
| Glycerin | 1.45 |
| D-Limonene | 0.80 |
| Hydroxypropyl cellulose | 0.80 |
| DI Water | q.s. to 100 |

Example 7. In Vivo Study for Determination of Residual Antimicrobial Efficacy of Sanitizer A Experimental Design:
1) Wash hands with nonmedicated soap to remove surface dirt and oil, dried, and finally decontaminate with 70% isopropyl alcohol. Allow to air dry.
2) Apply test article (Sanitizer A containing 5% CAGE) and controls (70% Alcohol and DI Water or 0.9% Sterile Saline Solution) on each finger tap to cover it completely. Let it dry.
3) Inoculate the finger taps #1-3 with 10 μL of high-concentrated suspension of *E. coli* at 30 min of post-application.
4) Wait for 60 sec (contact time)
5) Tap the finger on the TSA agar plate and transfer plates #1-3 into the incubator set at 37° C.
6) Apply 10 μL of inoculum on Finger #4 at 1 hr. of post application.
7) Wait for 60 sec and tap the finger on the TSA agar plate. Transfer plate into the incubator set at 37° C.
8) Apply 10 μL of inoculum on Finger #5 at 2 hrs of post application.
9) Wait for 60 sec and tap the finger on the TSA agar plate. Transfer plate into the incubator set at 37° C.
10) Observe bacterial growth after 24 hrs in incubator.

Results

Microbial growth was observed after 24 hrs at 37 C for Negative (DI Water) and Positive (70% Ethanol) controls treatments:

Microbial growth was examined after 24 hrs at 37° C. for Negative (DI Water) and Positive (70% Ethanol) controls treatments (see FIGS. 9A-9E).

No microbial growth was observed after 24 hrs at 37° C. for samples that were treated with 5% Sanitizer A (i.e. Sanitizer A containing 5% CAGE).

Example 8. Hand Sanitizer with Alcohol and Non-Volatile Polymer Component

Formulation Components:
1. 1-10% polymer
2. 70% Alcohol (60-90%)
3. 0.3-1.0% D-Limonene as a fragrance
4. 0.3-1.0% of hydroxypropyl cellulose as a gelling agent
5. 1-2% as a humectant
6. Aloe vera
7. Emollients

TABLE 4

Composition of Polymer-Based Hand Sanitizer

| Ingredient | Composition, wt. % |
|---|---|
| Polymer | 5.00 |
| Ethanol 99.9% | 70.0 |
| Glycerin | 1.45 |
| D-Limonene | 0.80 |
| Hydroxypropyl cellulose | 0.80 |
| DI Water | q.s. to 100 |

In certain embodiments, the polymer is a peptide-mimetic antimicrobial polymer. In certain embodiments, the polymer is a poly(styrene), poly(vinylpyridine), poly(vinyl alcohol), polymethacrylate. In certain embodiments, the polymer is a nylon, nylon-type synthetic polymer, polycarbonate, polynorbornene, vinyl polymer, co-polymer, a cationic polymer, polyurethane, guanide or biguanide polymer.

Example 9. Hand Sanitizer with Alcohol and Non-Volatile Dendrimer Component

Formulation Components:
1. 1-10% dendrimer
2. 70% Alcohol (60-90%)
3. 0.3-1.0% D-Limonene as a fragrance
4. 0.3-1.0% of hydroxypropyl cellulose as a gelling agent
5. 1-2% as a humectant
6. Aloe vera
7. Emollients

TABLE 5

Composition of Polymer-Based Hand Sanitizer

| Ingredient | Composition, wt. % |
|---|---|
| Dendrimer | 5.00 |
| Ethanol 99.9% | 70.0 |
| Glycerin | 1.45 |
| D-Limonene | 0.80 |
| Hydroxypropyl cellulose | 0.80 |
| DI Water | q.s. to 100 |

In certain embodiments, the dendrimer is N-(3-aminopropyl)methacrylamide hydrochloride (APMA), poly(N-(3-aminopropyl)methacrylamide) (PAPMA), poly(amidoamine)-dendrimer (PAMAM-dendrimer), or poly(propylene imine)-dendrimer (PPI-dendrimer).

Example 10. Hand Sanitizer with Alcohol and Non-Volatile Antimicrobial Peptide (AMP) Component Formulation Components:

8. 1-10% antimicrobial peptide (AMP)
9. 70% Alcohol (60-90%)
10. 0.3-1.0% D-Limonene as a fragrance
11. 0.3-1.0% of hydroxypropyl cellulose as a gelling agent
12. 1-2% as a humectant
13. Aloe vera
14. Emollients

TABLE 6

Composition of AMP-Based Hand Sanitizer

| Ingredient | Composition, wt. % |
| --- | --- |
| AMP | 5.00 |
| Ethanol 99.9% | 70.0 |
| Glycerin | 1.45 |
| D-Limonene | 0.80 |
| Hydroxypropyl cellulose | 0.80 |
| DI Water | q.s. to 100 |

Example 11. Safety and Efficacy of Sanitizer A

Safety of CG-101 in human volunteers. Safety of CG-101 (100% concentration) was tested in a 3-week human repeat insult patch test (HRIPT) in 52 adult human volunteers. The concentration of CG-101 was 20 times higher than that used in Sanitizer A. CG-101 was applied to the back of the subjects over a marked 2×2 $cm^2$ area and covered with an occlusive hypoallergenic patch to maximize penetration. Distilled water was used as a negative control. The patches were removed by the subjects after 24 h and a new one was applied by the site staff at the same exact site at the next visit. The subjects reported to the site for a total of 9 visits, 3 each week. During each visit the application area was observed by the study investigator and a new patch was applied. None of the subjects showed any skin reactions in the first 3 visits (7-days). 43 subjects did not display any irritation throughout the entire 21-day study. Between visits 4 through 9, 8 subjects experienced some skin irritation. However, there was no follow-up treatment required for any of these 8 subjects that showed irritation. There were no other adverse events reported in the study. Furthermore, upon completion of the 21-day study period, and a rest period of two weeks, CG-101 application with occlusion to a different part of the body, did not create any sensitization response at 24 and 48 h.

Superior antibacterial efficacy of Sanitizer A. In order to determine the prolonged protective effects of Sanitizer A in contrast to the currently embodiment containing 70% ethyl alcohol, an in-vitro efficacy study was conducted using *E. coli* following modified ASTM E1153 methodologies. One milliliter of the test and comparator products were applied onto the pre-cleaned glass surfaces and dried for 30 min. Glass slides were inoculated with 10 μl of bacterial suspension at various timepoints (30 min, 2 h, and 4 h). The test compound was chemically neutralized after an exposure duration of 5 min before transferring the samples to agar plates. The agar plates were visually compared for microbial growth after incubation for 48 h at 37° C. No *E. coli* growth was observed for the Sanitizer A-treated groups for 30 min, 2 h as well as 4 h which clearly indicated the persistent antimicrobial activity of Sanitizer A. In contrast, almost similar *E. coli* growth was observed for the saline-treated group and the comparator, ethyl alcohol 70% hand sanitizer treated group (FIG. 1). This indicates that alcohol-based products might have limited ability to provide long lasting protective effects against microbes. On the contrary, Sanitizer A provided clear indication of long-lasting protection against pathogens and thus potentially reducing disease transmission during a pandemic.

Protection against hCoV229E. Based on the previously demonstrated broad-spectrum antimicrobial properties of CG-101[23], we anticipated that CG-101 and the skin protectant containing CG-101 (Sanitizer A) would effectively deactivate coronavirus likely through disruption of the phospholipid bilayer glycoproteinaceous envelope. We evaluated the virucidal effects of the skin protectant, Sanitizer A and the active CG-101 (5% w/w in purified water) against human Coronavirus strain 229E (hCoV229E) using a virucidal suspension test (in-vitro time-kill method) based on industry/regulatory-relevant global standardized methodologies (ASTM E1052-20). The $\log_{10}$ reductions from the initial population of the hCoV229E following 15 s and 30 s exposure to Sanitizer A was found to be >4.00. In fact, the percent reduction for both the time points was >99.99. Similarly, we evaluated the virucidal activity of CG-101 (5% w/w) using the quantitative suspension test for exposure times, 5 min and 10 min. The percent and $\log_{10}$ reductions from the initial population of the hCoV229E following 5 min and 10 min exposure to CG-101 (5% w/w) was found to be >99.99 and >4.00 respectively (FIG. 2 and Tables Si and 2).

Prolonged residual antimicrobial efficacy of Sanitizer A in humans. Clinical studies approved by an IRB were performed at Bioscience laboratories, Inc. (testing facility) in compliance with good clinical practice regulations to test the effectiveness of Sanitizer A to provide extended protection against microbes. Specifically, Sanitizer A was applied to the forearms of human volunteers and the randomly assigned test sites on each forearm were challenged by application of *Staphylococcus aureus* (*S. aureus*) at various times after the application of Sanitizer A. The residual antimicrobial efficacy of Sanitizer A was tested using a modification of the standardized test method described in ASTM E2752-10 (2015) in 12 healthy subjects. A significant (>5.15) $\log_{10}$ reduction in *S. aureus* from the control was observed following 30 min., 2 h and 4 h post-Sanitizer A application.

Immediately following application and 30-min air-dry of the Sanitizer A, the mean $\log_{10}$ microbial recovery for the treated subjects was found to be 0.86±0.00 in contrast to 6.30±0.05 for the untreated subjects. Furthermore, the $\log_{10}$ microbial recovery, 2 h following application of the Sanitizer A, was found to be 0.86±0.00 for the treated subjects vs 6.24±0.07 for untreated subjects. Interestingly, post 4 h application of Sanitizer A, the $\log_{10}$ microbial recovery for treated subjects was also 0.86±0.00 in comparison to 6.24±0.12 for untreated subjects. Note that the lowest detectable limit of the study was 0.86 $\log_{10}$ CFU/$cm^2$. Sanitizer A thus demonstrated prolonged microbial protection for up to 4 h after a single application (FIG. 3 and Table S3). These data and the lack of any trend from 0.5 h, 2 h and 4 h suggest that the effectiveness of IonLAST could persist beyond 4 h.

Current evidence suggests that SARS-CoV-2 predominantly spreads through person-to-person via saliva and respiratory secretions or droplets[26]. Other modes of transmission could be contaminated objects or surfaces (fomite transmission), fecal-oral, bloodborne, mother-to-child, and animal-to-human transmission[27]. The relative roles of various routes are unclear and will require additional epidemiological data as well as mechanistic information about the virus entry. For example, angiotensin-converting enzyme 2 (ACE2), the cell receptor for SARS-CoV-2 entry is abundantly present in blood vessels/capillaries of the skin, the basal layer of the epidermis, and hair follicles[28, 29].

Hand hygiene is widely recognized for playing a major role in limiting the spread and transmission of such infectious diseases[18]. In fact, in order to cope with such a pandemic situation, CDC has specifically recommended washing of hands with soap and water whenever possible. However, it has been reported that frequent washing hands with water and soap may damage skin potentially leading to dermatitis[30]. While alcohol-based hand sanitizers with at least 60% alcohol can help in avoiding sickness and spreading germs to others, unfortunately the protective effect of alcohol lasts only till the alcohol evaporates i.e. less than a couple of minutes. Frequent handwashing is also burdensome and disruptive in many situations, and in some cases just not practical[31].

Inspired by the fact, that CG-101 exhibits broad-spectrum antimicrobial properties against a range of bacteria, virus, and fungi, we developed an alcohol-based skin protectant containing CG-101 as a countermeasure to restrict the rampant spread of the COVID-19 infection. CG-101 inactivates pathogens by extracting lipids and disrupting the cell membrane[21]. More importantly, unlike ethanol, which is highly volatile, CG-101, being an ionic liquid/deep eutectic solvent, has a very low vapor pressure and can remain on the skin long after ethanol evaporates. This long-lasting residence of CG-101 is expected to be responsible for long-lasting protection against SARS-CoV-2 thus limiting the need for frequent hand washing.

Human volunteer studies confirmed the safety of the active, CG-101(~100% concentration). HRIPT, an industry standard test for evaluating the potential of a test material to induce sensitization in humans after repeated exposure was adopted[32]. Among 52 adult human volunteers who were treated with 20× higher CG-101 than that used in the Sanitizer A, 43 subjects did not display any irritation throughout the entire 21-day study. There were no other adverse events reported in the study. Furthermore, following completion of the study and a rest period of two weeks, CG-101 application to a different part of the body, did not create any sensitization response at 24 and 48 h which indicates the potential of CG-101 as a safe additive for topical products.

In-vitro bactericidal assay was conducted to compare the longevity of antibacterial efficacy of Sanitizer A in contrast to currently marketed alcohol-based products against *E. coli*. The visual difference in the number of viable test microorganisms for the alcohol-based product and Sanitizer A was striking for all the time points including 30 min, 2 h and 4 h. No notable difference in the microbial growth was observed between the untreated and alcohol-based hand sanitizer treated groups (FIG. 1) indicating the short duration of protection rendered by ethanol. This signifies the persistence of protective effects of Sanitizer A against *E. coli* and possibly other pathogens for up to 4 h.

The encouraging results obtained from the bactericidal efficacy studies, motivated us to test Sanitizer A against hCoV229E. As theorized, CG-101 was able to deactivate the virus, generating excellent virucidal efficacy against hCoV229E. Sanitizer A generated >4.00 $\log_{10}$ reductions in viral titers following 15 s and 30 s exposure. Moreover, virucidal activity of the active, CG-101 (5% w/w) for exposure times, 5 min and 10 min generated similar $\log_{10}$ reductions (>4.00) from the initial population of the hCoV229E as Sanitizer A (FIG. 2) indicating hCoV229E is highly susceptible to Sanitizer A.

Residual antimicrobial efficacy study was undertaken to measure the relative persistence of antibacterial activity under controlled clinical test conditions. The results demonstrated a significant (>5.15) $\log_{10}$ reduction in *S. aureus* following immediate, 2 h and 4 h post-Sanitizer A application (FIG. 3). These results further support persistent pathogen inactivation efficacy of Sanitizer A. Upon further clinical studies demonstrating the prolonged protection rendered against hCoV229E, Sanitizer A may open new opportunities in the recommended hand hygiene protocols for preventing disease transmission. With its long-lasting effect, IonLAST offers a promising complement to the existing CDC/WHO guidelines for good hand hygiene.

Materials and Methods

Clinical safety study of CG-101. For the HRIPT, skin irritation and sensitization potential of CG-101 was evaluated in a 21-day human repeat insult patch test in 52 volunteers. This cosmetic study was approved by an IRB and conducted by AMA Laboratories Inc. in New York. CG-101 (100%, liquid) was applied on the back of volunteers over a 2×2 $cm^2$ area on each of 9 visits over a period of 3 weeks. The application area was occluded with hypoallergenic tape. The subjects were required to keep the tape for 24 h. At each visit, the application site was evaluated for skin irritation on a 5-point scale (0-4). Any subjects that showed irritation rated at 3 or higher were withdrawn from the study and monitored for changes. After completion of the 3-week test period the subjects were given a 10 to 14-day rest, after which CG-101 solution was applied to a previously unexposed site. The subjects were then evaluated for any skin reactions after 24 and 48 h.

In-vitro bactericidal efficacy. In order to determine the relative bactericidal efficacy of Sanitizer A in contrast to an alcohol-based product, ASTM E1153, standard test method for efficacy of sanitizers recommended for inanimate non-food contact surfaces was modified and employed accordingly. Briefly, pre-cleaned surfaces were transferred into sterile petri plates using sterile forceps and covered with 1 ml of the test substances and held for 30 min at ambient temperature to dry. The inoculation with 10 μl of *E. coli* suspension was performed at 30 min, 2 h and at 4 h. After each inoculation, the exposure time was 5 min. After 5 min, the test compound was neutralized, and the viable bacteria were resuspended. A neutralization study was conducted to assure that the neutralizers used for the study quench the antimicrobial activity of each test material and were not toxic to the challenge species. After neutralization, the samples were plated on agar plates and transferred into the incubator set at 37° C. for 48 h. An average of at least >104 CFU of bacteria were recovered from the negative and neutralization controls. The number of viable organisms on the agar plates treated with Sanitizer A were then compared visually to a negative control (untreated) and the comparator (ethyl alcohol 70% hand sanitizer) following 48 h incubation.

Virucidal suspension test. The virucidal test was based upon ASTM E1052-20, standard practice to assess the activity of microbicides against viruses in suspension. All testing was performed in accordance with Good Laboratory Practices (GLP), as specified in 21 CFR Part 58 at BioScience Laboratories, Inc. (BSL), Bozeman, Montana. The characterization of the identity, strength, purity, composition, stability, and solubility of the test product(s) was performed by CAGE Bio Inc. The percent and $log_{10}$ reductions from the initial population of the viral strain(s) was determined following exposure to the test product, Sanitizer A, for 15 s and 30 s, and to the test product, CG-101 (5% w/w), for 5 min and 10 min. Testing was performed in 1 replicate. Plating was performed in four replicates. Coronavirus (alphacoronavirus) strain 229E (ATCC #VR-740) and MRC-5 (ATCC #CCL-171; human lung fibroblast cells) were used for the study.

Residual antimicrobial efficacy test. The residual antimicrobial efficacy testing was carried out using a modification of the standardized test method described in ASTM E2752-10 (2015), standard guide for evaluation of residual effectiveness of antibacterial personal cleansing products. The study was conducted in compliance with Good Clinical Practice Regulations, Good Laboratory Practice Regulations, the standard operating procedures of BioScience Laboratories, Inc., the study protocol, and any protocol amendments. Bacterial recoveries were assayed after application of test material, using the forearms as a substrate. At least twelve test subjects (aged 18-65 years), with healthy skin were used in this study, and the test product was applied on one arm, and had the other arm untreated as the negative control. The test sites on both forearms were inoculated with suspensions containing *S. aureus* (ATCC #6538), immediately after the 30-minute product drying time, and at approximately 2 h and 4 h following test material applications. The test sites were sampled using the cup scrub procedure approximately 20 min following each inoculation. The log 10 microbial recoveries of treated versus untreated sites were the basis for assessing the residual antimicrobial effectiveness of the test product.

A neutralization study was also performed to assure that the neutralizers used in the recovery medium quench the antimicrobial activity of each test material and were not toxic to the challenge species. Study procedures were based on ASTM E 1054-08(2013), standard test methods for evaluation of inactivators of antimicrobial agents. *S. aureus* (ATCC #6538) was used as the challenge species in the neutralization study.

Statistical Analysis. For the virucidal suspension test, the Quantal test (Spearman-Karber Method) was applied to calculate virus titer. No control of bias was performed. The MiniTab® Version 18 statistical computer package was used for all statistical calculations for the antimicrobial efficacy test. A blocked, one-factor Analysis of Variance (ANOVA) model was used:

$$y = \text{Blocks} + \text{Sample Time} + e$$

where:

$y$=$Log_{10}$ Reduction=Untreated $Log_{10}$ Recovery −Treated $Log_{10}$ Recovery Blocks=One subject will use both configurations.

Sample Time
1, if immediate
2, if 2 h
3, if 4 h
e=Error Term

Supplementary Materials

Materials and Methods

Virucidal suspension test. MRC-5 cells were maintained as monolayers in disposable cell culture labware in accordance with protocol. Prior to testing, host cell cultures were seeded onto multi-well cell culture treated plates. Cell monolayers reached 80% to 90% confluency and were less than 48 h old before inoculation with the virus. Briefly, the virucidal suspension test for the test products was performed by taking a 0.5 mL aliquot of test virus(s). It was added to a vial containing 4.5 mL of the test product(s). The test virus(s) was exposed to the Sanitizer A for 15 s and 30 s and to the CG-101 (5% w/w) for 5 min and 10 min, timed using a calibrated minute/second timer. The calibrated minute/second timer was started within is of adding the challenge suspension. Immediately after exposure(s), the test virus(s)/product suspensions were neutralized in appropriate neutralizer, mixed thoroughly, and serially diluted in maintenance medium (MM). Each dilution was plated in four replicates. All other controls were prepared following the standard protocol. Viral and toxicity titers will be expressed as $-log_{10}$ of the 50% titration end point for infectivity. To calculate the viral titer, a 50% tissue culture infectious dose ($TCID_{50}$) calculation—the Quantal test (Spearman-Karber Method)—was applied.

$$\text{Log } TCID_{50} = L - d(s - 0.5)$$

Where:
L=$-log_{10}$ of the lowest dilution;
d=difference between dilution steps;
s=sum of proportions of positive wells.

The $log_{10}$ of infectivity reduction was calculated as follows:

$Log_{10}$ Reduction Formula:

$Log_{10}$ Reduction=($log_{10}$ $TCID_{50}$ of the Virus Control)−($log_{10}$ $TCID_{50}$ of the Virucidal Suspension Test)

The percent reduction was calculated as follows:

$$\% \text{ Reduction} = \left(1 - \frac{TCID50test}{TCID50 \text{ virus control}}\right) \times 100$$

Residual antimicrobial efficacy test period. Each subject had one forearm assigned to use the test product and the other forearm remained as an Untreated Control. The sites on each forearm was randomized to the sample times, 30 min, 2 h and 4 h post product application. Subjects performed a 30 s wash with 5 mL of nonmedicated soap and a 30 s rinse to remove any dirt or oil from the forearms prior to the test. Subjects dried their hands and forearms with disposable paper towels. The temperature of the water was controlled at 40° C.±2° C. The forearms were decontaminated with 10 mL of 70% Ethyl alcohol (EtOH) dispensed over the surface of both forearms and allowed to air-dry. After completion of the forearm disinfection each subject will wait at least 5 min prior to continuing to the next step. The subjects were instructed to not touch anything with their forearms during this time. Using a surgical skin marker, 2"×6" test sites were marked out on the volar surface of each forearm. Three areas approximately 2 cm in diameter on the skin of the volar surface of each forearm were marked. The application test sites were re-marked as needed.

Test product application. A single 3-mL aliquot of test product was dispensed onto the subjects' forearm. A technician wearing sterile gloves evenly applied the test product over the entire 2"×6" test site. The inoculation process began 30 min 3 min after the test product was applied to the test site.

Inoculum application. Inoculum was prepared by following the study protocol. At three-time points following the 30-minute air-dry after test product application, a 10 μL (0.01 mL) aliquot of the challenge inoculum was applied to the randomly assigned test sites on each forearm, and a heat-polished glass rod was used to distribute the inoculum over the demarcated −2 cm diameter test area (but not reaching the edges of the demarcated area) and allowed to air-dry for at least 20 min. Inoculations began immediately after the 30 min 3 min drying time wait, 2 h±15 min, and 4 h±15 min after the completion of the test product application. The contaminated sites on each forearm were sampled using the Cup Scrub Technique following the 20 min inoculum air dry.

Cup scrub technique. A sterile stainless-steel cylinder with an inside area of 3.46 cm2 was held firmly onto a site to be sampled. A 1.0 mL aliquot of Sterile Stripping Suspending Fluid with product neutralizers (SSF++) was dispensed into the cylinder, and the skin area inside the cylinder was massaged in a circumferential manner for 1 min 10 s with a heat-polished glass rod. The 1.0 mL of SSF++ was removed with a pipette and transferred to a sterile test tube. A second 1.0 mL aliquot of SSF++ was dispensed into the cylinder, and the skin area massaged for 30 s±5 s with a heat-polished glass rod. The second 1.0 mL aliquot was then pooled in the test tube with the first aliquot. Gauze soaked in 70% Ethyl alcohol (EtOH) was used to decontaminate the sites.

Plating and data collection. Aliquots of the microorganism suspension (100 dilution) was serially diluted in Butterfield's Phosphate Buffer Solution with product neutralizers (BBP++), as appropriate. Duplicate spread plates were prepared from appropriate dilutions using Mannitol Salt Agar (MSA) and incubated at 35° C.±2° C. for approximately 48 h or until sufficient growth is observed. *S. aureus* (ATCC #6538) produced golden-yellow colonies on MSA, and only those colonies were counted. If colonies on one of the plates were uncountable, the count from the remaining plate was used. Average colony counts of 0 at the −1 dilution was recorded as <5.00 CFU/mL.

Supplementary Tables

TABLE S1

$Log_{10}$ reduction and percent reduction from control of hCoV229E (ATCC #VR-740) following 15- and 30 s by the test product: Sanitizer A

| Dilution ($-Log_{10}$) | Virus Control | Test: 15 seconds | Test: 30 seconds | NTC | NC | CTC | CC |
|---|---|---|---|---|---|---|---|
| −2 | NT | CT | CT | NT | NT | ++++ | N/A |
| −3 | ++++ | 0000 | 0000 | ++++ | ++++ | 0000 | |
| −4 | ++++ | 0000 | 0000 | ++++ | ++++ | 0000 | |
| −5 | ++++ | 0000 | 0000 | ++++ | ++++ | NT | |
| −6 | ++++ | 0000 | 0000 | +++0 | ++0+ | NT | |

TABLE S1-continued $Log_{10}$ reduction and percent reduction from control of hCoV229E (ATCC #VR-740) following 15- and 30 s by the test product: Sanitizer A

| Dilution ($-Log_{10}$) | Virus Control | Test: 15 seconds | Test: 30 seconds | NTC | NC | CTC | CC |
|---|---|---|---|---|---|---|---|
| −7 | 0000 | 0000 | 0000 | 0000 | 000+ | NT | |
| $TCID_{10}$ ($log_{10}$) | 6.50 | ≤2.50 | ≤2.50 | 6.25 | 6.50 | 2.50 | |
| $Log_{10}$ Reduction | N/A | ≥4.00 | ≥4.00 | | N/A | | |
| Percent Reduction | | ≥99.99 | ≥99.99 | | | | |

+ CPB (cytopathic/cytotoxic effect) present
1 CPE (cytopathic/cytotoxic effect) not detected
CC Cell Control
CTC Cytotoxicity Control
NC Neutralization Control
NTC Neutralizer Toxicity Control
NT Not tested
N/A Not applicable
CT Cytotoxicity

TABLE S2

$Log_{10}$ reduction and percent reduction from control of hCoV229E (ATCC #VR-740) following 5- and 10 min by the test product: CG-101 (5% w/w)

| Dilution ($-Log_{10}$) | Virus Control | Test: 5 minutes | Test: 10 minutes | NTC | NC | CTC | CC |
|---|---|---|---|---|---|---|---|
| −2 | NT | CT | CT | NT | NT | ++++ | 0000 N/A |
| −3 | ++++ | 0000 | 0000 | ++++ | ++++ | 0000 | |
| −4 | ++++ | 0000 | 0000 | ++++ | ++++ | 0000 | |
| −5 | ++++ | 0000 | 0000 | ++++ | ++++ | NT | |
| −6 | ++++ | 0000 | 0000 | +++0 | ++0+ | NT | |
| −7 | 0000 | 0000 | 0000 | 0000 | 000+ | NT | |
| $TCID_{10}$ ($log_{10}$) | 6.50 | ≤2.50 | ≤2.50 | 6.25 | 6.00 | 2.50 | |
| $Log_{10}$ Reduction | N/A | ≥4.00 | ≥4.00 | | N/A | | |
| Percent Reduction | | ≥99.99 | ≥99.99 | | | | |

+ CPE (cytopathic/cytotoxic effect) present
1 CPE (cytopathic/cytotoxic effect) not detected
CC Cell Control
CTC Cytotoxicity Control
NC Neutralization Control
NTC Neutralizer Toxicity Control
NT Not tested
N/A Not applicable
CT Cytotoxicity

TABLE S3

$Log_{10}$ microbial recoveries and $Log_{10}$ microbial reductions from control of *S. aureus* (ATCC #6538), by subject; immediately (30 min), 2 h, and 4 h following application of the test product: Sanitizer A

| | Immediately Post-Product Application | | | 2 hours Post-Product Application | | | 4 hours Post-Product Application | | |
|---|---|---|---|---|---|---|---|---|---|
| Subject | Untreated $Log_{10}$ Microbial Recovery | Treated $Log_{10}$ Microbial Recovery | $Log_{10}$ Reduction | Untreated $Log_{10}$ Microbial Recovery | Treated $Log_{10}$ Microbial Recovery | $Log_{10}$ Reduction | Untreated $Log_{10}$ Microbial Recovery | Treated $Log_{10}$ Microbial Recovery | $Log_{10}$ Reduction |
| 2 | * | * | * | * | * | * | * | * | * |
| 4 | 6.29 | 0.86 | 5.43 | 6.29 | 0.86 | 5.43 | 6.16 | 0.86 | 5.30 |

TABLE S3-continued $Log_{10}$ microbial recoveries and $Log_{10}$ microbial reductions from control of *S. aureus* (ATCC #6538), by subject; immediately (30 min), 2 h, and 4 h following application of the test product: Sanitizer A

| | Immediately Post-Product Application | | | 2 hours Post-Product Application | | | 4 hours Post-Product Application | | |
|---|---|---|---|---|---|---|---|---|---|
| Subject | Untreated $Log_{10}$ Microbial Recovery | Treated $Log_{10}$ Microbial Recovery | $Log_{10}$ Reduction | Untreated $Log_{10}$ Microbial Recovery | Treated $Log_{10}$ Microbial Recovery | $Log_{10}$ Reduction | Untreated $Log_{10}$ Microbial Recovery | Treated $Log_{10}$ Microbial Recovery | $Log_{10}$ Reduction |
| 13 | 6.31 | 0.86 | 5.45 | 6.24 | 0.86 | 5.38 | 6.17 | 0.86 | 5.31 |
| 15 | 6.26 | 0.86 | 5.40 | 6.18 | 0.86 | 5.32 | 6.03 | 0.86 | 5.17 |
| 1 | 6.26 | 0.86 | 5.40 | 6.17 | 0.86 | 5.31 | 6.01 | 0.86 | 5.15 |
| 6 | 6.32 | 0.86 | 5.47 | 6.21 | 0.86 | 5.35 | 6.19 | 0.86 | 5.33 |
| 8 | 6.35 | 0.86 | 5.49 | 6.28 | 0.86 | 5.42 | 6.23 | 0.86 | 5.37 |
| 11 | 6.40 | 0.86 | 5.54 | 6.38 | 0.86 | 5.52 | 6.40 | 0.86 | 5.54 |
| 12 | 6.34 | 0.86 | 5.48 | 6.27 | 0.86 | 5.41 | 6.36 | 0.86 | 5.50 |
| 14 | 6.20 | 0.86 | 5.34 | 6.19 | 0.86 | 5.33 | 6.29 | 0.86 | 5.43 |
| 5 | 6.25 | 0.86 | 5.39 | 6.32 | 0.86 | 5.46 | 6.24 | 0.86 | 5.38 |
| 10 | 6.30 | 0.86 | 5.44 | 6.16 | 0.86 | 5.30 | 6.20 | 0.86 | 5.34 |

Note:
The lowest detectable limit of the study was 0.86 $log_{10}$ $CFU/cm^2$
*Data unavailable due to an Adverse Event.

Although the disclosure has been described with reference to the above examples, it will be understood that modifications and variations are encompassed within the spirit and scope of the disclosure. Accordingly, the disclosure is limited only by the following claims.

What is claimed is:

1. A method of sanitizing a skin surface, comprising applying to the skin surface a composition comprising an ionic liquid having a cationic component and an anionic component, wherein:

the anionic component is bistriflimide anion, a geranate anion, dodecyldimethyl ammonia propane sulfonate anion, or a geraniolate anion, the cationic component is benzyl pyridinium cation, benzyl dimethyl dodecycl ammonium cation, a choline cation, benzethonium cation, or a phosphonium cation, and the composition is non-irritating to skin.

2. The method of claim 1, wherein the ionic liquid is a deep eutectic solvent having a melting point lower than the melting points of the cationic component and anionic component individually.

3. The method of claim 1, wherein the ionic liquid inhibits or decreases microbial growth on the skin surface.

4. The method claim 3, wherein the microbial growth is growth of a virus, bacterium, fungus, mold, protozoan, parasite, or combinations thereof.

5. The method of claim 4, wherein the bacterium is a gram-negative bacterium.

6. The method of claim 5, wherein the gram-negative bacterium is an *Escherichia, Salmonella, Klebsiella* bacterium, or any combination thereof.

7. The method of claim 6, wherein the *Escherichia* bacterium is *E. coli.*

8. The method of claim 4, wherein the bacterium is a gram-positive bacterium.

9. The method of claim 8, wherein the gram-positive bacterium is a *Staphylococcus* or *Streptococcus* bacterium.

10. The method of claim 9, wherein the *Staphylococcus* bacterium is methicillin-resistant *S. aureus* (MRSA).

11. The method of claim 4, wherein the virus is an Ebolavirus, Coronavirus, Rotavirus, Alphainfluenzavirus, Betainfluenzavirus, Deltainfluenzavirus, Gammainfluenzavirus, or any combination thereof.

12. The method of claim 4, wherein the virus is a Coronavirus.

13. The method of claim 12, wherein the Coronavirus is severe acute respiratory syndrome coronavirus 2 (SARS-CoV-2).

14. The method of claim 1, wherein the anionic component is a geranate.

15. The method of claim 1, wherein the cationic component is a choline cation.

16. The method of claim 1, wherein the cationic component is a choline cation, and wherein the anionic component is a geranate anion.

17. The method of claim 16, wherein the cationic component and the anionic component are in a molar ratio ranging from 1:1 to 1:2 (cationic component to anionic component).

18. The method of any one of claim 16, wherein the composition comprises from about 1% to about 8.5% of choline geranate by weight.

19. The method of claim 18, wherein the composition further comprises an alcohol in an amount of from about 50% to about 95% by weight.

20. The method of claim 19, wherein the alcohol is ethanol, isopropyl alcohol, n-propyl alcohol, or combinations thereof.

21. The method of any one of claim 19, wherein the composition further comprises from about from about 0.05% to about 5% by weight of hydroxypropyl cellulose.

22. The method of claim 21, wherein the composition further comprises from about 0.5% to about 5% by weight of glycerin.

23. The method of claim 1, wherein the composition is in the form of a liquid, a gel, a foam, a lotion, or a soap.

24. The method of claim 1, wherein the skin surface is a hand skin surface.

25. The method of claim 1, wherein the ionic liquid remains on the skin surface for at least two hours.

26. The method of claim 1, wherein the ionic liquid remains on the skin surface for at least four hours.

27. The method of claim 1, wherein the ionic liquid remains on the skin surface until cleaned or washed off.

* * * * *